US011135280B2

(12) United States Patent
Aman et al.

(10) Patent No.: US 11,135,280 B2
(45) Date of Patent: Oct. 5, 2021

(54) MODIFIED EBOLAVIRUS GLYCOPROTEINS COMPRISING MUTATIONS IN THE HEAD AND BASE DOMAINS THAT INCREASE ANTIBODY CROSS-REACTIVITY

(71) Applicants: INTEGRATED BIOTHERAPEUTICS, INC., Rockville, MD (US); INTEGRAL MOLECULAR, INC., Philadelphia, PA (US)

(72) Inventors: Mohammad Javad Aman, Rockville, MD (US); Katie A. Howell, North Bethesda, MD (US); Edgar Davidson, Philadelphia, PA (US); Benjamin J. Doranz, Drexel Hill, PA (US)

(73) Assignees: INTEGRATED BIOTHERAPEUTICS, INC., Rockville, MD (US); INTEGRAL MOLECULAR, INC., Philadelphia, PA (US)

( * ) Notice: Subject to any disclaimer, the term of this patent is extended or adjusted under 35 U.S.C. 154(b) by 0 days.

(21) Appl. No.: 16/084,151

(22) PCT Filed: Mar. 27, 2017

(86) PCT No.: PCT/US2017/024320
§ 371 (c)(1),
(2) Date: Sep. 11, 2018

(87) PCT Pub. No.: WO2017/172622
PCT Pub. Date: Oct. 5, 2017

(65) Prior Publication Data
US 2019/0381162 A1    Dec. 19, 2019

Related U.S. Application Data

(60) Provisional application No. 62/314,009, filed on Mar. 28, 2016, provisional application No. 62/423,584, filed on Nov. 17, 2016.

(51) Int. Cl.
*A61K 39/12*     (2006.01)
*C07K 14/005*    (2006.01)
*C12N 15/86*     (2006.01)

(52) U.S. Cl.
CPC ............ *A61K 39/12* (2013.01); *C07K 14/005* (2013.01); *C12N 15/86* (2013.01); *C12N 2760/14122* (2013.01); *C12N 2760/14134* (2013.01)

(58) Field of Classification Search
CPC .......... A61K 39/12; C12N 2760/14122; C12N 2760/14134
See application file for complete search history.

(56) References Cited

U.S. PATENT DOCUMENTS

2009/0232841 A1*  9/2009  Sullivan ................. A61P 31/14
424/204.1

FOREIGN PATENT DOCUMENTS

WO    2017/172622 A1    10/2017

OTHER PUBLICATIONS

Winkler, K., et al., 2000, Changing the antigen binding specificity by single point mutations of an anti-24 (HIV-1) antibody, J. Immunol. 165:4505-4514.*
Zhang, Q., et al., May 2016, Potent neutralizing monoclonal antibodies against Ebola virus infection, Nature Scientific Reports 6: 25856 (pp. 1-15).*
Takada, A., et al., Jan. 2003, Identification of Protective Epitopes on Ebola Virus Glycoprotein at the Single Amino Acid Level by using Recombinant Vesicular Stomatitis Viruses, J. Virol. 77(2): 1069-1074.*
Keck, Z.-Y., et al., Jan. 2016, Macaque monoclonal antibodies targeting novel conserved epitopes within filovirus glycoprotein, J. Virol. 90(1):279-291.*
Keck et al., "Macaque Monoclonal Antibodies Targeting Novel Conserved Epitopes within Filovirus Glycoprotein", Journal of Virology, Oct. 2015, pp. 279-291, vol. 90, No. 1.
Fusco et al., "Protective mAbs and Cross-Reactive mAbs Raised by Immunization with Engineered Marburg Virus GPs", PLoS Pathogens, Jun. 26, 2015, pp. 1-17, vol. 11, No. 6.
Lee et al., "Structure of the Ebola Virus Glycoprotein Bound to an Antibody from a Human Survivor", Nature, Jul. 10, 2008, pp. 177-182, vol. 454, No. 7201.
Dowling et al., "Influences of Glycosylation on Antigenicity, Immunogenicity, and Protective Efficacy of Ebola Virus GP DNA Vaccines", Journal of Virology, Dec. 2006, pp. 1821-1837, vol. 81, No. 4.
Misasi et al., "Structural and Molecular Basis for Ebola Virus Neutralization by Protective Human Antibodies", Science, Feb. 2006, pp. 1343-1346, vol. 351, No. 6279.
Feldmann et al., "Ebola Virus: From Discovery to Vaccine", Nat Rev Immunol, 2003, pp. 677-685, vol. 3, No. 8.
Kuhn et al., "Nomenclature- and Database-Compatible Names for the Two Ebola Virus Variants that Emerged in Guinea and the Democratic Republic of Congo in 2014", Viruses, 2014, pp. 4760-4799, vol. 6, No. 11.
Feldmann et al., Curr Opin Investig Drugs, 2005, pp. 823-830, vol. 6, No. 8.
Geisbert et al., "Prospects for Immunisation Against Marburg and Ebola Viruses", Reviews in Medical Virology, Nov. 20, 2010, pp. 344-357, vol. 20, No. 6.
Marzi et al., "Ebola Virus Vaccines: An Overview of Current Approaches", Expert Review of Vaccines, Feb. 27, 2014, pp. 521-531, vol. 13, No. 4.

(Continued)

Primary Examiner — Jeffrey S Parkin
(74) Attorney, Agent, or Firm — Thompson Coburn LLP; William A. Holtz

(57) ABSTRACT

Provided herein are methods of incorporating substitutions of specified residues into a filovirus GP in order to increase immunogenicity and/or broaden the cross-reactivity of the protective immune response against other filovirus members. Also provided herein are mutant filovirus GPs comprising such substitutions.

13 Claims, 13 Drawing Sheets

Specification includes a Sequence Listing.

(56) References Cited

OTHER PUBLICATIONS

Henoa-Restrepo et al., "Efficacy and Effectiveness of an rVSV-Vectored Vaccine Expressing Ebola Surface Glycoprotein: Interim Results from the Guinea Ring Vaccination Cluster-Randomised Trial", Lancet, Aug. 3, 2015, pp. 857-866, vol. 386, No. 9996.
Manicassamy et al., "Comprehensive Analysis of Ebola Virus GP1 in Viral Entry", Journal of Virology, Apr. 2005, pp. 4793-4805, vol. 79, No. 8.
Feldmann et al., "Molecular Biology and Evolution of Filoviruses", Archives of Virology Supplementum, 1993, pp. 81-100, vol. 7.
Feldmann et al., "Glycosylation and Oligomerization of the Spike Protein of Marburg Virus", Virology, 1991, pp. 353-356, vol. 182, No. 1.
Geisbert et al., "Differentiation of Filoviruses by Electron Microscopy", Virus Research, 1995, pp. 129-150, vol. 39, No. 2-3.
Kiley et al., "Physicochemical Properties of Marburg Virus: Evidence for Three Distinct Virus Strains and Their Relationship to Ebola Virus", Aug. 1, 1988, Journal of General Virology, pp. 1957-1967, vol. 69.
Kuhn et al., J Bio Chem, 2006, pp. 15951-15958, vol. 281, No. 23.
Sanchez et al., "Biochemical Analysis of the Secreted and Virion Glycoproteins of Ebola Virus", Journal of Virology, 1998, pp. 6442-6447, vol. 72, No. 8.
Chandran et al., "Endosomal Proteolysis of the Ebola Virus Glycoprotein is Necessary for Infection", Science, 2005, pp. 1643-1645, vol. 308, No. 5728.
Kaletsky et al., Journal of Virology, 2007, pp. 13378-13384, vol. 81, No. 24.
Schornberg et al., "Role of Endosomal Cathepsins in Entry Mediated by the Ebola Virus Glycoprotein", Journal of Virology, 2006, pp. 4174-4178, vol. 80, No. 8.
Dube et al., "The Primed Ebolavirus Glycoprotein (19-Kilodalton GP1,2): Sequence and Residues Critical for Host Cell Binding", Journal of Virology, 2009, pp. 2883-2891, vol. 83.
Aman, Journal of Molecular Biology, 2016, pp. , vol. 7, No. 2.
Lee et al., "Neutralizing Ebolavirus: Structural Insights into the Envelope Glycoprotein and Antibodies Targeted Against it", Curr Opin Struct Biol, 2009, pp. 408-417, vol. 19.
Saphire, "An Update on the Use of Antibodies Against the Filoviruses", Immunotherapy, 2013, pp. 1221-1233, vol. 5, No. 11.
Saphire et al., "Feverish Quest for Ebola Immunotherapy: Straight or Cocktail?", Trends in Microbiology, 2016, pp. 684-686, vol. 24, No. 9.
Warfield et al., "Induction of Humoral and CD8+ T Cell Responses Are Required for Protection Against Lethal Ebola Virus Infection", Journal of Immunology, 2005, pp. 1184-1191, vol. 175, No. 2.
Dye et al., "Postexposure Antibody Prophylaxis Protects Nonhuman Primates from Filovirus Disease", Proceedings of the National Academy of Sciences in the United States of America, 2012, pp. 5034-5039, vol. 109, No. 13.
Olinger et al., "Delayed Treatment of Ebola Virus Infection with Plant-Derived Monoclonal Antibodies Provides Protection in Rhesus Macaques", Proceedings of the National Academy of Sciences in the USA, 2012, pp. 18030-18035, vol. 107, No. 44.
Qui et al., Science of Translational Medicine, 2013, pp. , vol. 5, No. 207.
Qui et al, Journal of Virology, 2013, pp. 7754-7757, vol. 87, No. 13.
Holtsberg et al., "Pan-Ebolavirus and Pan-Filovirus Mouse Monoclonal Antibodies: Protection Against Ebola and Sudan Viruses", Journal of Virology, 2015, pp. 266-278, vol. 90.
Howell et al., "Antibody Treatment of Ebola and Sudan Virus Infection via a Uniquely Exposed Epitope within the Glycoprotein Receptor-Binding Site", Cell Reports, 2016, pp. 1514-1526, vol. 15.

\* cited by examiner

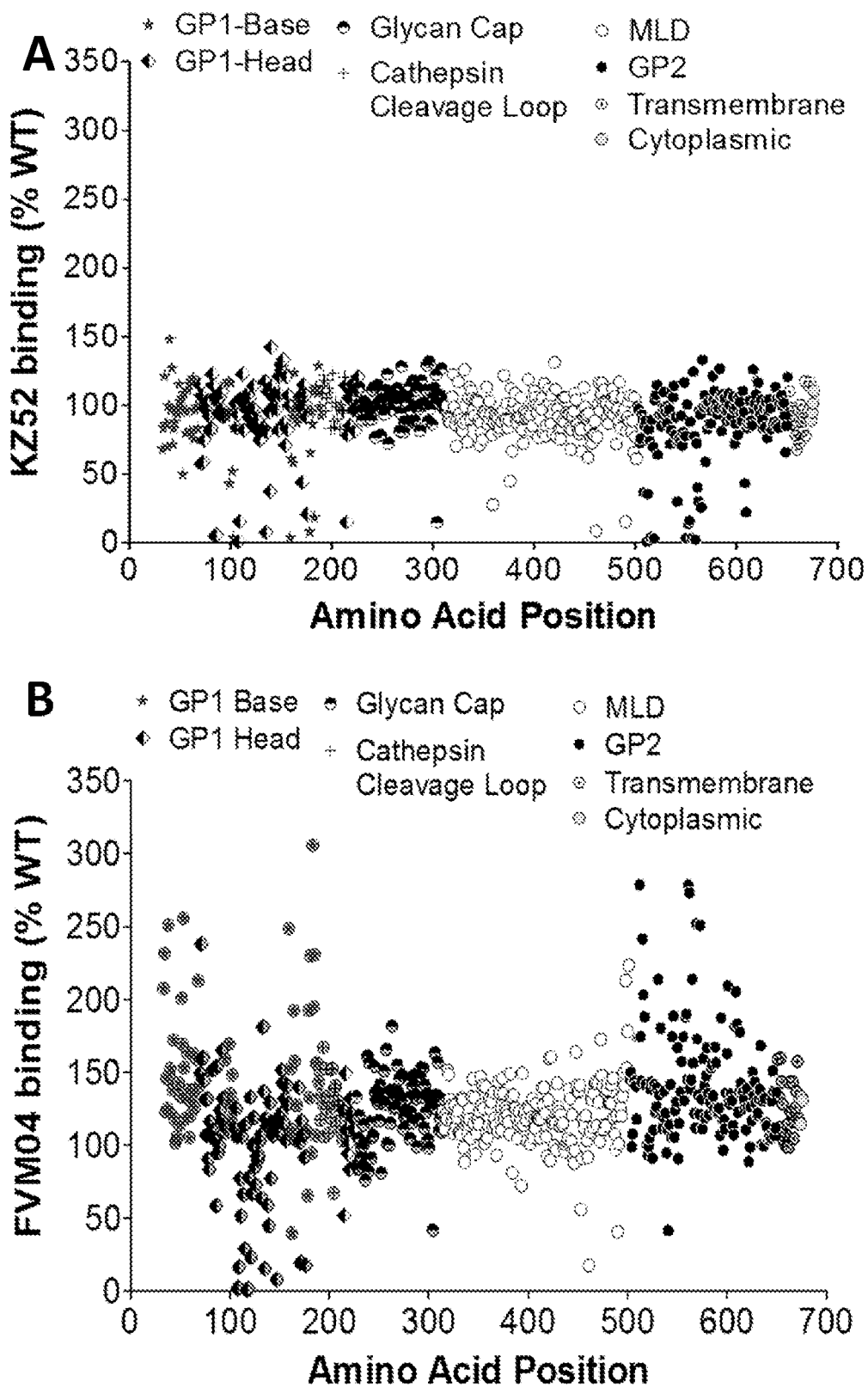
FIG. 2A-B

FIG. 2C-D

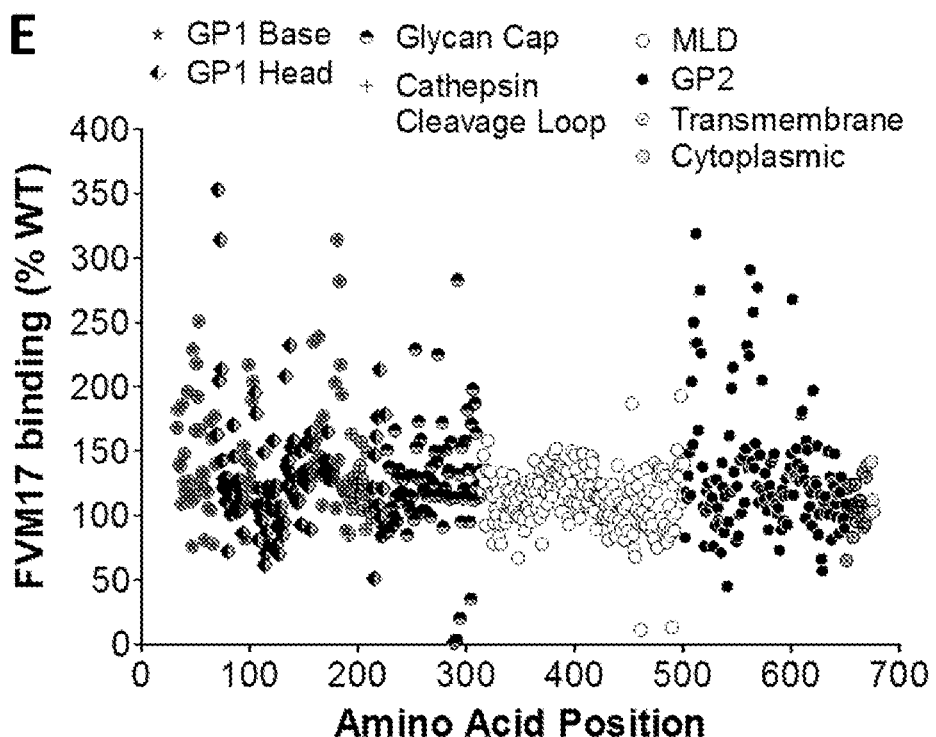
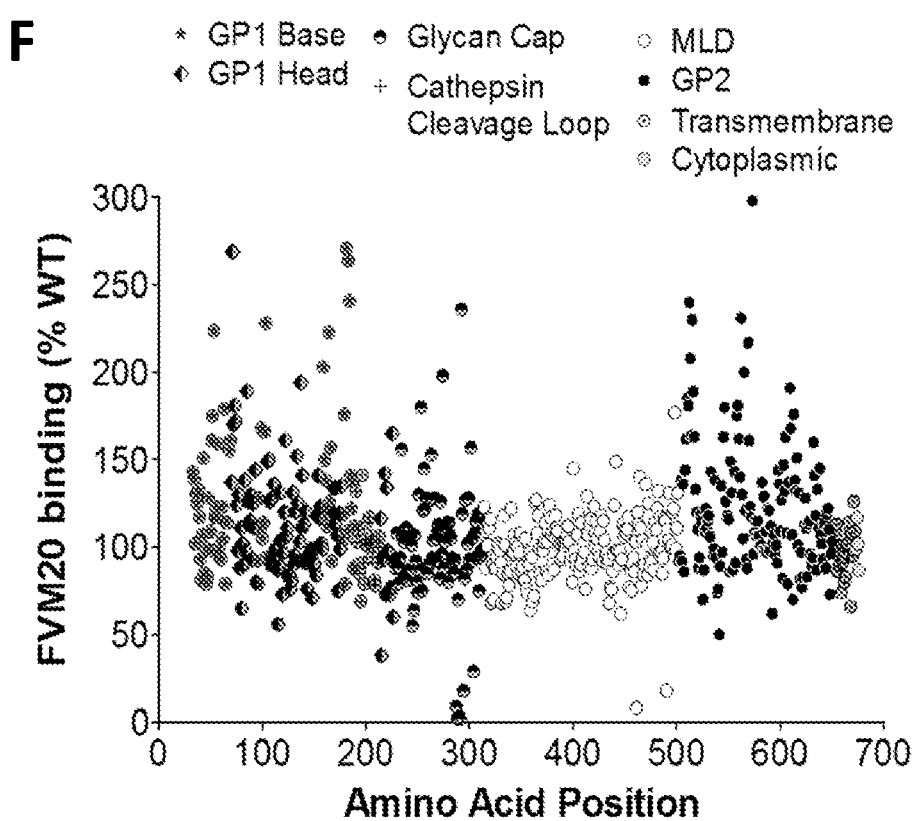
FIG. 2E-F

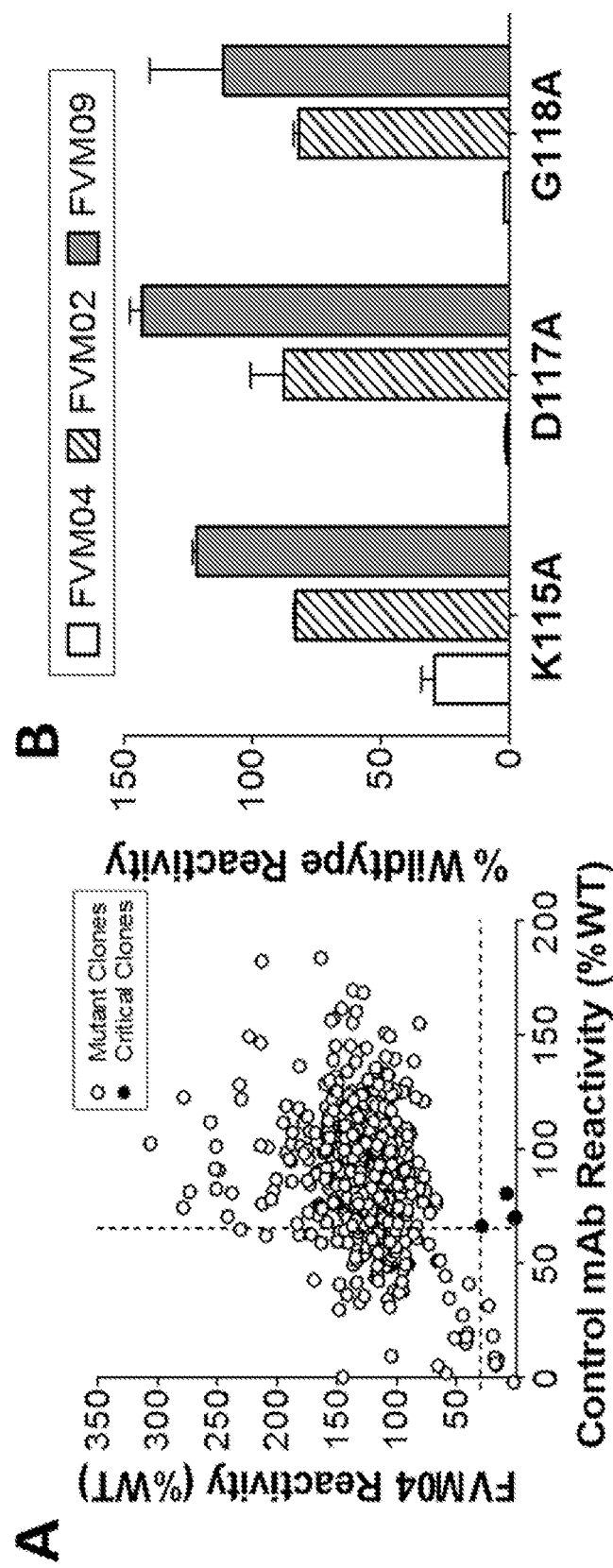
FIG. 3A-B

C

| | | β7 → | |
|---|---|---|---|
| EBOV GP | 104 | WAENCYNLEIKKPDGSEC | 121 |
| SUDV GP | 104 | WAENCYNLEIKKPDGSEC | 121 |
| BDBV GP | 104 | WAENCYNLDIKKADGSEC | 121 |
| RESTV GP | 104 | WAENCYNLEIKKSDGSEC | 121 |
| TAFV GP | 104 | WAENCYNLAIKVDGSEC | 121 |
| MARV GP | 88 | EAKTCYNISVTDPSGKSL | 105 |

FIG. 3C

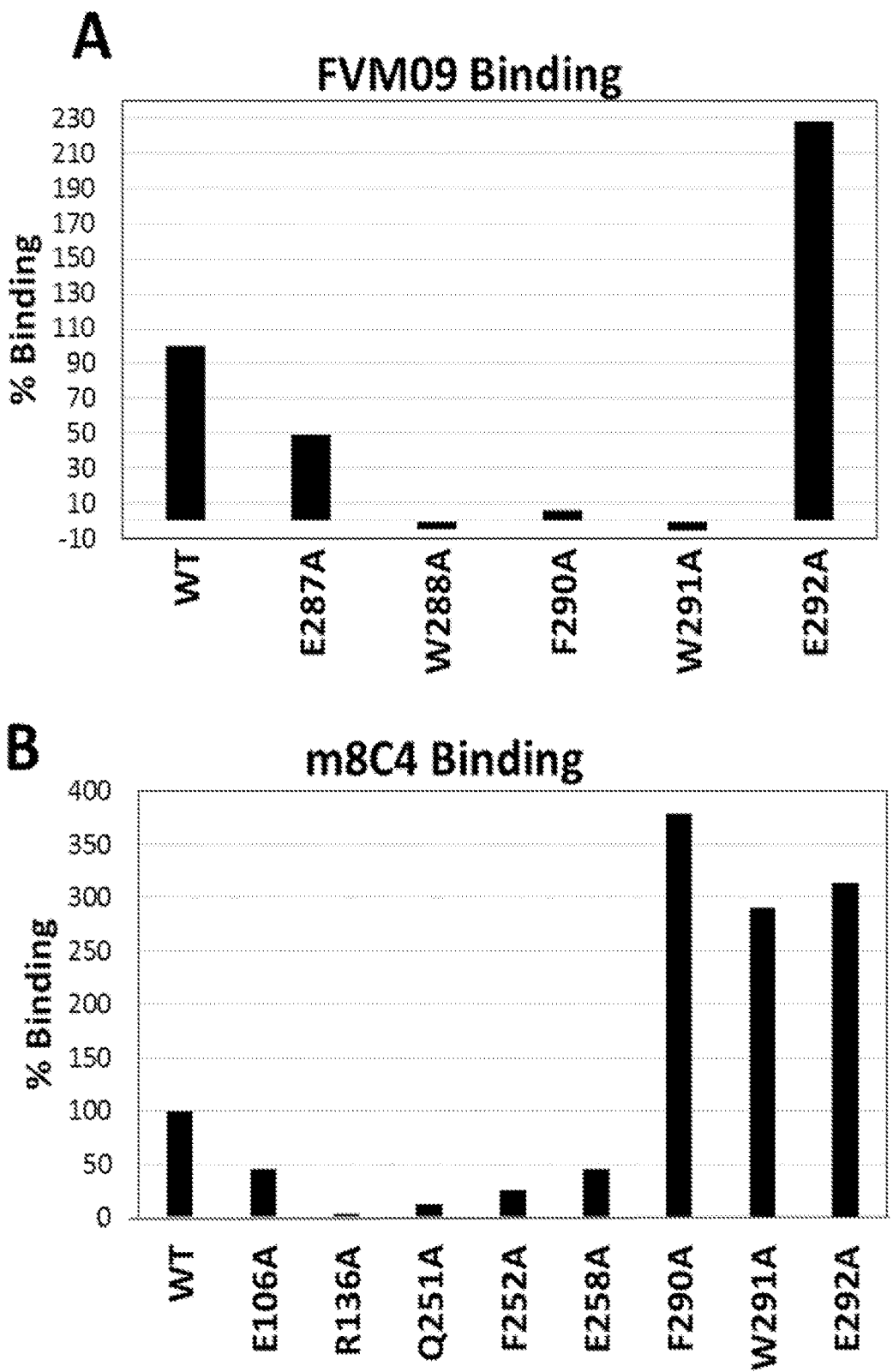
FIG. 5A-B

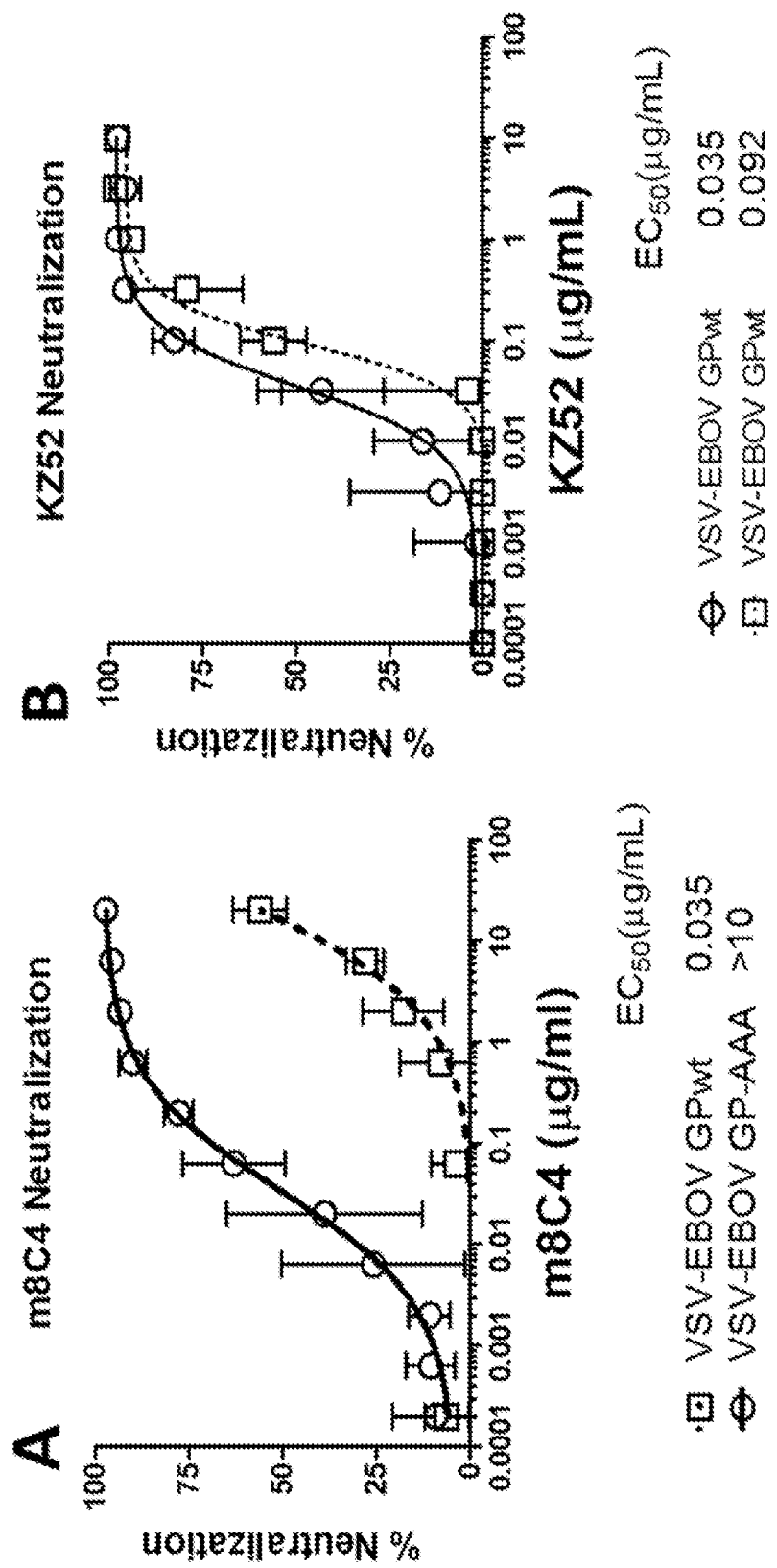
FIG. 6A-B

FIG. 8

MODIFIED EBOLAVIRUS GLYCOPROTEINS COMPRISING MUTATIONS IN THE HEAD AND BASE DOMAINS THAT INCREASE ANTIBODY CROSS-REACTIVITY

CROSS-REFERENCE TO RELATED APPLICATIONS

This patent application is a 35 U.S.C. § 371 U.S. National Phase Application of International Patent Application No. PCT/US2017/024320, filed Mar. 27, 2017, which claims priority to U.S. Provisional Application No. 62/314,009 filed Mar. 28, 2016 and U.S. Provisional Application No. 62/423,584 filed Nov. 17, 2016, all of which are incorporated by reference herein in their entireties.

STATEMENT REGARDING FEDERALLY-SPONSORED RESEARCH AND DEVELOPMENT

Statement under MPEP 310. This invention was made with government support under HDTRA1-13-C-0015 awarded by US Defense Threat Reduction Agency (DTRA), HHSN272201400058C awarded by US Department of Health and Human Services (HHS) and NIAID grant AI098178 awarded by National Institute of Allergy and Infectious Diseases (NIAID). The government has certain rights in the invention."

REFERENCE TO SEQUENCE LISTING SUBMITTED ELECTRONICALLY

A Sequence Listing is provided herewith as a part of this U.S. Patent Application via the USPTO's EFS system in the filed named "57783_178282_Sequence_Listing_ST25.txt" which is 85,067 bytes in size (measured in MS-Windows®), created on Aug. 13, 2019, and is incorporated herein by reference in its entirety.

BACKGROUND

Filoviruses, the ebolaviruses and marburgvirus, cause severe hemorrhagic fevers in humans, with mortality rates reaching 88% (Feldmann, et al., 2003, *Nat Rev Immunol,* 3 (8): 677-685) as well as epizootics in nonhuman primates and probably other mammals. There are currently no vaccines or therapeutics approved against filoviruses. Filoviruses consist of five Ebolavirus species and a single species of Marburgvirus (Kuhn, et al., 2014, *Viruses,* 24; 6(11): 4760-99). The main ebolavirus species causing outbreaks in humans are Ebola virus (EBOV; formerly known as Zaire Ebola virus), Sudan virus (SUDV) and Bundibugyo virus (BDBV) (Kuhn, et al., 2014, *Viruses,* 24; 6(11): 4760-99). Filoviruses are enveloped, single-stranded, negative sense RNA filamentous viruses and encode seven proteins, of which the spike glycoprotein (GP) is considered the main protective antigen and vaccine target (Feldmann, et al., 2003, *Nat Rev Immunol,* 3 (8): 677-685; Feldmann, et al., 2005, *Curr Opin Investig Drugs,* 6 (8): 823-830; Geisbert, et al., 2010, *Rev Med Virol,* 20(6): 344-57).

Four vector-based approaches and DNA vaccine strategies against filoviruses have been reported including replication-incompetent Venezuelan equine encephalitis virus (VEE) replicons, adenoviral vectors, live recombinant vesicular stomatitis virus (VSV), and parainfluenza (PIV) vectored vaccines (Geisbert, et al., 2010, *Rev Med Virol,* 20(6): 344-57; Marzi and Feldmann, 2014, *Expert Rev Vaccines,* 13 (4): p. 521-31). The VSV-based vaccine was recently tested with apparent success for efficacy in humans infected with EBOV during the 2014 West Africa Ebola virus disease (EVD) outbreak (Henao-Restrepo, 2015, *Lancet,* 386(9996): 857-66). The current vaccine candidates are designed based on the wild-type sequence of GP of specific filovirus species or strain. However, these vaccines are unable to cross-protect against multiple species of ebolavirus or Marburgvirus (Geisbert, et al., 2010, *Rev Med Virol,* 20(6): 344-57). It is also not clear if a simple mixing of vaccines for different species will provide broad protection against multiple species of filoviruses. Thus, vaccines designed to induce broadly protective immune responses are highly desired.

GP is proteolytically cleaved by furin protease into two subunits linked by a disulfide linkage: GP1 (~140 kDa) and GP2 (~38 kDa) (Manicassamy, et al., 2005, *J Virol,* 79 (8): 4793-4805). Three GP1-GP2 units form the trimeric GP envelope spike (~550 kDa) on the viral surface (Feldmann, et al., 1993, *Arch Virol Suppl,* 7:81-100; Feldmann, et al., 1991, *Virology,* 182 (1): 353-356; Geisbert and Jahrling, 1995, *Virus Res,* 39 (2-3): 129-150; Kiley, et al., 1988a, *J Gen Virol,* 69 (Pt 8): 1957-1967). GP1 mediates cellular attachment (Kiley, et al., 1988b, *J Gen Virol,* 69 (Pt 8): 1957-1967; Kuhn, et al., 2006, *J Biol Chem,* 281 (23): 15951-15958), and contains a mucin-like domain (MLD) which is heavily glycosylated and variable and has little or no predicted secondary structure (Sanchez, et al., 1998, *J Virol,* 72 (8): 6442-6447).

A specific region of the MARV and EBOV GP1 consisting of ~150 amino acids has been identified (Kuhn, et al., 2006, *J Biol Chem,* 281 (23): 15951-15958) that binds filovirus receptor-positive cells, but not receptor-negative cells, more efficiently than GP1, and compete with the entry of the respective viruses (Kuhn, et al., 2006, *J Biol Chem,* 281 (23): 15951-15958). These properties are similar to regions defined for SARS coronavirus and Machupo arenavirus (Li, et al., 2003, *Nature,* 426 (6965): 450-454; Radoshitzky, et al., 2007, *Nature,* 446 (7131): 92-96; Wong, et al., 2004, *J Biol Chem,* 279 (5): 3197-3201). This region of GP is referred to as receptor binding region (RBR) and is part of a larger domain that excludes the highly variable, glycosylated, and bulky mucin-like domain (MLD). The RBR shows the highest level of homology between Filovirus glycoproteins (Kuhn, et al., 2006, *J Biol Chem,* 281 (23): 15951-15958).

The crystal structure of the trimeric, pre-fusion conformation of EBOV GP (lacking MLD) in complex with the EBOV-specific neutralizing antibody KZ52 was solved at 3.4 Å (Lee, et al., 2008, *Nature,* 454 (7201): 177-182). This suggests a GP structure where three GP1 subunits assemble to form a chalice, cradled in a pedestal of the GP2 fusion subunits, while the MLD restricts access to the conserved RBR, sequestered in the GP chalice bowl (FIG. 1). The Base of the structure consists of the entire GP2 as well as residues 33-69, 95-104, 159-168, and 177-189 of GP1, referred to here as the GP1 base. The residues within the GP1 base closely interact with GP2 residue and contribute to the integrity of the trimeric structure (Lee, et al., 2008, *Nature,* 454 (7201): 177-182). The chalice itself consists of the so called core GP1 or GP1 head domain consisting of residues 70-94, 105-158, 169-176, and 214-226. An additional highly glycosylated GP1 domain called the glycan cap (residues 227-313) is located on the rim of the chalice.

Filovirus GPs are cleaved by cathepsin proteases as a step in entry, reducing GP1 to a ~18 kDa product (Chandran, et al., 2005, *Science,* 308 (5728): 1643-1645; Kaletsky, et al., 2007, *J Virol*, 81 (24): 13378-13384; Schomberg, et al., 2006, *J Virol*, 80 (8): 4174-4178). The structures suggest that the most likely site of cathepsin cleavage is the flexible and structurally disordered β13-β 14 loop (residues 190-213) of GP1 and illustrate how cleavage there would release the heavily glycosylated regions from GP, leaving just the core of GP1, encircled by GP2 that interacts with the GP1 base residues, with the RBR now well exposed. Cathepsin cleavage enhances infection, presumably as a result of better exposing the RBR for interaction with cell surface factors trafficked with the virus into the endosome (Dube, et al., 2009, *J Virol*, 83:2883-2891). On the surface of the authentic virus, the MLD probably dominates host-interaction surfaces of filovirus GP, and indeed, antibodies against the MLD have been frequently identified. The seclusion of the receptor binding region (RBR) in the full length GP and its exposure during entry in the endosome suggest that targeting of neutralizing antibodies that recognize RBR to the endosomes may be useful in achieving effective neutralization of the filoviruses. The monoclonal antibody FVM04 is a prototypic inhibitor of receptor binding and consistent with the conserved nature of the RBR, FVM04 cross neutralizes multiple ebolaviruses and protects against Ebola virus and Sudan virus infections in animal models (Howell, et al., 2016, *Cell Rep*, 15(7):1514-26).

$GP_{CL}$-NPC1 interaction positions the internal fusion domain (IFL) of GP to interact with the endosomal membrane and trigger viral membrane fusion. While $GP_{CL}$-NPC1 interaction is required for membrane fusion, it is not sufficient. (Aman, 2016, *MBio*, 7 (2): e00346-16). This process of fusion triggering involves major conformational rearrangement that are only partially understood likely dependent of acid and protease dependent processes that still remain to be defined in details. The trigger unwinds the GP2 helical structure from around the GP1 positioning IFL next to the endosomal membrane and allowing it to penetrate the endosomal membrane. As a result the pre-hairpin intermediate pulls together the viral and endosomal membrane, leading to hemifusion followed by formation of a fusion pore and post-fusion six helix bundle structure (Lee and Saphire, 2009, *Curr Opin Struct Biol* 19:408-17; Aman, 2016, *MBio*, 7 (2): e00346-16). The virus then delivers its content through this pore into the host cytoplasm. The IFL consists of a two-strand beta sheet and a connecting loop that wrap arounds GP1. The Monoclonal antibodies KZ52 bind a species specific epitope at the base of the IFL (Lee, et al., 2008, *Nature*, 454 (7201): 177-182). While binding to this epitope by KZ52-like antibodies leads to potent inhibition of viral fusion, the epitope is highly specific to EBOV (Zaire) and KZ52 does not cross react with other ebolaviruses (Saphire, 2013, *Immunotherapy*, 5(11):1221-33). Thus development of therapeutic antibodies that inhibit the fusion of multiple ebolaviruses is highly desirable. Such antibodies would likely bind to the stem (the beta sheets β19 and β20 (Lee, et al., 2008, *Nature*, 454 (7201): 177-182)) or the tip of the IFL. We have previously reported that FVM02, a mAb that binds to the tip of the fusion loop but does not contact GP1, is unable to neutralize ebolaviruses. In contrast every neutralizing antibody that binds to the base of the GP trimer and neutralizes the virus contacts both GP1 and GP2, effectively bracing the two subunits (Saphire and Aman, 2016, *Trends Microbiol.*, 24(9):684-686). This bracing effect most likely mechanically interferes with the structural rearrangements required for productive fusion (Saphire and Aman, 2016, *Trends Microbiol.*, 24(9):684-686). The IFL closely interacts with GP1 particularly with the residues in the β3 strand (such as R64) as well as the N-terminal portion of the cathepsin cleavage loop (The loop consists of residues A189-Y214) suggesting that antibodies that contact both GP1 and GP2 residues in this region can brace the GP1 and GP2 and inhibit fusion. The antibody CA45 is a macaque-derived panfilovirus antibody that binds to the ebolavirus GP IFL across four different species of ebolavirus, EBOV, SUDV, RESTV, and BDBV (U.S. Provisional Application No. 62/406,598, filed Oct. 11, 2016, which is incorporated by reference herein in its entirety).

Role of antibodies in protection against filovirus hemorrhagic fever: While both T and B cell responses are reported to play a role in protective immune responses to filoviruses (Warfield, et al., 2005, *J Immunol*, 175 (2): 1184-1191), a series of recent reports indicate that antibody alone can provide significant protection. Dye et al showed that purified convalescent IgG from macaques can protect NHPs against challenge with MARV and EBOV when administered as late as 48 h post exposure (Dye, et al., 2012, *Proc Natl Acad Sci USA*, 109(13):5034-9). Olinger et al reported significant protection from EBOV challenge in NHPs treated with a cocktail of three monoclonal antibodies (mAbs) to GP administered 24 h and 48 h post exposure (Olinger, et al., 2012, *Proc Natl Acad Sci USA*, 109(44):18030-18035). Similar results were also reported in two other studies (Qiu, et al., 2013, *Sci Transl Med*, 5 (207): 207ra143; Qiu, et al., 2013, *J Virol*, 87(13):7754-7757). A recent study shows that a combination of three monoclonal antibodies, called ZMAPP™, can protect monkeys when administered five days after exposure to EBOV, at a time when the disease is fully manifest and the viremia is at its peak (Qiu, et al., 2014, *Nature*, 514(7520):47-53). Collectively these data demonstrate the ability of the humoral response to control filovirus infection. While ZMapp™ is strictly specific for EBOV, recent reports show that development of antibodies with broad neutralizing and protective property is feasible (WO2016/069627 and Keck, et al., 2015, *J Virol*, 90:279-291; WO2015/200522A2 and Holtsberg, et al., 2015, *J Virol*, 90:266-278; Howell et al. 2016, *Cell Reports*, 15, 1514-1526).

SUMMARY

This disclosure provides an immunogen that includes a filovirus spike glycoprotein (GP) or immunogenic fragment thereof, where the filovirus GP includes the GP head domain or an immunogenic fragment thereof and the GP base domain or an immunogenic fragment thereof, where the base domain can include one or more single amino acid substitutions relative to the corresponding wild-type filovirus GP amino acid sequence, and where the one or more amino acid substitutions can affect the conformation of a cross-reactive epitope in the head domain, thereby increasing immunogenicity of the immunogen against the corresponding wild-type filovirus GP, and/or broadening the cross-reactive immunogenicity of the immunogen against other filovirus species or strains. In certain aspects, the wild-type filovirus is a wild-type Ebola virus (EBOV), and the amino acid substitution(s) in the GP base domain can include an amino acid substitution: at a position corresponding to C53, F183, N512, A562, L569, or L573 of the wild-type Ebola virus (EBOV) GP, or a combination thereof; at a position corresponding to F159, P513, L515, or T565 of the wild-type EBOV GP, or a combination thereof; at a position corresponding to R164, L184, 1185, H516, or G546 of the wild-type EBOV GP, or a combination thereof; at a position corresponding to L51, G179, Q508, C511, Y517, R559, or C601 of the wild-type EBOV GP, or a combination thereof; at a position corresponding to 133, P34, 138, V48, V52, V66, E103, A182, R498, R501, N514, W531, P533, E545, C556, L561, S583, or I610 of the wild-type EBOV GP, or a combination thereof; at a position corresponding to L43, V45, R54, L57, L63, V66, E71, Y99, L161, L165, P187, N506, P509, K510, W518, A525, L558, Q560, E564, T566, Q570, 1603, L604, G605, C608, C609, D614, T616, 1623, or W648 of the wild-type EBOV GP, or a combination thereof; or at a position corresponding to C53, F183, N512, A562, L569, L573, F159, P513, L515, T565, R164, L184, 1185, H516, G546, L51, G179, Q508, C511, Y517, R559, C601, 133, P34, 138, V48, V52, L68, E103, A182, R498, R501, N514, W531, P533, E545, C556, L561, S583, 1610, L43, V45, R54, L57, L63, L66, E71, Y99, L161, L165, P187, N506, P509, K510, W518, A525, L558, Q560, E564, T566, Q570, 1603, L604, G605, C608, C609, D614, T616, 1623, or W648 of the wild-type EBOV GP, or a combination thereof. In certain aspects, the wild-type Ebola virus is EBOV strain Mayinga-76. In certain aspects, the other Filovirus species or strain against which cross-reactivity is broadened to include can be EBOV, SUDV, BDBV, RESTV, TAFV, MARV, any strain thereof, or a combination thereof.

The disclosure further provides an immunogen that includes a filovirus spike glycoprotein (GP) or immunogenic fragment thereof, wherein the filovirus GP comprises the GP head domain or an immunogenic fragment thereof and the GP base domain or an immunogenic fragment thereof, wherein the base domain comprises one or more single amino acid substitutions relative to the corresponding wild-type filovirus GP amino acid sequence, and wherein the one or more amino acid substitutions can affect the conformation of a species specific epitope in the base domain, thereby masking an immunodominant epitope in the base domain. In certain aspects the wild-type filovirus is a wild-type Ebola virus (EBOV), and the amino acid substitution(s) in the GP base domain can include an amino acid substitution at a position corresponding to E103, F159, E178, F183, C511, L515A, W518, N550, D552, G553, C556, or R559 of the wild-type EBOV GP, or a combination thereof. In certain aspects, the one or more amino acid substitutions can also increase immunogenicity of the immunogen against the corresponding wild-type filovirus GP, and/or broadens the cross-reactive immunogenicity of the immunogen against other filovirus species or strains. In certain aspects, the wild-type filovirus is a wild-type Ebola virus (EBOV), and the amino acid substitution(s) in the GP base domain can include an amino acid substitution: at a position corresponding to F159, F183, C511, L515, or R559 of the wild-type EBOV GP, or a combination thereof; e.g., at a position corresponding to F183 of the wild-type EBOV GP. In certain aspects, the wild-type Ebola virus is EBOV strain Mayinga-76. In certain aspects, the other filovirus species or strain against which cross-reactivity is broadened to include can be EBOV, SUDV, BDBV, RESTV, TAFV, MARV, any strain thereof, or a combination thereof.

In various aspects, an immunogen as provided above can further include the glycan cap of the filovirus GP1 subunit or an immunogenic fragment thereof.

In certain aspects the disclosure further provides an immunogen that includes a filovirus spike glycoprotein (GP) or immunogenic fragment thereof that includes the GP head domain or an immunogenic fragment thereof, the GP base domain or an immunogenic fragment thereof, and the glycan cap or an immunogenic fragment thereof, where the glycan cap can include one or more single amino acid substitutions relative to the corresponding wild-type filovirus GP, and where the one or more amino acid substitutions can reduce glycosylation of the glycoprotein, thereby increasing immunogenicity of the immunogen against the corresponding wild-type filovirus GP, and/or broadening the cross-reactive immunogenicity of the immunogen against other filovirus species or strains, e.g., EBOV, SUDV, BDBV, RESTV, TAFV, MARV, any strain thereof, or a combination thereof. In certain aspects, the wild-type filovirus is a wild-type Ebola virus (EBOV), and wherein the amino acid substitution(s) in the glycan cap can be an amino acid substitution at a position corresponding to N238, T240, N257, T259, N268, or T270 of the wild-type EBOV GP, or a combination thereof. In certain aspects the amino acid substitution in the glycan cap can include at least two single amino acid substitutions at positions corresponding to N238 and/or T240, N257 and/or T259, or N268 and/or T270 of the wild-type EBOV GP, wherein the substitutions disrupt at least two glycosylation sites. In certain aspects, the wild-type Ebola virus is EBOV strain Mayinga-76.

In certain aspects the disclosure further provides an immunogen that includes a filovirus spike glycoprotein (GP) or immunogenic fragment thereof, where the filovirus GP includes the GP head domain or an immunogenic fragment thereof, the GP base domain or an immunogenic fragment thereof, and the glycan cap or immunogenic fragment thereof, where the glycan cap includes one or more single amino acid substitutions relative to the corresponding wild-type filovirus GP amino acid sequence within the disordered loop connecting the β17 to β18 strands, and where the one or more amino acid substitutions can affect the conformation of a cross-reactive epitope in the glycan cap, thereby increasing the immunogenicity of the immunogen against the corresponding wild-type filovirus GP, and/or broadening the cross-reactive immunogenicity of the immunogen against other filovirus species or strains e.g., EBOV, SUDV, BDBV, RESTV, TAFV, MARV, any strain thereof, or a combination thereof. In certain aspects, the wild-type filovirus is a wild-type Ebola virus (EBOV), and the amino acid substitution(s) in the glycan cap includes an amino acid substitution: at a position corresponding to F290, W291, or E292 of the wild-type EBOV GP, or a combination thereof, e.g., at a position corresponding to E292 of the wild-type EBOV GP. In certain aspects the wild-type filovirus is a wild-type Ebola virus (EBOV) that includes a glycan cap, and the glycan cap comprises: (i) an amino acid substitution at a position corresponding N238, T240, N257, T259, N268, or T270 of the wild-type EBOV GP, or a combination thereof; and (ii) an amino acid substitution at a position corresponding to F290, W291, or E292 of the wild-type EBOV GP, or a combination thereof. In certain aspects, the wild-type Ebola virus is EBOV strain Mayinga-76.

In certain aspects of any of the provided immunogens, the wild-type amino acid is substituted with an alanine (A) residue, except where the wild-type amino acid is A. Where the wild-type amino acid is A it can be substituted with a serine (S) residue. In certain aspects of any of the provided immunogens, the wild-type amino acid is substituted with a glycine (G) residue, except where the wild-type amino acid is G.

In certain aspects of any of the provided immunogens, the immunogen lacks the mucin like domain (MLD) of the filovirus GP1 subunit.

In certain aspects the disclosure further provides an immunogen that includes a filovirus spike glycoprotein (GP) or immunogenic fragment thereof, where the filovirus GP includes the GP head domain or an immunogenic fragment thereof, the GP base domain or an immunogenic fragment thereof, and the GP internal fusion loop domain or an immunogenic fragment thereof, wherein the GP comprises one or more single amino acid substitutions relative to the corresponding wild-type filovirus GP amino acid sequence, and wherein the one or more amino acid substitutions increases immunogenicity of the immunogen against the corresponding wild-type filovirus GP internal fusion loop domain, and/or broadens the cross-reactive immunogenicity of the immunogen against other filovirus species or strains, e.g., EBOV, SUDV, BDBV, RESTV, TAFV, MARV, any strain thereof, or a combination thereof. In certain aspects, the wild-type filovirus is a wild-type Ebola virus (EBOV), and the GP amino acid substitution(s) include an amino acid substitution at a position corresponding to N40, T42, D192, F193, F194, or Q595 of the wild-type Ebola virus (EBOV) GP, or a combination thereof, e.g., at a position corresponding to N40, D192, F193, or F194 of the wild-type Ebola virus (EBOV) GP, or a combination thereof. In certain embodiments, the immunogen further comprising any one or more GP amino acid substitutions disclosed elsewhere herein. In certain aspects, the wild-type Ebola virus is EBOV strain Mayinga-76. In certain aspects: the wild-type amino acid is substituted with an alanine (A) residue, except where the wild-type amino acid is A; the wild-type amino acid is A and the wild-type amino acid is substituted with a serine (S) residue; and/or the wild-type amino acid is substituted with a glycine (G) residue, except where the wild-type amino acid is G. In certain aspects, the immunogen lacks the mucin like domain (MLD) of the filovirus GP1 subunit.

In certain aspects the disclosure further provides for an immunogen that includes a GP filovirus spike glycoprotein (GP) or immunogenic fragment thereof, wherein the immunogen is a cleaved GP ($GP_{CL}$) lacking the filovirus GP1 subunit MLD and glycan cap. In certain aspects, the $GP_{CL}$ comprises one or more GP amino acid substitutions of an immunogen of any one or more GP amino acid substitutions disclosed elsewhere herein. In certain aspects, the wild-type Ebola virus is EBOV strain Mayinga-76. In certain aspects: the wild-type amino acid is substituted with an alanine (A) residue, except where the wild-type amino acid is A; the wild-type amino acid is A and the wild-type amino acid is substituted with a serine (S) residue; and/or the wild-type amino acid is substituted with a glycine (G) residue, except where the wild-type amino acid is G.

The disclosure further provides a method of increasing immunogenicity of and/or of broadening the cross-reactive immunogenicity of an immunogen that includes a filovirus GP or immunogenic fragment thereof, where the method includes using an immunogen provided herein and/or making substitutions as described for the immunogens provided herein.

The disclosure further provides a method of masking an immunodominant epitope in a immunogen that includes a filovirus GP or a fragment thereof where the method includes making appropriate substitutions as described for the immunogens provided herein.

The disclosure further provides a composition comprising an immunogen as provided herein, and an adjuvant. In certain aspects, the immunogen is incorporated into a filovirus virus-like particle (VLP). In certain aspects, the filovirus VLP can further include a filovirus a filovirus VP40, a filovirus nucleoprotein (NP), and/or filovirus VP24.

The disclosure further provides an isolated polynucleotide that includes a nucleic acid encoding an immunogen or fragment thereof as provided herein, or a subunit thereof. Further provided is a vector that includes the provided polynucleotide and a host cell that includes the provided polynucleotide or the provided vector.

The disclosure further provides a method of making an immunogen as provided herein, where the method includes culturing the provided host cell and recovering the immunogen.

BRIEF DESCRIPTION OF THE DRAWINGS/FIGURES

FIG. 1 shows the trimeric structure of EBOV GP lacking the mucin like domain (MLD). The MLD is modeled on the structure as large gray balls. The different regions of the GP, the glycan cap, the core GP1 in the head domain, the base consisting of the GP2 and the N-terminus of GP1. The base binder KZ52 structure is also shown. The positions of the cross-reactive/cross neutralizing antibodies are marked as small black circles on the head domain of the trimeric GP, as opposed to the epitopes for KZ52, 2G4, and 4G7 that are located within the base and marked with white circles. The epitope for the fusion loop binding antibody CA45 is shown as a star.

FIG. 2A shows binding of antibodies to the EBOV GP library. Shown are the binding values, relative to binding with wild-type GP, of all EBOV GP single alanine substitution library mutants with EBOV specific antibody KZ52 (A).

FIG. 2B shows binding of antibodies to the EBOV GP library. Shown are the binding values, relative to binding with wild-type GP, of all EBOV GP single alanine substitution library mutants with pan-ebolavirus antibody FVM04 (B).

FIG. 2C shows binding of antibodies to the EBOV GP library. Shown are the binding values, relative to binding with wild-type GP, of all EBOV GP single alanine substitution library mutants with pan-ebolavirus antibody m8C4 (C).

FIG. 2D shows binding of antibodies to the EBOV GP library. Shown are the binding values, relative to binding with wild-type GP, of all EBOV GP single alanine substitution library mutants with pan-ebolavirus antibody FVM09 (D).

FIG. 2E shows binding of antibodies to the EBOV GP library. Shown are the binding values, relative to binding with wild-type GP, of all EBOV GP single alanine substitution library mutants with pan-ebolavirus antibody FVM17 (E).

FIG. 2F shows binding of antibodies to the EBOV GP library. Shown are the binding values, relative to binding with wild-type GP, of all EBOV GP single alanine substitution library mutants with pan-ebolavirus antibody FVM20 (F).

FIG. 3A shows epitope mapping of FVM04 mAb. (A) The shotgun mutagenesis library of EBOV GP was tested for immunoreactivity with mAb FVM04. Clones were initially identified to be critical for mAb FVM04 binding with reactivity of <30% relative to that of wild-type EBOV GP yet >65% reactivity for a control MAb, and were verified using algorithms described elsewhere (U.S. patent application 61/938,894, and Davidson and Doranz, 2014 Immunology 143:13-20).

FIG. 3B shows epitope mapping of FVM04 mAb. (B) Mutation of three individual residues reduced FVM04 binding (white bars) but had little effect on the binding of other mAbs FVM02 and FVM09; hatched and gray bars, respectively). Bars represent the mean and range of at least two replicate data points.

FIG. 3C: FIG. 3C shows epitope mapping of FVM04 mAb. (C) Sequence homology between filoviruses within the RBS crest region containing putative FVM04 epitope (EBOV GP, SEQ ID NO: 17; SUDV GP, SEQ ID NO: 18; BDBV GP, SEQ ID NO: 19; RESTV GP: SEQ ID NO: 20; TAFV GP, SEQ ID NO: 21, and MARV GP, SEQ ID NO: 22). Identical sequences among ebolavirus species and between ebolavirus and marburgvirus are shown in bold. The FVM04 binding site is boxed.

Figure 4:
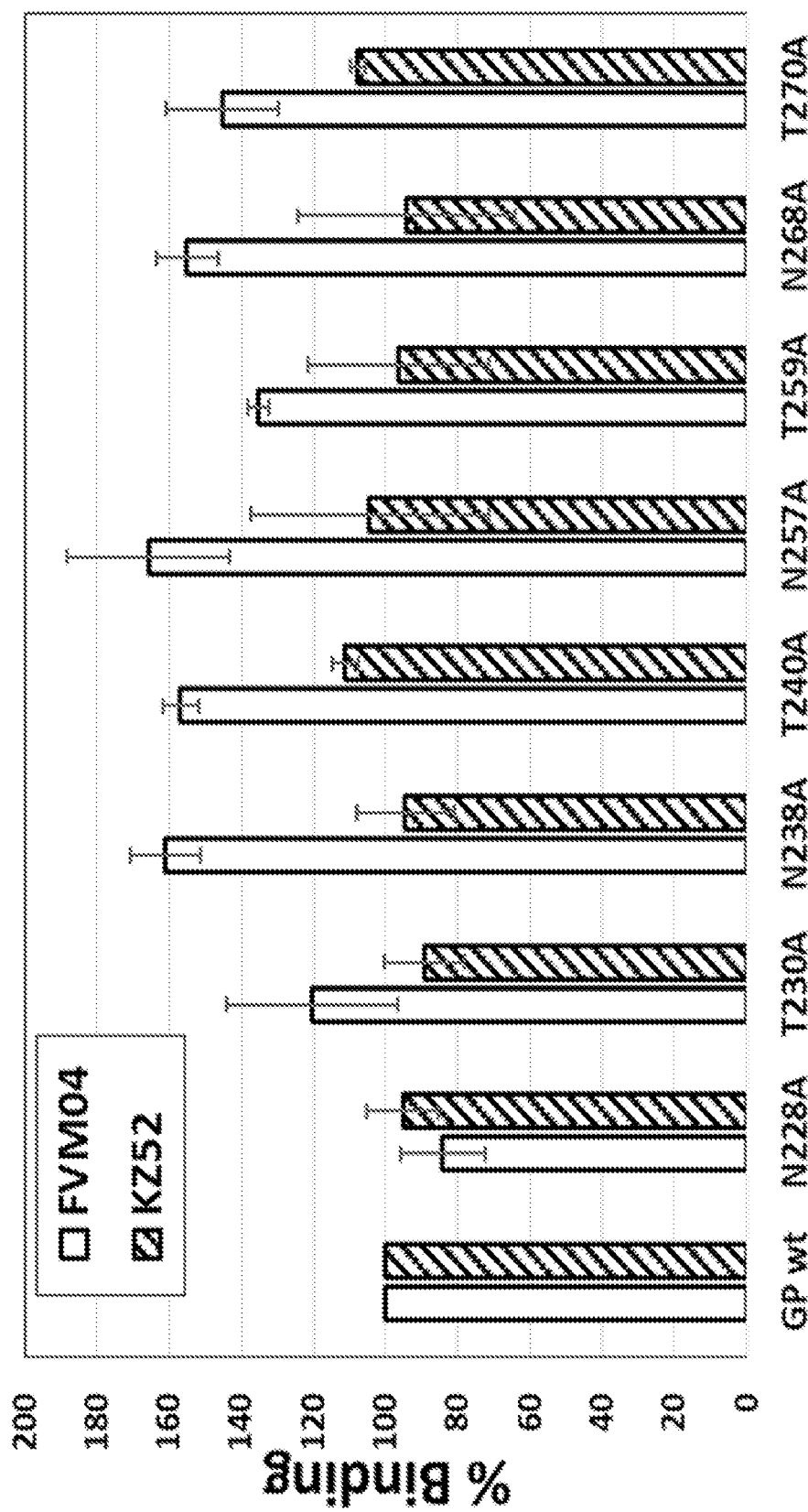

FIG. 4 shows that mutation of glycan cap glycosylation sites N238, N257, and N268 enhances binding of FVM04 to EBOV GP. Relative bindings of FVM04 and KZ52 to the mutants affecting the four glycan cap glycosylation sites are shown as percent of binding of the same antibody to wild-type (wt) GP expressed on 293T cells and determined by flow cytometry.

FIG. 5A shows that residues that modify binding of mAbs FVM09 (A). Alanine scan mutagenesis analysis of binding of pan-ebolavirus mAbs FVM09. Mutations of GP residues with significant reduction or increase in binding of the two antibodies to the respective GP mutant are shown.

FIG. 5B shows that residues that modify binding of m8C4 (B). Alanine scan mutagenesis analysis of binding of pan-ebolavirus mAbs m8C4. Mutations of GP residues with significant reduction or increase in binding of the two antibodies to the respective GP mutant are shown.

FIG. 6A shows the neutralization of VSV pseudotyped with EBOV GPwt (wild-type) in comparison to EBOVGP-AAA (F290A/W291A/E292A) mediated by m8C4 (A).

FIG. 6B shows the neutralization of VSV pseudotyped with EBOV GPwt (wild-type) in comparison to EBOVGP-AAA (F290A/W291A/E292A) mediated by KZ52 (B).

Figure 7A:
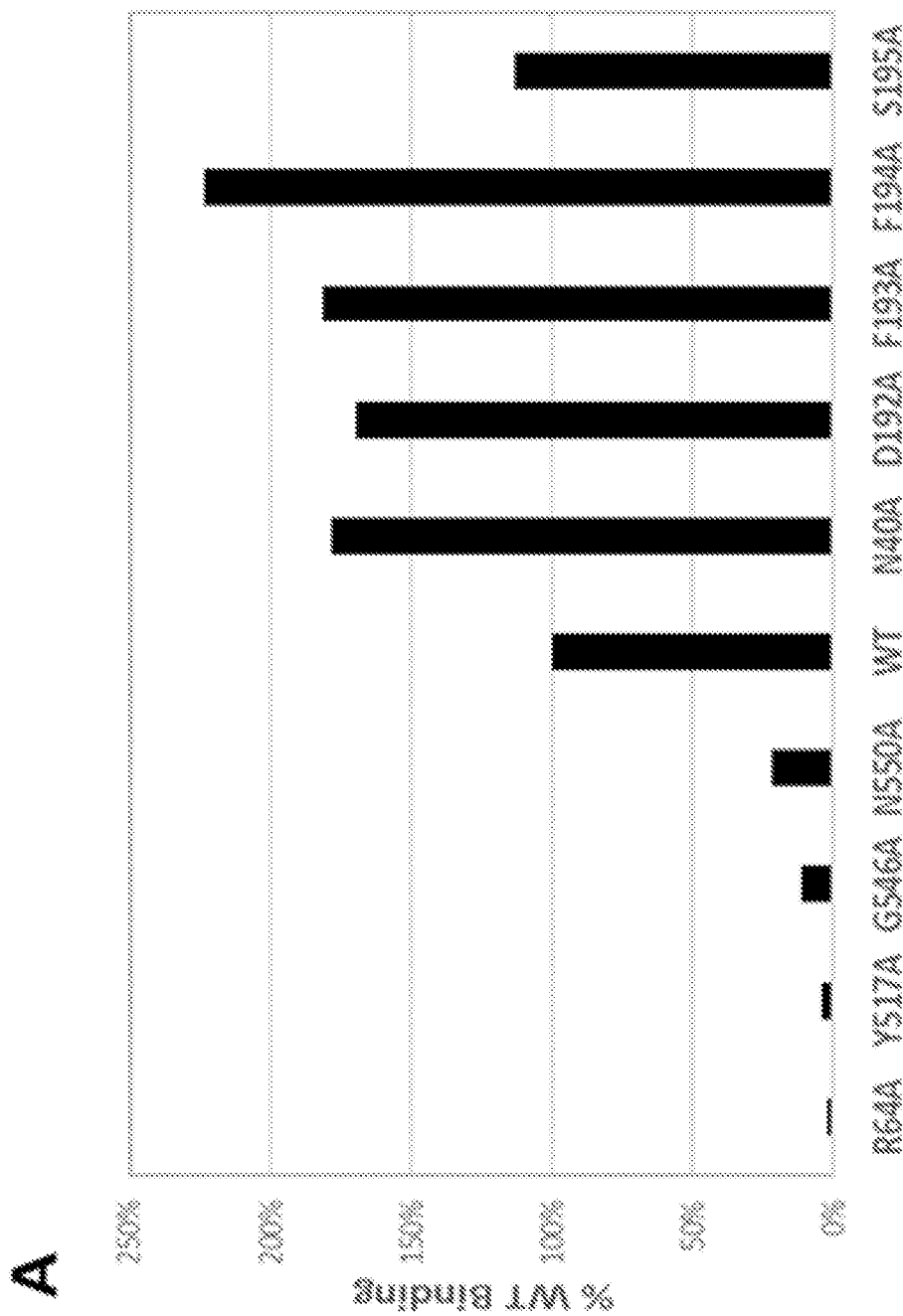

FIG. 7A shows the binding of specific mutants of EBOV GP to pan-ebolavirus antibody CA45. Mutation of GP residues R64, Y517, G546, and N550 drastically reduced CA45 binding, alanine substitution of N40, D192, F193, and F194, but not S195, increased GP binding to CA45.

Figure 7B:
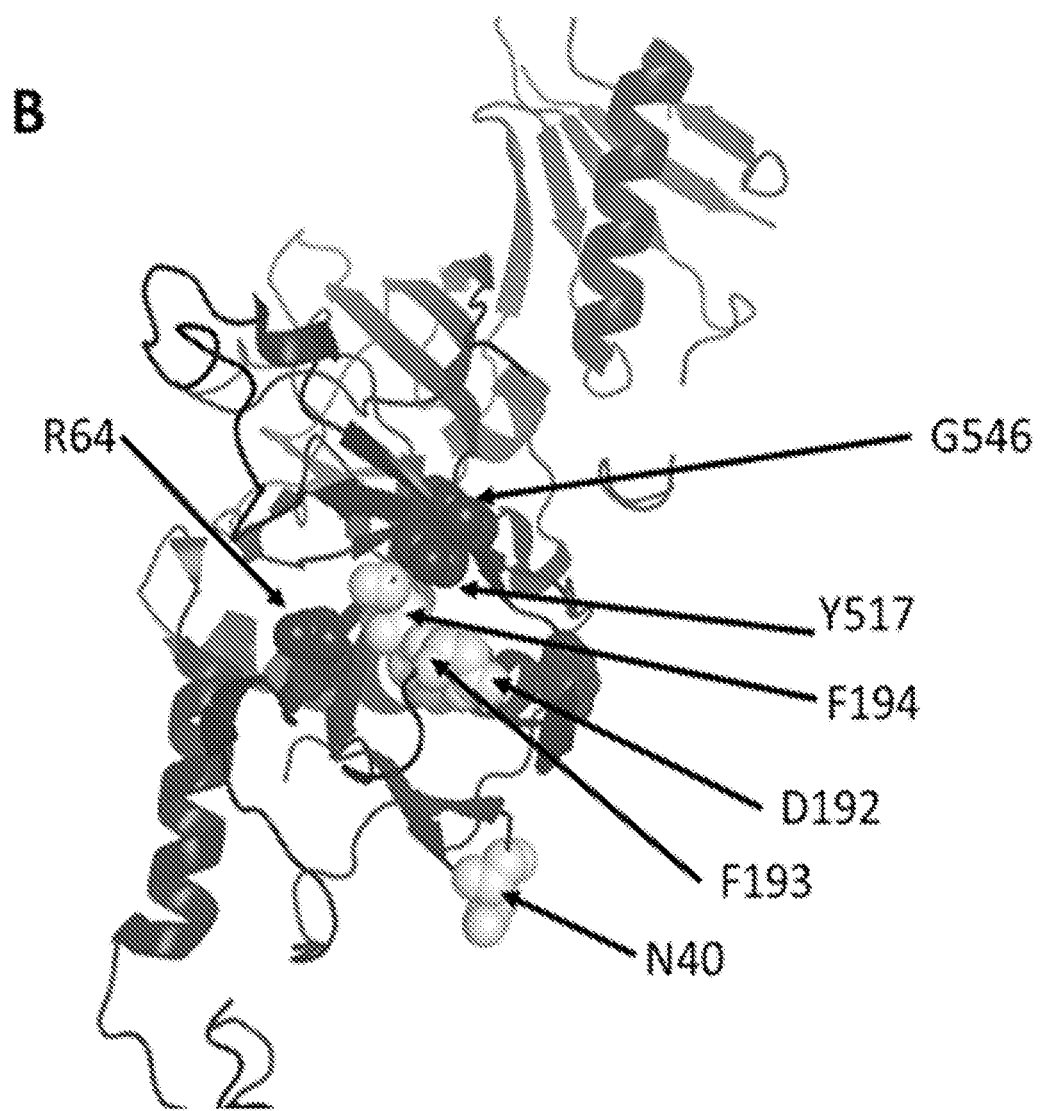

FIG. 7B shows the position of the CA45 epitope residues and enhancing residues on the structure of an EBOV GP monomer. GP1 is shown in light gray, GP2 in dark grey, the epitope residues in black spheres and the enhancing residues in white spheres.

Figure 8:
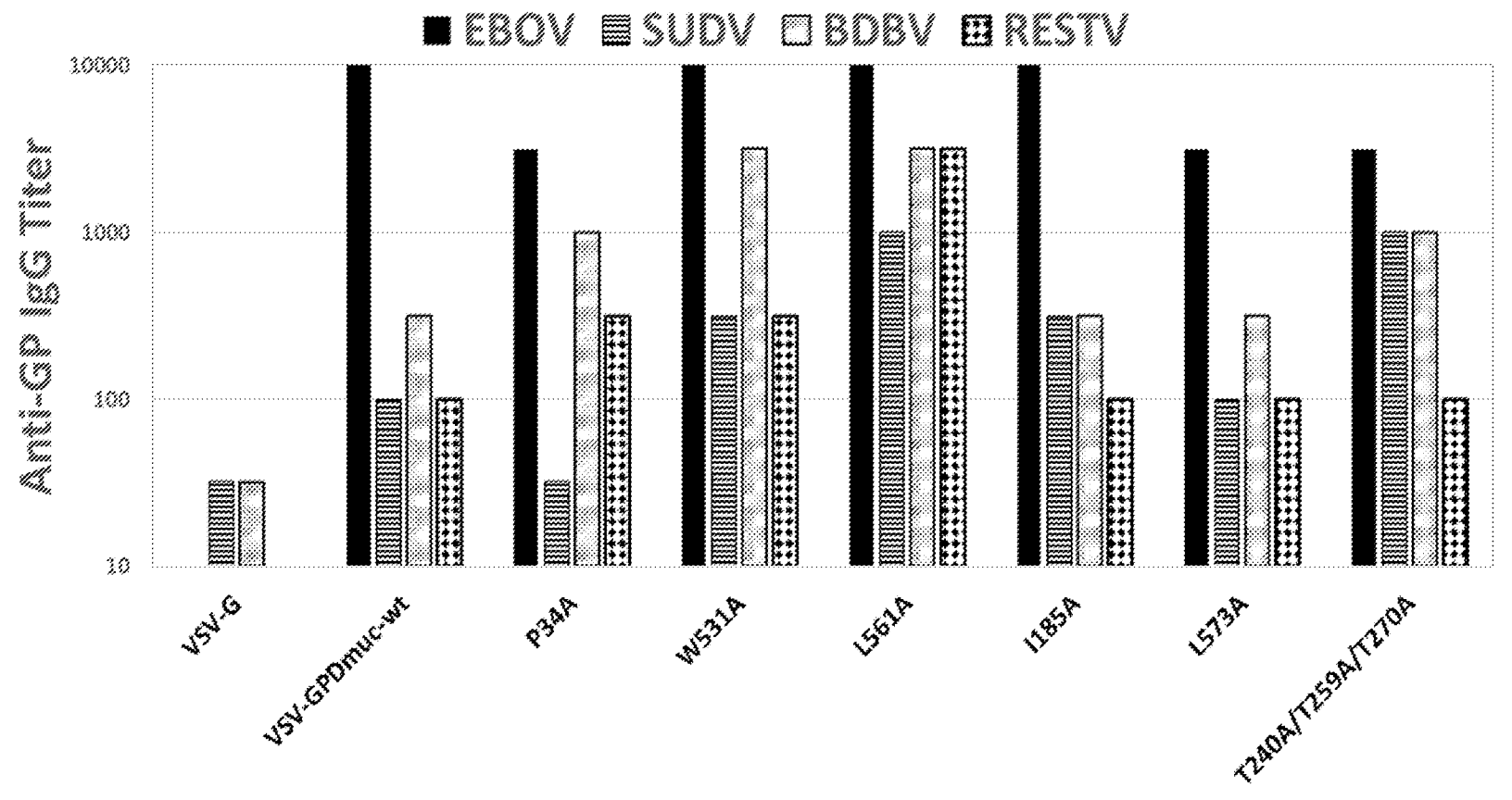

FIG. 8 shows the breadth of antibody response elicited in mice by VSV-GPΔmuc wild type or the indicated mutants. VSV-G was used as negative control. Y-axis shows $EC_{50}$ dilution titer against the different viruses listed in the graph legend.

DETAILED DESCRIPTION

Definitions

The term "a" or "an" entity refers to one or more of that entity; for example, "a polypeptide subunit" is understood to represent one or more polypeptide subunits. As such, the terms "a" (or "an"), "one or more," and "at least one" can be used interchangeably herein.

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

It is understood that wherever aspects are described herein with the language "comprising," otherwise analogous aspects described in terms of "consisting of" and/or "consisting essentially of" are also provided.

All methods described herein can be performed in any suitable order unless otherwise indicated herein. No language or terminology in this specification should be construed as indicating any non-claimed element as essential or critical.

The headings provided herein are not limitations of the various aspects or aspects of the disclosure, which can be had by reference to the specification as a whole.

Unless defined otherwise, technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Système International de Unites (SI) accepted form. Numeric ranges are inclusive of the numbers defining the range. Unless otherwise indicated, amino acid sequences are written left to right in amino to carboxy orientation. The headings provided herein are not limitations of the various aspects or aspects of the disclosure, which can be had by reference to the specification as a whole. Accordingly, the terms defined immediately below are more fully defined by reference to the specification in its entirety.

As used herein, the term "non-naturally occurring" substance, composition, entity, and/or any combination of substances, compositions, or entities, or any grammatical variants thereof, is a conditional term that explicitly excludes, but only excludes, those forms of the substance, composition, entity, and/or any combination of substances, compositions, or entities that are well-understood by persons of ordinary skill in the art as being "naturally-occurring," or that are, or could be at any time, determined or interpreted by a judge or an administrative or judicial body to be, "naturally-occurring."

As used herein, the term "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids are included within the definition of "polypeptide," and the term "polypeptide" can be used instead of, or interchangeably with any of these terms. The term "polypeptide" is also intended to refer to the products of post-expression modifications of the polypeptide, including without limitation glycosylation, acetylation, phosphorylation, amidation, derivatization by known protecting/blocking groups, proteolytic cleavage, or modification by non-standard amino acids. A polypeptide can be derived from a natural biological source or produced by recombinant technology, but is not necessarily translated from a designated nucleic acid sequence. It can be generated in any manner, including by chemical synthesis.

A "protein" as used herein can refer to a single polypeptide, i.e., a single amino acid chain as defined above, but can also refer to two or more polypeptides that are associated, e.g., by disulfide bonds, hydrogen bonds, or hydrophobic interactions, to produce a multimeric protein. As used herein, the term "glycoprotein" refers to a protein coupled to at least one carbohydrate moiety that is attached to the protein via an oxygen-containing or a nitrogen-containing side chain of an amino acid residue, e.g., a serine residue or an asparagine residue.

By an "isolated" polypeptide or a fragment, variant, or derivative thereof is intended a polypeptide that is not in its natural milieu. No particular level of purification is required. For example, an isolated polypeptide can be removed from its native or natural environment. Recombinantly produced polypeptides and proteins expressed in host cells are considered isolated as disclosed herein, as are recombinant polypeptides that have been separated, fractionated, or partially or substantially purified by any suitable technique.

As used herein, the term "non-naturally occurring" polypeptide, or any grammatical variants thereof, is a conditional term that explicitly excludes, but only excludes, those forms of the polypeptide that are well-understood by persons of ordinary skill in the art as being "naturally-occurring," or that are, or could be at any time, determined or interpreted by a judge or an administrative or judicial body to be, "naturally-occurring."

Other polypeptides disclosed herein are fragments, derivatives, analogs, or variants of the foregoing polypeptides, and any combination thereof. The terms "fragment," "variant," "derivative" and "analog" when referring to polypeptide subunit or multimeric protein as disclosed herein can include any polypeptide or protein that retain at least some of the activities of the complete polypeptide or protein (for example retain at least some of the antibody-binding properties), but which is structurally different. Fragments of polypeptides include, for example, proteolytic fragments, as well as deletion fragments. Variants include fragments as described above, and also polypeptides with altered amino acid sequences due to amino acid substitutions, deletions, or insertions. Variants can occur spontaneously or be intentionally constructed. Intentionally constructed variants can be produced using art-known mutagenesis techniques. Variant polypeptides can comprise conservative or non-conservative amino acid substitutions, deletions or additions. Derivatives are polypeptides that have been altered so as to exhibit additional features not found on the native polypeptide. Examples include fusion proteins. Variant polypeptides can also be referred to herein as "polypeptide analogs." As used herein a "derivative" refers to a subject polypeptide having one or more amino acids chemically derivatized by reaction of a functional side group. Also included as "derivatives" are those peptides that contain one or more standard or synthetic amino acid derivatives of the twenty standard amino acids. For example, 4-hydroxyproline can be substituted for proline; 5-hydroxylysine can be substituted for lysine; 3-methylhistidine can be substituted for histidine; homoserine can be substituted for serine; and ornithine can be substituted for lysine.

As used herein, a "single amino acid substitution" means replacing an amino acid residue in a polypeptide sequence with a different amino acid residue (such as replacing the native residue in a wild-type sequence with a non-native amino acid), unless otherwise specified. Also encompassed by the disclosure are a "single amino acid deletion" and/or a "single amino acid insertion."

A "conservative amino acid substitution" is one in which one amino acid is replaced with another amino acid having a similar side chain. Families of amino acids having similar side chains have been defined in the art, including basic side chains (e.g., lysine, arginine, histidine), acidic side chains (e.g., aspartic acid, glutamic acid), uncharged polar side chains (e.g., asparagine, glutamine, serine, threonine, tyrosine, cysteine), nonpolar side chains (e.g., glycine, alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). For example, substitution of a phenylalanine for a tyrosine is a conservative substitution. Methods of identifying nucleotide and amino acid conservative substitutions which do not eliminate protein activity are well-known in the art (see, e.g., Brummell et al., *Biochem.* 32: 1180-1 187 (1993); Kobayashi et al., *Protein Eng.* 12(10):879-884 (1999); and Burks et al., *Proc. Natl. Acad. Sci. USA* 94: 412-417 (1997)).

Disclosed herein are certain antibodies, or antigen-binding fragments, variants, or derivatives thereof. Unless specifically referring to full-sized antibodies such as naturally-occurring antibodies, the term "antibody" encompasses full-sized antibodies as well as antigen-binding fragments, variants, analogs, or derivatives of such antibodies, e.g., naturally-occurring antibody or immunoglobulin molecules or engineered antibody molecules or fragments that bind antigen in a manner similar to antibody molecules.

As described further herein, an antibody or fragment thereof can comprise one or more "binding domains." As used herein, a "binding domain" or "antigen binding domain" is a two- or three-dimensional structure, e.g., a polypeptide structure that cans specifically bind a given antigenic determinant, e.g., the region formed by the heavy and light chain variable regions of an antibody or fragment thereof.

The terms "antibody" and "immunoglobulin" can be used interchangeably herein. An antibody (or a fragment, variant, or derivative thereof as disclosed herein comprises at least the variable domain of a heavy chain and at least the variable domains of a heavy chain and a light chain. Basic immunoglobulin structures in vertebrate systems are relatively well understood. See, e.g., Harlow et al., Antibodies: A Laboratory Manual, (Cold Spring Harbor Laboratory Press, 2nd ed. 1988).

Antibodies or antigen-binding fragments, variants, or derivatives thereof include, but are not limited to, polyclonal, monoclonal, human, humanized, or chimeric antibodies, single chain antibodies, epitope-binding fragments, e.g., Fab, Fab' and $F(ab')_2$, Fd, Fvs, single-chain Fvs (scFv), single-chain antibodies, disulfide-linked Fvs (sdFv), fragments comprising either a VL or VH domain, fragments produced by a Fab expression library. ScFv molecules are known in the art and are described, e.g., in U.S. Pat. No. 5,892,019. Immunoglobulin or antibody molecules encompassed by this disclosure can be of any type (e.g., IgG, IgE, IgM, IgD, IgA, and IgY), class (e.g., IgG1, IgG2, IgG3, IgG4, IgA1 and IgA2) or subclass of immunoglobulin molecule.

By "specifically binds," it is meant that an antibody or fragment, variant, or derivative thereof binds to an epitope via its antigen binding domain, and that the binding entails some complementarity between the antigen binding domain and the epitope. According to this definition, an antibody or fragment thereof is said to "specifically bind" to an epitope when it binds to that epitope, via its antigen-binding domain more readily than it would bind to a random, unrelated epitope. The term "specificity" is used herein to qualify the relative affinity by which a certain antibody or fragment thereof binds to a certain epitope. For example, antibody or fragment thereof "A" can be deemed to have a higher specificity for a given epitope than antibody or fragment thereof "B" or antibody or fragment thereof "A" can be said to bind to epitope "C" with a higher specificity than it has for related epitope "D."

As used herein, the term "affinity" refers to a measure of the strength of the binding of an individual epitope with the CDR of an immunoglobulin molecule. See, e.g., Harlow et al., Antibodies: A Laboratory Manual, (Cold Spring Harbor Laboratory Press, 2nd ed. 1988) at pages 27-28. As used herein, the term "avidity" refers to the overall stability of the complex between a population of immunoglobulins and an antigen, that is, the functional combining strength of an immunoglobulin mixture with the antigen. See, e.g., Harlow at pages 29-34. Avidity is related to both the affinity of individual immunoglobulin molecules in the population with specific epitopes, and also the valencies of the immunoglobulins and the antigen. For example, the interaction between a bivalent monoclonal antibody and an antigen with a highly repeating epitope structure, such as a polymer, would be one of high avidity. An interaction between a between a bivalent monoclonal antibody with a receptor present at a high density on a cell surface would also be of high avidity.

The term "polynucleotide" is intended to encompass a singular nucleic acid as well as plural nucleic acids, and refers to an isolated nucleic acid molecule or construct, e.g., messenger RNA (mRNA) or plasmid DNA (pDNA). A polynucleotide can comprise a conventional phosphodiester bond or a non-conventional bond (e.g., an amide bond, such as found in peptide nucleic acids (PNA)). The term "nucleic acid" refers to any one or more nucleic acid segments, e.g., DNA or RNA fragments, present in a polynucleotide. By "isolated" nucleic acid or polynucleotide is intended a nucleic acid molecule, DNA or RNA, which has been removed from its native environment. For example, a recombinant polynucleotide encoding a polypeptide subunit contained in a vector is considered isolated as disclosed herein. Further examples of an isolated polynucleotide include recombinant polynucleotides maintained in heterologous host cells or purified (partially or substantially) polynucleotides in solution. Isolated RNA molecules include in vivo or in vitro RNA transcripts of polynucleotides. Isolated polynucleotides or nucleic acids further include such molecules produced synthetically. In addition, polynucleotide or a nucleic acid can be or can include a regulatory element such as a promoter, ribosome binding site, or a transcription terminator.

As used herein, a "non-naturally occurring" polynucleotide, or any grammatical variants thereof, is a conditional definition that explicitly excludes, but only excludes, those forms of the polynucleotide that are well-understood by persons of ordinary skill in the art as being "naturally-occurring," or that are, or that could be at any time, determined or interpreted by a judge or an administrative or judicial body to be, "naturally-occurring."

As used herein, a "coding region" is a portion of nucleic acid comprising codons translated into amino acids. Although a "stop codon" (TAG, TGA, or TAA) is not translated into an amino acid, it can be considered to be part of a coding region, but any flanking sequences, for example promoters, ribosome binding sites, transcriptional terminators, introns, and the like, are not part of a coding region. Two or more coding regions can be present in a single polynucleotide construct, e.g., on a single vector, or in separate polynucleotide constructs, e.g., on separate (different) vectors. Furthermore, any vector can contain a single coding region, or can comprise two or more coding regions, e.g., a single vector can separately encode an immunoglobulin heavy chain variable region and an immunoglobulin light chain variable region. In addition, a vector, polynucleotide, or nucleic acid can encode heterologous coding regions, either fused or unfused to a nucleic acid encoding a polypeptide subunit or fusion protein as provided herein. Heterologous coding regions include without limitation specialized elements or motifs, such as a secretory signal peptide or a heterologous functional domain.

In certain embodiments, the polynucleotide or nucleic acid is DNA. In the case of DNA, a polynucleotide comprising a nucleic acid that encodes a polypeptide normally can include a promoter and/or other transcription or translation control elements operably associated with one or more coding regions. An operable association or linkage can be when a coding region for a gene product, e.g., a polypeptide, can be associated with one or more regulatory sequences in such a way as to place expression of the gene product under the influence or control of the regulatory sequence(s). Two DNA fragments (such as a polypeptide coding region and a promoter associated therewith) can be "operably associated" or "operably linked" if induction of promoter function results in the transcription of mRNA encoding the desired gene product and if the nature of the linkage between the two DNA fragments does not interfere with the ability of the expression regulatory sequences to direct the expression of the gene product or interfere with the ability of the DNA template to be transcribed. Thus, a promoter region would be operably associated with a nucleic acid encoding a polypeptide if the promoter was capable of effecting transcription of that nucleic acid. The promoter can be a cell-specific promoter that directs substantial transcription of the DNA only in predetermined cells. Other transcription control elements, besides a promoter, for example enhancers, operators, repressors, and transcription termination signals, can be operably associated with the polynucleotide to direct cell-specific transcription. Suitable promoters and other transcription control regions are disclosed herein.

A variety of transcription control regions are known to those skilled in the art. These include, without limitation, transcription control regions that function in vertebrate cells, such as, but not limited to, promoter and enhancer segments from cytomegaloviruses (the immediate early promoter, in conjunction with intron-A), simian virus 40 (the early promoter), and retroviruses (such as Rous sarcoma virus). Other transcription control regions include those derived from vertebrate genes such as actin, heat shock protein, bovine growth hormone and rabbit β-globin, as well as other sequences capable of controlling gene expression in eukaryotic cells. Additional suitable transcription control regions include tissue-specific promoters and enhancers as well as lymphokine-inducible promoters (e.g., promoters inducible by interferons or interleukins).

Similarly, a variety of translation control elements are known to those of ordinary skill in the art. These include, but are not limited to ribosome binding sites, translation initiation and termination codons, and elements derived from picornaviruses (particularly an internal ribosome entry site, or IRES, also referred to as a CITE sequence).

In other embodiments, a polynucleotide can be RNA, for example, in the form of messenger RNA (mRNA).

Polynucleotide and nucleic acid coding regions can be associated with additional coding regions which encode secretory or signal peptides, which direct the secretion of a polypeptide encoded by a polynucleotide as disclosed herein. According to the signal hypothesis, proteins secreted by mammalian cells have a signal peptide or secretory leader sequence which is cleaved from the mature protein once export of the growing protein chain across the rough endoplasmic reticulum has been initiated. Those of ordinary skill in the art are aware that polypeptides secreted by vertebrate cells generally have a signal peptide fused to the N-terminus of the polypeptide, which is cleaved from the complete or "full length" polypeptide to produce a secreted or "mature" form of the polypeptide. In certain embodiments, the native signal peptide is used, or a functional derivative of that sequence that retains the ability to direct the secretion of the polypeptide that is operably associated with it. Alternatively, a heterologous mammalian signal peptide, or a functional derivative thereof, can be used. For example, the wild-type leader sequence can be substituted with the leader sequence of human tissue plasminogen activator (TPA) or mouse β-glucuronidase.

A "vector" is nucleic acid molecule as introduced into a host cell, thereby producing a transformed host cell. A vector can include nucleic acid sequences that permit it to replicate in a host cell, such as an origin of replication. A vector can also include one or more selectable marker gene and other genetic elements known in the art. Illustrative types of vectors include plasmids, phages, viruses and retroviruses.

A "transformed" cell, or a "host" cell, is a cell into which a nucleic acid molecule has been introduced by molecular biology techniques. As used herein, the term transformation encompasses those techniques by which a nucleic acid molecule can be introduced into such a cell, including transfection with viral vectors, transformation with plasmid vectors, and introduction of naked DNA by electroporation, lipofection, and particle gun acceleration. A transformed cell or a host cell can be a bacterial cell or a eukaryotic cell.

The term "expression" as used herein refers to a process by which a gene produces a biochemical, for example, a polypeptide. The process includes any manifestation of the functional presence of the gene within the cell including, without limitation, gene knockdown as well as both transient expression and stable expression. It includes without limitation transcription of the gene into messenger RNA (mRNA), and the translation of such mRNA into polypeptide(s). If the final desired product is a biochemical, expression includes the creation of that biochemical and any precursors. Expression of a gene produces a "gene product." As used herein, a gene product can be either a nucleic acid, e.g., a messenger RNA produced by transcription of a gene, or a polypeptide that is translated from a transcript. Gene products described herein further include nucleic acids with post transcriptional modifications, e.g., polyadenylation, or polypeptides with post translational modifications, e.g., methylation, glycosylation, the addition of lipids, association with other protein subunits, proteolytic cleavage, and the like.

As used herein the terms "treat," "treatment," or "treatment of" (e.g., in the phrase "treating a subject") refers to reducing the potential for disease pathology, reducing the occurrence of disease symptoms, e.g., to an extent that the subject has a longer survival rate or reduced discomfort. For example, treating can refer to the ability of a therapy when administered to a subject, to reduce disease symptoms, signs, or causes. Treating also refers to mitigating or decreasing at least one clinical symptom and/or inhibition or delay in the progression of the condition and/or prevention or delay of the onset of a disease or illness. The term "protection" and related grammatical terms, when used in the context of the ability of a therapeutic agent to affect the course of an infectious disease refers to any protective effect observed in comparison to a control agent. For example if two groups of animals are challenged with an infectious agent, e.g., a lethal dose of EBOV, and one group of animals is administered the therapeutic agent while the other group is administered a control, if a statistically significant number of animals in the therapeutic group survive relative to the number of survivors in the control group, a protective effect is observed. "Protection" can be, but does not have to be, 100%.

By "subject" or "individual" or "animal" or "patient" or "mammal," is meant any subject, particularly a mammalian subject, for whom diagnosis, prognosis, or therapy is desired. Mammalian subjects include humans, domestic animals, farm animals, sports animals, and zoo animals, including, e.g., humans, non-human primates, dogs, cats, guinea pigs, rabbits, rats, mice, horses, cattle, bears, and so on.

The term "pharmaceutical composition" refers to a preparation that is in such form as to permit the biological activity of the active ingredient to be effective, and that contains no additional components that are unacceptably toxic to a subject to which the composition would be administered. Such composition can be sterile.

By a "filovirus" is meant a virus belonging to the family Filoviridae. Exemplary filoviruses are Lloviu virus (LLOV), Bundibugyo virus (BDBV), Reston virus (RESTV), Sudan virus (SUDV), Tai Forest virus (TAFV), Ebola virus (EBOV), Marburg virus (MARV), and Ravn virus (RAVV). In certain embodiments, a filovirus is selected from the group consisting of EBOV, SUDV, BDBV, RESTV, TAFV, MARV, and a combination thereof.

The virions of filoviruses contain seven proteins which include a surface glycoprotein (GP), a nucleoprotein (NP), an RNA-dependent RNA polymerase (L), and four virion structural proteins (VP24, VP30, VP35, and VP40).

The term "epitope," as used herein, refers to portions of a polypeptide (or other biological molecule such as a carbohydrate) having antigenic or immunogenic activity in an animal, for example a mammal, for example, a human. An "immunogen" or an "immunogenic epitope," as used herein, is defined as a portion of a protein that elicits an immune response in an animal, as determined by any method known in the art. The term "antigen," or "antigenic epitope," as used herein, is defined as a portion of a protein to which an antibody or T-cell receptor can immunospecifically bind its antigen as determined by any method well known in the art. Immunospecific binding excludes non-specific binding but does not exclude cross-reactivity with other antigens. Whereas all immunogenic epitopes are antigenic, antigenic epitopes need not be immunogenic. An "epitopic fragment" of a polypeptide antigen is a portion of the antigen that contains an epitope. An "epitopic fragment" can, but need not, contain amino acid sequence in addition to one or more epitopes.

By "vaccine," is meant a composition comprising an immunogen which, when inoculated into a mammal, has the effect of stimulating a cellular immune response comprising a T-cell response and/or a humoral immune response comprising a B-cell response generally resulting in antibody production. The T cell response can be a cytotoxic T-cell response directed against an organism that expresses the antigen. However, the induction of a T-cell response comprising other types of T cells by an immunogen disclosed herein is also contemplated. A B-cell response results in the production of antibody that binds to the antigen. The vaccine can serve to elicit an immune response in the mammal which serves to protect the mammal against a disease. The terms "vaccine," "immunogen," "immunogenic polypeptide," and the like may be used interchangeably. The term "vaccine" does not in any way connote that the composition is capable of fully preventing a disease in a vaccinated subject, or providing any specific or general level of protection against an infectious agent. In certain aspects a "vaccine" can be ineffective in certain subjects while inducing an immune response in other subjects.

By "subunit vaccine" is meant a vaccine produced from a specific protein subunit of a virus and thus having less risk of adverse reactions than whole virus vaccines. A subunit vaccine can be, for example, a soluble immunogenic polypeptide, or immunogenic fragment thereof, or the polypeptide or fragment (or two or more polypeptides) that can self-assemble as a multimer. The term "peptide vaccine" or "subunit vaccine" can also refer to a composition comprising one or more polypeptide subunits, which when administered to an animal are useful in stimulating an immune response against filovirus infection.

By "virus-like particle" or "VLP" is meant a non-infectious particle that resembles an infectious virus, e.g., in immune surveillance, but which lacks the genetic material to create new virus particles. VLPs can be used as immunogens or vaccines as described elsewhere herein. VLPs can include any combination of virus components provided that the VLP lacks the genetic machinery to self-replicate. In certain aspects, VLPs can be made by allowing self-assembly of a matrix or scaffold-like protein, e.g., a viral capsid protein, and can further include a viral envelope.

The term "viral vector" refers to a recombinant virus that can express a heterologous immunogen of interest. For example, a filovirus glycoprotein as described herein can be expressed in a recombinant virus, e.g., a vesicular stomatitis virus (VSV), a pox virus (e.g., a vaccinia virus), an adenovirus, a herpesvirus, or other recombinant virus, using techniques well established in the art.

As used herein, "cross-reactive" means the ability of an immunogen, e.g., an immunogenic polypeptide as provided herein, to elicit an immune response against two or more filovirus species or strains. For example, an immunogen with cross-reactive immunogenicity induces the production of antibodies capable of specifically binding to, recognizing, and/or neutralizing two or more heterologous filovirus species or strains.

As used herein, an "increase," "increased," "increasing," and the like of immunogenicity means that an immunogen as provided herein can provide an improved immune response against its original target (e.g., the wild-type filovirus from which the immunogen was derived) than the corresponding wild-type immunogen. For example, the immunogen can induce a more effective immune response (increased protection, increased potency, increased virus killing, increased induction of antibodies, increased T-cell immunity, etc.) than the corresponding wild-type immunogen. Likewise, an immunogen as provided herein can exhibit increased immunogenicity against a cross-reactive target (e.g., another filovirus species or strain).

As used herein, to "broaden, "broadened, "broadening," and the like of cross-reactive immunogenicity means that the immunogen as provided herein has a broader scope of cross-reactivity than the corresponding wild-type immunogen. For example, an immunogen as provided herein can induce an immune response against EBOV and SUDV strains, where the corresponding wild-type immunogen only induced an immune response against EBOV.

As used herein, "species specific" or "strain specific" when used in reference to an immunogen, e.g., an immunogenic polypeptide as provided herein, means that an immune response elicited by the immunogen is predominantly directed towards a single filovirus species (or a single filovirus strain) in comparison to multiple filovirus species or strains.

As used herein, "cross-protective" means the ability of an immunogen, e.g., an immunogenic polypeptide as provided herein, to elicit an immune response that provides at least some level of protection (e.g., preventing disease symptoms, reducing disease symptoms, or preventing death) against infection by two or more heterologous filovirus species or strains.

"Inducing specific immunity" as used herein refers to providing to a population or an individual the ability to direct an immune response against specific pathogens (e.g., filoviruses).

"Conferring protective immunity" as used herein refers to providing to a population or an individual the ability to generate an immune response to protect against a disease (e.g., hemorrhagic fever) caused by a pathogen (e.g., Ebola virus) such that the clinical manifestations, pathology, or symptoms of disease in a host are minimized, reduced, or prevented as compared to a non-treated host, or such that the rate at which infection, or clinical manifestations, pathology, or symptoms of disease appear within a population are reduced, as compared to a non-treated population.

In certain embodiments, an immunogen, e.g., an immunogenic polypeptide as provided herein, can be useful for inducing immunity against one, two, three, four, five or more filovirus species or strains. Such immunity can protect/treat an individual or a population with filovirus infection. The term "immune response" refers to any response by the immune system of an individual to an immune response inducing composition or other immunogenic compound. Exemplary immune responses include, but not limited to cellular as well as local and systemic humoral immunity, such as CTL responses, including antigen-specific induction of CD8+ CTLs, helper T-cell responses, including T-cell proliferative responses and cytokine release, and B-cell responses including, e.g., an antibody producing response. The term "inducing an immune response" or "eliciting an immune response" refers to administration of an immune response inducing composition or other immunogenic compound or a nucleic acid encoding the immune response inducing composition or other immunogenic compound, wherein an immune response is affected, i.e., stimulated, initiated or induced.

As used herein, the term "a filovirus-mediated disease" encompasses a condition which is a direct result of filovirus infection; and a condition which is an indirect result, e.g., a sequela, of a filovirus infection. An exemplary filovirus disease is hemorrhagic fever. Symptoms of hemorrhagic fever include, but are not limited to, fever, internal hemorrhaging, edema, organ failure, headache, malaise, myalgia, nausea, vomiting, bleeding of needle puncture sites, hematemesis, melena, petechiae, ecchymosis, maculopapular rash, disseminated intravascular coagulation, shock, jaundice, conjunctivitis, diarrhea, pharyngitis, convulsions, delirium, coma, oligura, epistaxis, and death.

As used herein, the term "adjuvant" is intended to encompass a substance or vehicle that non-specifically enhances the immune response to an antigen or immunogen. Adjuvants can include a suspension of minerals (such as alum, aluminum hydroxide, or phosphate) on which antigen is adsorbed; or water-in-oil emulsion in which antigen solution is emulsified in mineral oil (for example, Freund's incomplete adjuvant), sometimes with the inclusion of killed mycobacteria (Freund's complete adjuvant) to further enhance immunogenicity.

As used herein the term "engineered" includes manipulation of nucleic acid or polypeptide molecules by synthetic means (e.g. by recombinant techniques, in vitro peptide synthesis, by enzymatic or chemical coupling of peptides or some combination of these techniques).

As used here, CA45-like broadly neutralizing antibodies are antibodies that bind to the same or similar GP epitope as the CA45 antibody (U.S. Provisional Application No. 62/406,598), but are not limited to antibodies merely sharing similar sequence to the CA45 antibody.

As referred to herein, all residue numbers are based on Ebola virus GP (EBOV GP). Unless otherwise specified herein, reference to EBOV GP indicates wild-type protein amino acid sequences (e.g., SEQ ID NOs 1, 3, and 5). When specified, the EBOV GP can be a mucin-deleted version (delta ($\Delta$) mucin) (e.g., SEQ ID NOs 2, 4, and 6).

Cross-Reactive Monoclonal Antibodies

The most divergent region of the filovirus GP molecule is the mucin like domain (MLD). The MLD can be deleted (delta ($\Delta$) mucin) to focus the immune response to the more conserved regions of the GP. Using immunization of mice and macaques with a prime boost strategy involving filovirus virus like particles (VLPs) and soluble glycoproteins lacking the MLD, several cross-reactive antibodies have been generated (Keck, et al., 2016, *J Virol*, 90:279-291; Holtsberg, et al., 2016, *J Virol*, 90:266-278). Analysis of the binding pattern of these cross-reactive monoclonal antibodies showed that nearly all of them bind to the top of the GP trimer (Keck, et al., 2016, *J Virol*, 90:279-291; Holtsberg, et al., 2016, *J Virol*, 90:266-278), in contrast to the strain specific neutralizing antibodies KZ52 and 2G4 that bind to the base of the chalice (Lee, et al., 2008, Nature, 454 (7201): 177-182; Murin, et al, 2014, *Proc Natl Acad Sci USA*, 111(48):17182-7).

Structure-Based Pan Filovirus Vaccine Design

Provided herein are methods of incorporating substitutions of specified residues into a filovirus GP in order to increase immunogenicity and/or broaden the cross-reactivity against other filovirus species or strain. Also provided herein are mutant filovirus GPs comprising such substitutions. In certain embodiments, the filovirus GP is an EBOV GP. In certain embodiments, the EBOV is EBOV strain Mayinga-76. In certain embodiments, the other filovirus species or strain comprises EBOV, SUDV, BDBV, RESTV, TAFV, MARV, any strain thereof, or a combination thereof.

The substitutions can be incorporated into the filovirus GP in a variety of vaccine platforms, including, but not limited to a recombinant protein or subunit vaccine, a virus-like particle (VLP), a recombinant viral vector, e.g., a vesicular stomatitis virus (VSV) vector, an adenovirus vector, a poxvirus vector, e.g., a modified vaccine Ankara (MVA) vector, a rabies virus vector, or a parainfluenza virus vector.

In certain embodiments, the substituted amino acid is any amino acid other than the wild-type amino acid at that position. In certain embodiments, the substitution is with a conserved amino acid and in other embodiments, the substitution is with a non-conserved amino acid. The substitution can be guided by structural analysis. In certain embodiments, mutations can be designed to be an alanine (A) substitution where the wild-type amino acid is other than A or serine (S) where the wild-type amino acid is A.

Provided herein are immunogens, e.g., immunogenic polypeptides, comprising a substituted filovirus spike glycoprotein (GP) or an immunogenic fragment thereof where the filovirus GP comprises the GP head domain (or an immunogenic fragment thereof) and the GP base domain (or an immunogenic fragment thereof). As used throughout, reference to an immunogen or a polypeptide, oligopeptide, and the like also implies an immunogenic fragment thereof, unless otherwise specified. Unless otherwise specified, an immunogen comprising a filovirus spike glycoprotein (GP) lacks the mucin like domain (MLD) of the filovirus GP1 subunit.

In certain embodiments, a filovirus GP is substituted in its GP base domain with one or more single amino acid substitutions relative to the corresponding wild-type filovirus amino acid sequence. The substitution(s) can affect the conformation of an epitope (e.g., increase the exposure of the epitope) elsewhere in the GP, such as a cross-reactive epitope in the GP head domain. In certain embodiments, the conformational change can increase the immunogenicity of the immunogen against one or more filovirus species or strains relative to the corresponding wild-type filovirus sequence. For example, in certain embodiments, a substitution in the GP base domain of EBOV GP can elicit an antibody response that is increased, e.g., increased potency, increased protection, etc., to the corresponding EBOV GP or to GPs of other EBOV strains or other filovirus species. In certain aspects, the substitution in the GP base can increase binding to the substituted EBOV GP of one or more cross-reactive top binding antibodies relative to their binding to wild-type EBOV GP. Exemplary antibodies include, but are not limited to FVM04, m8C4, FVM09, FVM17, FVM20, and h4B8. In certain embodiments, the conformational change can broaden the cross-reactive immunogenicity of the immunogen against additional, e.g., against two or more filovirus species or strains relative to the corresponding wild-type filovirus. In certain embodiments, the conformational change can both increase immunogenicity and broaden the cross-reactive immunogenicity of the immunogen against two or more filovirus species or strains relative to the corresponding wild-type filovirus.

As will be appreciated by those in the art, analogous regions from different viruses may not directly coincide by amino acid number. To the extent amino acid location is provided herein, it is understood that the analogous regions from different filoviruses can readily be identified by sequence alignment and comparison. For example, as referred to throughout, an amino acid substitution at a position corresponding to an amino acid position of a wild-type Ebola virus (EBOV) GP, wherein the filovirus GP (or immunogenic fragment thereof) is other than that wild-type EBOV GP, can be determined by aligning the wild-type EBOV GP amino acid sequence with another filovirus GP amino acid sequence (for example, see FIG. 3C) to identify amino acid positions corresponding to the wild-type EBOV GP sequence. Methods of alignment of sequences for comparison are well known in the art. Optimal alignment of sequences for comparison can be conducted, for example, by a local homology algorithm (Smith & Waterman, *Adv. Appl. Math.* 2:482 (1981), by a global alignment algorithm (Needleman & Wunsch, *J. Mol. Biol.* 48:443 (1970), by search for similarity methods (Pearson & Lipman, *Proc. Natl. Acad. Sci. U.S.A.* 85:2444 (1988); Altschul et al., *Nucl.*

Acids Res. 25:3389-402 (1997), by computerized implementations of these algorithms (e.g., GAP, BESTFIT, FASTA, and BLAST in the Wisconsin Genetics Software Package, Genetics Computer Group, 575 Science Dr., Madison, Wis.), typically using the default settings, or by manual alignment and visual inspection (see, e.g., Current Protocols in Molecular Biology, Ausubel et al. (eds.), 1994).

Certain embodiments provide for an immunogen, e.g., an immunogenic polypeptide, comprising a filovirus spike glycoprotein (GP) or immunogenic fragment thereof, wherein the filovirus GP comprises the GP head domain or an immunogenic fragment thereof and the GP base domain or an immunogenic fragment thereof and wherein the base domain comprises one or more single amino acid substitutions relative to the corresponding wild-type filovirus GP amino acid sequence. The one or more amino acid substitutions are characterized by their ability to affect the conformation of a cross-reactive epitope in the head domain. This change in confirmation can increase immunogenicity of the immunogen against the corresponding wild-type filovirus GP, and/or broaden the cross-reactive immunogenicity of the immunogen against other filovirus species or strains.

In certain embodiments, the amino acid substitution is in the GP base domain and can comprise an amino acid substitution at a position corresponding to C53, F183, N512, A562, L569, or L573 of a wild-type Ebola virus (EBOV) GP, or a combination thereof. Thus, in certain embodiments, an immunogen is provided comprising an amino acid substitution at a position corresponding to C53, F183, N512, A562, L569, or L573 of a wild-type Ebola virus (EBOV) GP, or a combination thereof.

In certain embodiments, the amino acid substitution is in the GP base domain and can comprise a substitution at a position corresponding to F183, N512, A562, L569, or L573 of a wild-type Ebola virus (EBOV) GP, or a combination thereof. Thus, in certain embodiments, an immunogen is provided comprising an amino acid substitution in the GP base domain at a position corresponding to F183, N521, A562, L569, or L573 of a wild-type Ebola virus (EBOV) GP, or a combination thereof.

In certain embodiments, the amino acid substitution is in the GP base domain and can comprise an amino acid substitution at a position corresponding to F159, P513, L515, or T565 of a wild-type Ebola virus (EBOV) GP, or a combination thereof. Thus, in certain embodiments, an immunogen is provided comprising an amino acid substitution in the GP base domain at a position corresponding to F159, P513, L515, or T565 of a wild-type Ebola virus (EBOV) GP, or a combination thereof.

In certain embodiments, the amino acid substitution is in the GP base domain and can comprise an amino acid substitution at a position corresponding to R164, L184, I185, H516, or G546 of a wild-type Ebola virus (EBOV) GP, or a combination thereof. Thus, in certain embodiments, an immunogen is provided comprising an amino acid substitution in the GP base domain at a position corresponding to R164, L184, I185, H516, or G546 of a wild-type Ebola virus (EBOV) GP, or a combination thereof.

In certain embodiments, the amino acid substitution is in the GP base domain and can comprise an amino acid substitution at a position corresponding to L51, G179, Q508, C511, Y517, R559, or C601 of a wild-type Ebola virus (EBOV) GP, or a combination thereof. Thus, in certain embodiments, an immunogen is provided comprising an amino acid substitution in the GP base domain at a position corresponding to L51, G179, Q508, C511, Y517, R559, or C601 of a wild-type Ebola virus (EBOV) GP, or a combination thereof.

In certain embodiments, the amino acid substitution is in the GP base domain and can comprise an amino acid substitution at a position corresponding to I33, P34, I38, V48, V52, L68, E103, A182, R498, R501, N514, W531, P533, E545, C556, L561, S583, or I610 of a wild-type Ebola virus (EBOV) GP, or a combination thereof. Thus, in certain embodiments, an immunogen is provided comprising an amino acid substitution in the GP base domain at a position corresponding to I33, P34, I38, V48, V52, L68, E103, A182, R498, R501, N514, W531, P533, E545, C556, L561, S583, or I610 of a wild-type Ebola virus (EBOV) GP, or a combination thereof.

In certain embodiments, the amino acid substitution is in the GP base domain and can comprise an amino acid substitution at a position corresponding to L43, V45, R54, L57, L63, V66, E71, Y99, L161, L165, P187, N506, P509, K510, W518, A525, L558, Q560, E564, T566, Q570, I603, L604, G605, C608, C609, D614, T616, I623, or W648 of a wild-type Ebola virus (EBOV) GP, or a combination thereof. Thus, in certain embodiments, an immunogen is provided comprising an amino acid substitution in the GP base domain at a position corresponding to L43, V45, R54, L57, L63, V66, E71, Y99, L161, L165, P187, N506, P509, K510, W518, A525, L558, Q560, E564, T566, Q570, I603, L604, G605, C608, C609, D614, T616, I623, or W648 of a wild-type Ebola virus (EBOV) GP, or a combination thereof.

In certain embodiments, a substitution can affect the conformation of an epitope in the GP base domain, such as the masking or silencing of an immunodominant epitope. In certain embodiments, the immunodominant epitope is a species specific epitope. For example, mutations that result in reduction of KZ52 binding to EBOV GP to less than 20% are highlighted bold and double underlined in Table 2.

Certain embodiments provide for an immunogen comprising a filovirus spike glycoprotein (GP) or immunogenic fragment thereof, wherein the filovirus GP comprises the GP head domain or an immunogenic fragment thereof and the GP base domain or an immunogenic fragment thereof, and wherein the base domain comprises one or more single amino acid substitutions relative to the wild-type filovirus GP amino acid sequence. The one or more amino acid substitutions are characterized by their ability to affect the conformation of a species specific epitope in the base domain, thereby masking the an immunodominant epitope in the base domain.

In certain embodiments, the amino acid substitution is in the GP base domain and can comprise an amino acid substitution at a position corresponding to E103, F159, E178, F183, C511, L515A, W518, N550, D552, G553, C556, or R559 of a wild-type Ebola virus (EBOV) GP, or a combination thereof. Thus, in certain embodiments, an immunogen is provided comprising an amino acid substitution in the GP base domain at a position corresponding to E103, F159, E178, F183, C511, L515A, W518, N550, D552, G553, C556, or R559 of a wild-type Ebola virus (EBOV) GP, or a combination thereof.

Masking of certain epitopes can focus the immune response on certain other epitopes, such as cross-reactive epitopes that would generally not be immunodominant. Further, mutations of specific GP base residues can be generated that simultaneously silence a base epitope and increase binding of GP to all or some of the cross-reactive antibodies listed in Table 1 (see Examples below). Examples of residues that can silence the species specific base epitope (reactive to KZ52) and increase cross-reactive epitopes are listed in Table 1. Thus, certain embodiments provide for an immunogen wherein an amino acid substitution masks an immunodominant epitope in the base domain and also increase immunogenicity of the immunogen against the corresponding wild-type filovirus GP, and/or broadens the cross-reactive immunogenicity of the immunogen against other filovirus species or strains.

In certain embodiments, the amino acid substitution is in the GP base domain and can comprise an amino acid substitution at a position corresponding to F159, F183, C511, L515, or R559 of a wild-type Ebola virus (EBOV) GP, or a combination thereof. Thus, in certain embodiments, an immunogen is provided comprising an amino acid substitution in the GP base domain at a position corresponding to F159, F183, C511, L515, or R559 of a wild-type Ebola virus (EBOV) GP, or a combination thereof.

In certain embodiments, the amino acid substitution is in the GP base domain and can comprise an amino acid substitution at a position corresponding to F159, F183, L515, or R559 of a wild-type Ebola virus (EBOV) GP, or a combination thereof. Thus, in certain embodiments, an immunogen is provided comprising an amino acid substitution in the GP base domain at a position corresponding to F159, F183, L515, or R559 of a wild-type Ebola virus (EBOV) GP, or a combination thereof.

In certain embodiments, the amino acid substitution is in the GP base domain and can comprise an amino acid substitution at a position corresponding to F183 of a wild-type Ebola virus (EBOV) GP. Thus, in certain embodiments, an immunogen is provided comprising an amino acid substitution in the GP base domain at a position corresponding to F183 of a wild-type Ebola virus (EBOV) GP.

Unless otherwise specified, an immunogen comprising a filovirus spike glycoprotein (GP) can comprise the glycoprotein glycan cap or a fragment thereof (e.g., an immunogenic fragment thereof), but does not necessarily comprises a portion of the glycan cap.

The glycosylation state of proteins can affect immunogenicity. Thus, certain embodiments provide for one or more amino acid substitutions that alter the glycosylation of a filovirus GP. In certain embodiments, the amino acid substitution reduces glycosylation. GP1 contains a highly glycosylated regions termed the "glycan cap" (wild-type EBOV residues 227-313). In certain embodiments, the amino acid substitution reducing glycosylation is in the glycan cap region. The GP1 glycan cap comprises at least four N-glycosylation sites. For example, it was observed that substitutions in three (N238, N257, N268) out of these four glycosylation sites increased the binding of the cross-reactive antibody FVM04. Residues at certain positions play a role in directing glycosylation (recognition sites). In particular, threonine (T) residues near the glycosylation site can be part of a glycosylation recognition site. For example, when threonine residues two amino acids C-terminal to certain glycosylation sites (T240, T259, and T270) were mutated, increased binding of the cross-reactive antibody FVM04 was also observed. Thus, certain embodiments provide for an amino acid substitution at a position corresponding to N238, T240, N257, T259, N268, or T270 of a wild-type EBOV GP, or a combination thereof.

Certain embodiments provide for an immunogen comprising a filovirus spike glycoprotein (GP) or immunogenic fragment thereof, wherein the filovirus GP comprises the GP head domain or an immunogenic fragment thereof, the GP base domain or an immunogenic fragment thereof, and the glycan cap or an immunogenic fragment thereof, wherein the glycan cap comprises one or more single amino acid substitutions relative to the corresponding wild-type filovirus GP. The one or more amino acid substitutions are characterized by their ability to reduce glycosylation of the glycoprotein. This can increase immunogenicity of the immunogen, and/or broaden the cross-reactive immunogenicity of the immunogen against other filovirus species or strains.

In certain embodiments, the amino acid substitution is in the glycan cap and can comprise an amino acid substitution at a position corresponding to N238, T240, N257, T259, N268, or T270 of a wild-type Ebola virus (EBOV) GP, or a combination thereof. Thus, in certain embodiments, an immunogen is provided comprising an amino acid substitution in the glycan cap at a position corresponding to N238, T240, N257, T259, N268, or T270 of a wild-type Ebola virus (EBOV) GP, or a combination thereof.

In certain embodiments, at least two glycosylation sites are disrupted by substituting the Asparagine (N) of the N-glycosylation site and/or the upstream threonine (T) of the recognition site for N-glycosylation. In certain embodiments, amino acid substitutions occur in the glycan cap comprising at least two substitutions selected from a group consisting of amino acid substitutions at a position corresponding to N238 and/or T240, at a position corresponding to N257 and/or T259, and at a position corresponding to N268 and/or T270 of a wild-type Ebola virus (EBOV) GP. Thus, in certain embodiments, an immunogen is provided comprising at least two amino acid substitutions in the glycan cap selected from a group consisting of amino acid substitutions at a position corresponding to N238 and/or T240, at a position corresponding to N257 and/or T259, and at a position corresponding to N268 and/or T270 of a wild-type Ebola virus (EBOV) GP. In certain embodiments, the amino acid substitutions disrupt at least two glycosylation sites. For purposes of this disclosure the pairings of N238/T240, N257/T259, and N268/T270 can be considered glycosylation sites.

Two monoclonal pan-ebolavirus antibodies, FVM09 (Keck, et al., 2016, *J Virol*, 90:279-291; PCT US15/57627 which are incorporated herein by reference) and m8C4 (Holtsberg, et al., 2016, *J Virol*, 90:266-278; PCT US15/37493 which are incorporated herein by reference) have been previously reported. Alanine scanning mutagenesis analysis revealed that EBOV GP residues W288, F290, and W291 and to a lesser extent E278 were involved in binding of FVM09 to EBOV GP (FIG. 5A). In contrast, mutation of the adjacent E292 to alanine resulted in over two fold increase in binding of FVM09 over binding to wild-type EBOV GP (FIG. 5A). All these residues are located within a disordered loop in EBOV GP structure connecting the β17 to β18 strands in the glycan cap (Lee, et al., 2008, *Nature*, 454 (7201): 177-182). Binding of m8C4 to EBOV GP was dependent primarily on R136 (within the inner chalice) as well as Q251, F252 (within the glycan cap adjacent to the β17-β18 loop where FVM09 epitope is located (FIG. 5B). To a lesser extent, E106A and E258A mutations also reduced m8C4 binding (FIG. 5B). In contrast, mutation of F290, W291, and E292 to alanine resulted in 3-4 fold increase in m8C4 binding to the respective mutant compared to wild-type GP (FIG. 5B). These data indicate that knocking out FVM09 binding site (F290, W291) results in better exposure of m8C4 epitope. Mutation of E292 enhances the binding of both FVM09 and m8C4 suggesting that incorporation of a mutation in this site can enhance cross-reactive immunogenicity.

Certain embodiments provide for an immunogen comprising a filovirus spike glycoprotein (GP) or immunogenic fragment thereof, wherein the filovirus GP comprises the GP head domain or an immunogenic fragment thereof, the GP base domain or an immunogenic fragment thereof, and the glycan cap or immunogenic fragment thereof, wherein the glycan cap comprises one or more single amino acid substitutions relative to the corresponding wild-type filovirus GP amino acid sequence within the disordered loop connecting the β17 to β18 strands. The one or more amino acid substitutions are characterized by their ability to affect the conformation of a cross-reactive epitope in the glycan cap. This can increase immunogenicity of the immunogen and/or broaden cross-reactive immunogenicity of the immunogen against other filovirus species or strains.

In certain embodiments, the amino acid substitution is within the disordered loop connecting the β17 to β18 strands and can comprise an amino acid substitution at a position corresponding to F290, W291, or E292 of a wild-type Ebola virus (EBOV) GP, or a combination thereof. Thus, in certain embodiments, an immunogen is provided comprising an amino acid substitution within the disordered loop connecting the β17 to β18 strands at a position corresponding to F290, W291, or E292 of a wild-type Ebola virus (EBOV) GP, or a combination thereof.

In certain embodiments, the amino acid substitution is in the disordered loop connecting the β17 to β18 strands and can comprise an amino acid substitution at a position corresponding to E292 of a wild-type Ebola virus (EBOV) GP. Thus, in certain embodiments, an immunogen is provided comprising an amino acid substitution in the disordered loop connecting the β17 to β18 strands at a position corresponding to E292 of a wild-type Ebola virus (EBOV) GP.

In certain embodiments, the amino acid substitution can comprise a combination of at least one single amino acid substitution in the glycan cap that disrupts N-glycosylation of the glycoprotein (e.g., at a position corresponding to N238, T240, N257, T259, N268, or T270 of wild-type EBOV GP, or a combination thereof) and at least one single amino acid substitution within the disordered loop connecting the β17 to β18 strands (e.g., at a position corresponding to F290, W291, or E292 of wild-type EBOV GP, or a combination thereof).

Certain embodiments provide for the mutation of GP1 and GP2 residues, in the region surrounding the GP fusion loop, including, but not limited to the epitope recognized by monoclonal antibody CA45, that increase the binding efficacy of CA45-like antibodies (FIG. 7A). Bulky residues in this region surround the CA45 epitope (FIG. 7B) and possibly restrict access of antibodies to the epitope. Such mutations can be incorporated into Ebola GP-based vaccines to enhance the ability of an immunogen to elicit CA45-like broadly neutralizing antibodies in the host. (U.S. Provisional Application No. 62/406,598).

Thus, certain embodiments provide for at least one single amino acid substitution at a position corresponding to N40, D192, F193, and/or F194 of wild-type EBOV GP, or a combination thereof. In certain embodiments, the residues are substituted with an amino acid residue with no side chain or a small sidechain, such as glycine, alanine, or serine. In certain embodiments, the substitution is to alanine. Mutations that can enhance the binding of CA45-like antibodies include one or more of N40A, D192A, F193A, and/or F194A (FIG. 7A).

Certain embodiments provide for a combination of one or more mutations that enhance the elicitation and binding of CA45-like antibodies to the fusion loop region, with any other mutation described herein to simultaneously enhance reactivity of the antigen to both the apex binders (e.g., FVM04) and fusion loop binders (e.g., CA45).

Filoviruses enter the endosomes by micropinocytosis and after entry into endosomes GPs are cleaved by cathepsin proteases as an essential step in infectivity, reducing GP1 to a ~18 kDa product (referred to here as $GP_{CL}$) that is associated with the whole GP2, but lacks the entire glycan cap and the MLD (Chandran, et al., 2005, Science, 308 (5728): 1643-1645; Kaletsky, et al., 2007, J. Virol., 81 (24): 13378-13384; Schomberg, et al., 2006, J. Virol., 80 (8): 4174-4178). The cleavage occurs between residues R200 and E201 in the cathepsin cleavage loops (Hood, et al., 2010, J. Virol., 84: 2972-2982). It was discovered that several cross-neutralizing antibodies including FVM04 and CA45 bind with higher affinity to the $GP_{CL}$ than to full length GP.

In certain embodiments, $GP_{CL}$ can be used as a modified vaccine for inducing broadly neutralizing protective responses. Cleaved GP can be produced by a number of methods including: cleavage of purified GP by cathepsin B, cathepsin L, or thermolysin; and recombinant generation of $GP_{CL}$ by replacing the glycan cap and MLD in GP by a flexible linker of 5-50 amino acids. Other mutations that affect the binding of the antigens to cross-neutralizing antibodies described herein may also be incorporated in such recombinant $GP_{CL}$. Further, recombinant $GP_{CL}$ can be incorporated in various vaccine formats including: recombinant purified protein; virus-like particles; vesicular stomatitis virus (VSV) vector expressing Ebola $GP_{CL}$ instead of VSV-G; an adenovirus vector carrying $GP_{CL}$; a parainfluenza virus (PIV) vector carrying $GP_{CL}$; and any other viral vector $GP_{CL}$.

Also provided herein are methods of increasing the immunogenicity and/or broadening the cross-reactive immunogenicity of an immunogen comprising a filovirus GP or an immunogenic fragment thereof, and the like, and methods of masking an immunodominant epitope in the same. The methods comprise making any one or more of the single amino acid substitutions disclosed herein in a filovirus GP.

Certain embodiments provide for a composition comprising an immunogen or a fragment thereof described anywhere herein and an adjuvant.

Certain embodiments provide for a composition comprising an immunogen or a fragment thereof described anywhere herein as part of a filovirus virus-like particle (VLP) (Warfield and Aman, 2011, J Infect Dis, 204 (Suppl 3): S1053-1059). The expression and subsequent oligomerization of the matrix protein VP40 has been described as sufficient to drive the formation of filamentous, enveloped VLPs that are released from cells (Bavari et al., 2002, J Exp Med, 195:593-602; Swenson et al., 2004, FEMS Immunol Med Microbiol, 40:27-31; Harty et al., 2000, Proc Natl Acad Sci USA, 97:13871-6; Han et al., 2003, J Virol, 77:1793-800; Licata et al., 2004, J Virol, 78:7344-51; Jasenosky and Kawaoka, 2004, Virus Res, 106:181-8; Jasenosky et al., 2001, J Virol, 75:5205-14). Efficiency of the production of VLPs driven by sole expression of VP40, however, is low and VLP formation and release can be increased by the presence of additional viral proteins, for example, GP, NP, and VP24 (Swenson D L et al., 2004, FEMS Immunol Med Microbiol, 40:27-31; Waffleld et al., 2007, J Infect Dis, 196 (Suppl 2): 5421-9; Kallstrom et al., 2005, J Virol Methods, 127:1-9; Licata et al., 2004, J Virol, 78:7344-51).

In certain embodiments, a VLP as provided herein comprises a modified filovirus GP as provided herein and a filovirus VP40. In certain embodiments, the VLP comprises a filovirus GP and a filovirus nucleoprotein (NP). In certain embodiments, the VLP comprises a filovirus GP and a filovirus VP24. In certain embodiments, the VLP comprises a filovirus GP and a filovirus VP40 and further comprises a filovirus nucleoprotein (NP) and/or a filovirus VP24.

Certain embodiments provide for an isolated polynucleotide comprising a nucleic acid encoding an immunogen, e.g., an immunogenic polypeptide, or a fragment thereof disclosed anywhere herein, or a subunit thereof. Certain embodiments provide for a vector comprising such a polynucleotide. Certain embodiments provide for a composition comprising such a polynucleotide or vector.

Polynucleotides encoding polypeptides disclosed herein can be cloned using DNA amplification methods, such as the polymerase chain method (PCR) (see e.g., Sambrook et al. (1989) *Molecular Cloning: A Laboratory Manual*, 2nd ed., Cold Spring Harbor, N.Y.; Berger & Kimmel (1987) *Methods in Enzymology*. Vol. 152). Thus, for example, a nucleic acid molecule encoding a filovirus GP can be PCR amplified using a sense primer containing one restriction site and an antisense primer containing another restriction site. This will produce a nucleic acid encoding the desired sequence or subsequence having terminal restriction sites. This nucleic acid can then be ligated into a vector having appropriate corresponding restriction sites. Suitable PCR primers can be chosen by one of ordinary skill in the art based on the sequence to be expressed. Appropriate restriction sites can also be added by ligation or site-directed mutagenesis (see Gillman & Smith *Gene* 8: 81-97 (1979); Roberts et al. *Nature* 328: 731-4 (1987)).

Immunogens disclosed herein are typically expressed using an expression vector. Expression vectors can be either self-replicating extrachromosomal vectors or vectors that integrate into a host genome. Generally, expression vectors include transcriptional and translational regulatory nucleic acid sequences operably linked to the nucleic acid encoding the target protein. The term "control sequences" refers to DNA sequences involved in the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers. One of ordinary skill in the art will recognize that a nucleic acid is "operably linked" when it is placed into a functional relationship with another nucleic acid sequence. For example: DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Operably linked DNA sequences can be contiguous or non-contiguous. Methods for linking DNA sequences are well-known in the art and include use of the polymerase chain reaction and ligation. The transcriptional and translational regulatory nucleic acid will generally be appropriate to the host cell used to express the target protein.

Numerous types of expression vectors, and regulatory sequences are known in the art for a variety of host cells. Methods for expressing polypeptides are also well known (e.g., Sambrook et al. (1989) *Molecular Cloning, A Laboratory Manual*, 2nd ed., vol. 1-3, Cold Spring Harbor Laboratory; Berger and Kimmel (1987) *Guide to Molecular Cloning Techniques, Methods in Enzymology*, vol. 152, Academic Press, Inc., San Diego, Calif.; Ausubel et al. (1995) *Current Protocols in Molecular Biology*, John Wiley & Sons, Inc., NY). Certain illustrative, non-limiting, examples of vectors include plasmids pET, pALTER, pCMV, pBlueScript, pcDNA3, pHCMV/Zeo, pCR3.1, pEF1/His, pIND/GS, pRc/HCMV2, pSV40/Zeo2, pTRACER-HCMV, pUB6/V5-His, pVAX1, and pZeoSV2 (available from Invitrogen, San Diego, Calif.), and plasmid pCI (available from Promega, Madison, Wis.).

Transcriptional and translational regulatory sequences can include, but are not limited to, promoter sequences, ribosomal binding sites, transcriptional start and stop sequences, translational start and stop sequences, and enhancer or activator sequences. Promoter sequences can encode either constitutive or inducible promoters. Promoters can be either naturally occurring promoters or hybrid promoters. Hybrid promoters, which combine elements of more than one promoter, are also known in the art.

An expression vector can comprise additional elements. For example, the expression vector can have two replication systems, thus allowing it to be maintained in two organisms, for example in mammalian or insect cells for expression and in a prokaryotic host for cloning and amplification. Furthermore, for integrating expression vectors, the expression vector contains at least one sequence homologous to a sequence in the host cell genome, and preferably two homologous sequences that flank the expression construct. The integrating vector can be directed to a specific locus in the host cell by selecting the appropriate homologous sequence for inclusion in the vector.

Certain embodiments provide for a host cell comprising a polynucleotide or vector comprising a nucleic acid encoding an immunogen disclosed herein or a fragment thereof. Certain embodiments provide a method of making an immunogen or fragment thereof disclosed anywhere herein, the method comprising culturing a host cell comprising a polynucleotide or vector described herein and recovering and/or isolating the immunogen.

Immunogens comprising filovirus GP can be produced by culturing a host cell transformed with an expression vector containing a nucleic acid encoding a filovirus GP, under the appropriate conditions to induce or cause expression of the immunogen. The conditions appropriate for protein expression will vary with the choice of the expression vector and the host cell. Also, the coding sequences can be optimized for expression in the selected host cells.

Host cells include yeast, bacteria, archaebacteria, fungi, insect and animal cells, including mammalian cells such as, but are not limited to, *Drosophila melanogaster* cells, *Saccharomyces cerevisiae* and other yeasts, *E. coli, Bacillus subtilis*, Sf9 cells, C129 cells, 293 cells, Neurospora, BHK, CHO, COS, HeLa cells, and Hep G2 cells.

In some embodiments, the immunogens are expressed in mammalian host cells. Exemplary mammalian host cell lines include, but are not limited to, 293, CHO (Chinese Hamster Ovary), DG44 and DUXB11 (Chinese Hamster Ovary lines, DHFR minus), HELA (human cervical carcinoma), CVI (monkey kidney line), COS (a derivative of CVI with SV40 T antigen), VERY, BHK (baby hamster kidney), MDCK, WI38, R1610 (Chinese hamster fibroblast) BALBC/3T3 (mouse fibroblast), HAK (hamster kidney line), SP2/O (mouse myeloma), P3x63-Ag3.653 (mouse myeloma), BFA-1c1BPT (bovine endothelial cells), RAJI (human lymphocyte) and 293 (human kidney). Host cell lines are typically available from commercial services, the American Tissue Culture Collection or from published literature.

Promoters from viral genes are frequently used in mammalian expression systems, because the viral genes are often highly expressed and have a broad host range. Examples include the SV40 early promoter, mouse mammary tumor virus LTR promoter, adenovirus major late promoter, herpes simplex virus promoter, and the CMV promoter. Typically, transcription termination and polyadenylation sequences recognized by mammalian cells are regulatory regions located 3' to the translation stop codon and thus, together with the promoter elements, flank the coding sequence. Examples of transcription terminator and polyadenylation signals include those derived from SV40.

Methods of introducing exogenous nucleic acid into host cells are well known in the art, and will vary with the host cell used. Suitable techniques include, but are not limited to, dextran-mediated transfection, calcium phosphate precipitation, polybrene mediated transfection, protoplast fusion, electroporation, viral infection, encapsulation of the polynucleotide(s) in liposomes, and direct microinjection of the DNA into nuclei.

In some embodiments, the immunogens are expressed in bacterial systems. Bacterial expression systems are well known in the art. Promoters from bacteriophage can also be used and are known in the art. In addition, synthetic promoters and hybrid promoters are also useful; for example, the tac promoter is a hybrid of the trp and lac promoter sequences. Furthermore, a bacterial promoter can include naturally occurring promoters of non-bacterial origin that have the ability to bind bacterial RNA polymerase and initiate transcription. In addition to a functioning promoter sequence, an efficient ribosome binding site is desirable. The expression vector can also include a signal peptide sequence that provides for secretion of the target protein in bacteria. A polypeptide is either secreted into the growth media (gram-positive bacteria) or into the periplasmic space, located between the inner and outer membrane of the cell (gram-negative bacteria). The expression vector can also include an epitope tag providing for affinity purification of the target protein. The bacterial expression vector can also include a selectable marker gene to allow for the selection of bacterial strains that have been transformed. Suitable selection genes include genes that render the bacteria resistant to drugs such as ampicillin, chloramphenicol, erythromycin, kanamycin, neomycin and tetracycline. Selectable markers also include biosynthetic genes, such as those in the histidine, tryptophan, and leucine biosynthetic pathways. These components are assembled into expression vectors. Expression vectors for bacteria are well known in the art, and include vectors for *Bacillus subtilis, E. coli, Streptococcus cremoris,* and *Streptococcus lividans,* among others. The bacterial expression vectors are transformed into bacterial host cells using techniques well known in the art, such as calcium chloride treatment, electroporation, and others.

The immunogens disclosed herein can also be produced in insect cells. Expression vectors for the transformation of insect cells, and in particular, baculovirus-based expression vectors, are well known in the art. The filovirus GP can also be produced in yeast cells. Yeast expression systems are well known in the art, and include expression vectors for *Saccharomyces cerevisiae, Candida albicans* and *C. maltosa, Hansenula polymorpha, Kluyveromyces fragilis* and *K. lactis, Pichia guillerimondii* and *P. pastoris, Schizosaccharomyces pombe,* and *Yarrowia lipolytica.*

The immunogens disclosed herein can be produced in a cell-free expression system in vitro using an expression vector containing nucleic acid encoding the immunogen, under the appropriate conditions to induce or cause expression of the immunogen in vitro. Cell-free in vitro expression systems are well known in the art.

The immunogens can also be made as fusion proteins, using techniques that are well known in the art. For example, a filovirus GP can be made as a fusion protein to increase expression, to increase serum half-life, or to link it with a tag polypeptide that provides an epitope to which an anti-tag antibody can selectively bind. Exemplary tags or fusion partners include the myc epitope, the immunoglobulin Fc domain, and 6-histidine. The epitope tag is generally placed at the amino- or carboxyl-terminus of the target protein. The presence of such epitope-tagged forms of a target protein can be detected using an antibody against the tag polypeptide. Thus, the epitope tag enables the target proteins to be readily purified by affinity purification using an anti-tag antibody or another type of affinity matrix that binds to the epitope tag.

The immunogens can be purified or isolated after expression in a host cell. Purity and homogeneity are typically determined using analytical chemistry techniques such as polyacrylamide gel electrophoresis or high performance liquid chromatography. A protein that is the predominant species present in a preparation is substantially purified. The term "purified" denotes that a protein gives rise to essentially one band in an electrophoretic gel. For example, it means that the protein is at least 85% pure, such as at least 95% pure, such as at least 99% pure. The term "isolated polypeptides" also includes polypeptides in situ within recombinant host cells, since at least one component of the polypeptide natural environment will not be present.

The immunogens can be isolated or purified in a variety of ways known to those of ordinary skill in the art, depending on what other components are present in the sample. Standard purification methods include electrophoretic, molecular, immunological and chromatographic techniques, including ion exchange, hydrophobic, affinity, lectin-affinity and reverse-phase HPLC chromatography, and chromatofocusing. For example, the target protein can be purified using an affinity column. Ultrafiltration and diafiltration techniques, in conjunction with protein concentration, are also useful. Suitable purification techniques are standard in the art (see generally R. Scopes (1982) *Protein Purification,* Springer-Verlag, N.Y.; Deutcher (1990) *Methods in Enzymology* vol. 182: Guide to Protein Purification, Academic Press, Inc. N.Y.). The degree of purification will vary depending on the use of the polypeptide. In some instances no purification is necessary.

In certain embodiments, an immunogen described herein can comprise a heterologous amino acid sequence or one or more other moieties not normally associated with a filovirus polypeptide (e.g., an antimicrobial agent, a therapeutic agent, a prodrug, a peptide, a protein, an enzyme, a lipid, a biological response modifier, pharmaceutical agent, a lymphokine, a heterologous antibody or fragment thereof, a detectable label, polyethylene glycol (PEG), and a combination of two or more of any said agents). In further embodiments, an immunogen can comprise a detectable label selected from the group consisting of an enzyme, a fluorescent label, a chemiluminescent label, a bioluminescent label, a radioactive label, or a combination of two or more of any said detectable labels.

Certain embodiments provide for composition comprising an immunogen and methods for preparing them. In certain embodiments, a composition in prepared by suspending and packaging one or more immunogens with a suitable pharmaceutically acceptable carrier. Suitable pharmaceutically acceptable carriers include sterile water or a sterile physiological salt solution, e.g., phosphate buffered saline (PBS). Pharmaceutically acceptable carriers also encompass any of the standard pharmaceutical carriers, such as those suitable for parenteral administration, such as by intramuscular, intravenous, intradermal, intraperitoneal, and subcutaneous routes. Examples of such formulations include aqueous and non-aqueous, isotonic sterile injection solutions, which contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

Certain embodiments comprise an immunogen and an adjuvant. Adjuvants are used to enhance an immune response to an immunogen. Adjuvants can be obtained from any of a number of sources including from natural sources, recombinant sources, and/or be chemically synthesized, etc. Suitable exemplary adjuvants include, among others, liposomes, alum, monophosphoryl lipid A, immune-stimulating complexes (ISCOMS), LPS analogs including 3-O-deacylated monophosphoryl lipid A (Ribi Immunochem Research, Inc.; Hamilton, Mont.), mineral oil and water, aluminum hydroxide, Amphigen, Avirdine, L121/squalene, muramyl peptides, and saponins, such as Quil A, and any biologically active factor, such as cytokine, an interleukin, a chemokine, a ligands, and optimally combinations thereof. Certain of these biologically active factors can be expressed in vivo, e.g., via a plasmid or viral vector. For example, such an adjuvant can be administered with a priming DNA vaccine encoding an antigen to enhance the antigen-specific immune response compared with the immune response generated upon priming with a DNA vaccine encoding the antigen only.

Certain embodiments provide for DNA vaccines comprising a nucleic acid molecule encoding one or more immunogens disclosed herein. Thus, some embodiments provide an immunogenic composition comprising a nucleic acid molecule encoding an immunogen and a pharmaceutically acceptable carrier. Methods for preparing and administering a DNA vaccine expressing heterologous polypeptides are known in the art and have been previously described (see, e.g., Doolan & Hoffman, *Int. J. Parasitol.* 31:753-762, (2001)).

In certain embodiments, a vaccine composition is a viral vaccine comprising a viral vector encoding one or more immunogens disclosed herein. Exemplary viral vectors for use in the vaccine compositions, but are not limited to, vaccinia viral vectors (such as vectors based on modified vaccinia virus Ankara or avian pox viruses), adenoviral vectors, VSV vectors, herpesvirus vectors, rabies virus vectors, and yellow fever viral vectors (see, e.g., Tao et al., *J. Exp. Med.* 201:201-209 (2005)). Methods for preparing and administering viral vaccines expressing filovirus proteins are known in the art. A vaccine composition as provided herein can also be a naked DNA vaccine.

In another aspect, the immunogens and the sequences encoding them can be used to induce an immune response to a filovirus in a subject. Suitably, the immunogens or coding sequences are delivered to the cells in an effective amount and in a manner which presents them favorably for induction of an antibody response, a cellular immune response, or both. Any of the immunogens described herein can be utilized. The effective amount and method of administration of a particular therapeutic or prophylactic treatment can vary based on the individual patient and the stage of the disease, as well as other factors known to those of skill in the art. Therapeutic efficacy and toxicity of such compounds can be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio of toxic to therapeutic effects is the therapeutic index, and it can be expressed as the ratio, $LD_{50}/ED_{50}$. The data obtained from cell culture assays and animal studies is used in formulating a range of dosages for human use. The dosage of such compounds lies preferably within a range of circulating concentrations that include the $ED_{50}$ with little or no toxicity. The dosage varies within this range depending upon the dosage form employed, sensitivity of the patient, and the route of administration.

In certain embodiments, an immunogen is delivered to the subject in protein form by a non-viral delivery vehicle. For example, liposomes, micelles, gels, multiple antigen complexes can be prepared utilizing the chimeric glycoproteins described herein. A suitable immunogenic amount of the immunogen can be readily determined. Optionally, the immunogen can be conjugated with a polyethylene glycol conjugate according to published techniques. See, e.g., U.S. Pat. No. 6,399,385 and references cited therein.

In certain embodiments, a viral vector is utilized for delivery of an immunogen to a subject. Any suitable viral system can be used including, e.g., adenoviruses, poxviruses, and the like.

An immunogen can be administered by any suitable method of administration known in the art including, but not limited to, intradermally, subcutaneously, intramuscularly, intraperitoneally, orally, ocularly (e.g., as an eye spray), and intravenously. Vaccines are conventionally administered parenterally, by injection, for example, either subcutaneously or intramuscularly. Additional formulations that are suitable for other modes of administration include suppositories and, in some cases, oral formulations, or nasal sprays. For suppositories, traditional binders and carriers can include, for example, polyalkalene glycols or triglycerides. Oral formulations include such normally employed excipients as, for example, pharmaceutical grades of mannitol, lactose, starch, magnesium stearate, sodium saccharine, cellulose, magnesium carbonate, and the like.

Certain embodiments provide for detecting anti-filovirus GP antibodies in a sample. In some embodiments, the sample is suspected of containing a filovirus infection. The method includes contacting the sample suspected of containing an antibody which binds an epitope of the immunogen described herein, allowing the antibody to bind to the immunogen to form an immunological complex, detecting the formation of the immunological complex and correlating the presence or absence of the immunological complex with the presence or absence of anti-filovirus antibodies in the sample. The sample can be biological, environmental or a food sample.

As used herein, "detecting the formation of the immunological complex" is intended to include discovery of the presence or absence of anti-filovirus antibodies in a sample. The presence or absence of anti-filovirus antibodies can be detected using an immunoassay. A number of immunoassays used to detect and/or quantitate antigens are well known to those of ordinary skill in the art. See Harlow and Lane, Antibodies: A Laboratory Manual (Cold Spring Harbor Laboratory, New York 1988 555-612). Such immunoassays include antibody capture assays, antigen capture assays, and two-antibody sandwich assays. These assays are commonly used in the art. In an antibody capture assay, the antigen is attached to solid support, and labeled antibody is allowed to bind. After washing, the assay is quantitated by measuring the amount of antibody retained on the solid support. A variation of this assay is a competitive ELISA wherein the antigen is bound to the solid support and two solutions containing antibodies which bind the antigen, for example, serum from an filovirus vaccine and a known anti-filovirus glycoprotein monoclonal antibody, are allowed to compete for binding of the chimeric protein. The amount of monoclonal bound is then measured, and a determination is made as to whether the serum contains anti-filovirus glycoprotein antibodies. This competitive ELISA can be used to indicate immunity to known protective epitopes in a vaccine following vaccination.

In an antigen capture assay, the antibody is attached to a solid support, and labeled antigen is allowed to bind. The unbound proteins are removed by washing, and the assay is quantitated by measuring the amount of antigen that is bound. In a two-antibody sandwich assay, one antibody is bound to a solid support, and the antigen is allowed to bind to this first antibody. The assay is quantitated by measuring the amount of a labeled second antibody that can bind to the antigen.

These immunoassays typically rely on labeled antigens, antibodies, or secondary reagents for detection. These proteins can be labeled with radioactive compounds, enzymes, biotin, or fluorochromes. Of these, radioactive labeling can be used for almost all types of assays and with most variations. Enzyme-conjugated labels are particularly useful when radioactivity must be avoided or when quick results are needed. Biotin-coupled reagents usually are detected with labeled streptavidin. Streptavidin binds tightly and quickly to biotin and can be labeled with radioisotopes or enzymes. Fluorochromes, although requiring expensive equipment for their use, provide a very sensitive method of detection. Antibodies useful in these assays include monoclonal antibodies, polyclonal antibodies, and affinity purified polyclonal antibodies. The binding of these labels to antibodies or fragments thereof can be accomplished using standard techniques commonly known to those of ordinary skill in the art. Typical techniques are described by Kennedy, J. H., et al., *Clin. Chim. Acta* 70:1-31 (1976), and Schurs, A. H. W. M., et al. *Clin. Chim Acta* 81:1-40 (1977). Coupling techniques mentioned in the latter are the glutaraldehyde method, the periodate method, the dimaleimide method, and others, all of which are incorporated by reference herein.

Provided herein are methods for monitoring the immune status of a subject vaccinated against infection or disease caused by filovirus, comprising (a) contacting a biological sample comprising antibodies from a subject with one or more immunogens disclosed herein under conditions enabling the formation of antigen/antibody complexes between the polypeptides and the antibodies, and (b) detecting the formation of antigen/antibody complexes.

In the diagnostic and monitoring methods described above, the biological sample can be further contacted with one or several antigenic peptides originating from other filovirus antigens.

In some embodiments, the diagnostic and screening agents and assays are nucleic acid-based. Exemplary diagnostic and screening agents for use in nucleic acid-based assays include nucleic acid probes complementary to nucleic acid molecules encoding filovirus polypeptides of the disclosure. Nucleic-acid based diagnostic and screening assays are well known in the art. Exemplary diagnostic and screening assays to be used in this aspect of the disclosure are described in Scherf et al., U.S. Pat. No. 6,855,323, herein incorporated by reference.

In another aspect a kit for detecting filovirus in a biological sample is provided. The kit includes a container holding one or more immunogens and instructions for using them for the purpose of identifying the presence of anti-filovirus antibodies to form an immunological complex and detecting the formation of the immunological complex such that the presence or absence of the immunological complex correlates with presence or absence of filovirus in the sample. Examples of containers include multiwell plates which allow simultaneous detection of filovirus in multiple samples.

EXAMPLES

Example 1

ELISA analyses were used to measure antibody binding to different isolated domains of EBOV GP (Keck, et al., 2016, *J Virol*, 90:279-291; Holtsberg, et al., 2016, *J Virol*, 90:266-278), and an alanine-scanning mutagenesis approach to determine the epitopes of several cross-reactive antibodies. Comprehensive high-throughput alanine scanning mutagenesis was carried out on an expression construct for EBOV GP (EBOV strain Mayinga-76; UniProt accession number Q05320) (Davidson et al., 2015, *J Virol.*, 89(21):10982-9). Residues 33-676 of full-length EBOV GP were mutagenized to alanine (with alanine residues changed to serine) to create a library of clones, each representing an individual point mutant. GP residues 1-32, which constitute the GP signal peptide, were not mutagenized. The resulting EBOV GP alanine-scan library covered 99.5% of target residues (641 of 644).

The immunoreactivity of each mAb with expressed wild-type EBOV GP was first optimized by determining reactivity with fixed or unfixed cells over a range of MAb concentrations to identify optimal signal-to-background ratios (>5:1) and to ensure that signals were within the linear range of detection. The EBOV GP mutation library, arrayed in 384-well microplates, was transfected into HEK-293T cells and allowed to express for 22 hours. Cells were fixed in 4% paraformaldehyde in PBS plus calcium and magnesium, or left unfixed, and were then incubated with an anti-EBOV mAb diluted in 10% normal goat serum (NGS) (Sigma-Aldrich, St. Louis, Mo.). The cells were incubated with anti-EBOV antibody for 1 hour at room temperature, followed by a 30 minute incubation with Alexa Fluor 488-conjugated secondary antibody (Jackson ImmunoResearch Laboratories, Westgrove, Pa.) in 10% NGS. Cells were washed twice with PBS without calcium or magnesium and resuspended in Cellstripper (Cellgro, Manassas, Va.) plus 0.1% BSA (Sigma-Aldrich, St. Louis, Mo.). Cellular fluorescence was detected using the Intellicyt high throughput flow cytometer (Intellicyt, Albuquerque, N. Mex.). Background fluorescence was determined by fluorescence measurement of vector-transfected control cells. MAb reactivities against each mutant EBOV GP clone were calculated relative to wild-type EBOV GP reactivity by subtracting the signal from mock-transfected controls and normalizing to the signal from wild-type GP-transfected controls.

Mutated residues within critical clones were identified as critical to the mAb epitope if they did not support reactivity of the test mAb but did support reactivity of other control EBOV mAbs. This counter-screen strategy facilitates the exclusion of GP mutants that are locally misfolded or that have an expression defect. The detailed algorithms used to interpret shotgun mutagenesis data are described elsewhere (Davidson and Doranz, 2014, which is incorporated herein in its entirety).

Using this approach, residues critical for the GP binding of pan-ebolavirus mAbs FVM04, FVM09, FVM17, FVM20, m8C4, 4B8, and CA45 were determined.

A vesicular stomatitis virus (VSV) pseudotyped with EBOV GPwt (wild-type) or a mutant of EBOV GP in which residues F290, W291, and E292 are mutated to alanine (VSV-EBOV GP-AAA) was created. The generation of the pseudotyped viruses was performed as described previously (Whitt M A, 2010, J Virol Methods 169, 365-374). The pseudotyped virus expressed luciferase upon infection of the cells (Whitt M A, 2010, J Virol Methods 169, 365-374). Vero cells were infected with VSV-EBOV GPwt or VSV-EBOV GP-AAA and neutralization of the two viruses by different concentrations of m8C4 was determined. As shown in FIG. 6, while m8C4 poorly neutralized the VSV pseudotype expressing wild-type EBOV GP, the pseudotype with the EBOV GP-AAA was potently neutralized by m8C4. The neutralizing activity of m8C4 was over 300 fold higher against VSV-EBOV GP-AAA as compared with VSV-EBOV GPwt (EC50 of 0.035 µg/ml for mutant vs. >10 µg/ml for wt (FIG. 6). These data further indicate that mutating these residues within an EBOV GP vaccine could significantly enhance the neutralizing response to EBOV and likely other ebolavirus species as the epitope of m8C4 is conserved among ebolaviruses.

A mutation at positions E292 to any other amino acid (to be determined empirically) can be incorporated in a GP-based Ebola vaccine. Such mutant is expected to enhance the generation of FVM09 and m8C4 type antibodies by the immune system. Such mutation can be further combined with specific mutations in the base of the GP or glycosylation silencing mutants of the glycan cap described above.

Any combination of E292 mutation with F290 or W291 mutation can (double and triple mutants) incorporated into a vaccine. These mutations are expected to primarily enhance neutralizing responses to the m8C4 epitope. Such mutations can be further combined with specific mutations in the base of the GP or glycosylation silencing mutants of the glycan cap described above.

Example 2

Figure 1:
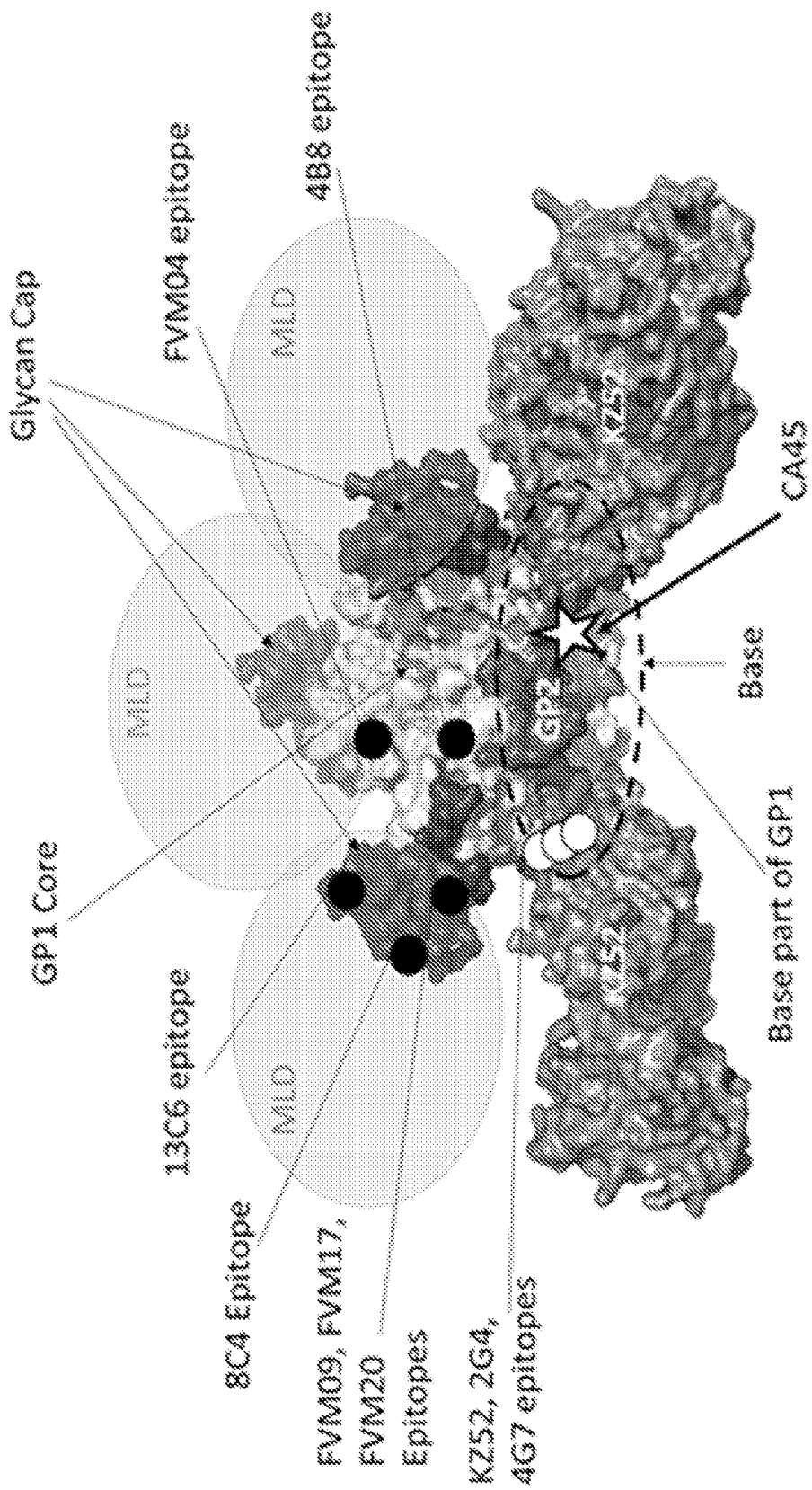

It has been determined that specific mutations in the base of the GP trimer can have a global impact on the exposure of cross-reactive and cross-neutralizing epitopes in the GP head domain. Previously described EBOV neutralizing antibodies KZ52, 2G4, and 4G7 (Lee, et al., 2008, Nature, 454 (7201): 177-182; Murin, et al, 2014, Proc Natl Acad Sci USA, 111(48):17182-7) as well as SUDV-specific neutralizing mAb 16F6 (Dias, et al., 2011, Nat Struct Mol Bio, 18(12):1424-7) bind at the base of the GP trimer to overlapping epitopes consisting of residues from both GP2 and the base domain of GP1 (As shown in FIG. 1 for KZ52). In contrast, the cross-reactive and cross-neutralizing pan-ebolavirus mAbs (Keck, et al., 2016, J Virol, 90:279-291; Holtsberg, et al., 2016, J Virol, 90:266-278) (PCT/US15/57627 and PCT/US15/37493, both of which are incorporated herein in their entireties) appear to bind from above to either the glycan cap or the GP1 core (GP head domain) (Tables 1A, 1B, and 1C).

Tables 1A, 1B, and 1C summarize the characterization and efficacy of pan-ebolavirus antibodies. ELISA reactivity and neutralization capacity is shown. The binding regions were determined by ELISA using various domains of EBOV GP as antigen (Keck, et al., 2016, J Virol, 90:279-291; Holtsberg, et al., 2016, J Virol, 90:266-278). Binding residues were determined using the alanine scanning mutagenesis as described herein. Efficacy was tested in mice as described (Keck, et al., 2016, J Virol, 90:279-291; Holtsberg, et al., 2016, J Virol, 90:266-278). For EBOV guinea pig studies animals were infected with guinea pig adapted EBOV (GPA-EBOV) (Cross et al, 2015, J Infect Dis. 212 Suppl 2:S305-15) followed by injection of FVM04 (5 mg/animal) either on day 1 and survival monitored for 28 days. This study showed 33% protection. To test efficacy in guinea pigs against SUDV, animals were infected with guinea pig adapted Sudan virus (GPA-SUDV) (Wong et al, 2015, J Virol, 90(1):392-9). In one group FVM04 was injected at one day post infection and in another group animals were given FV04 at 3 days post infection. 100% protection was observed in both studies. CA45 testing in both EBOV and SUDV guinea pig models was performed by injecting one dose of antibody at 3 days post challenge at a dose of 5 mg. NT: not tested.

TABLE 1A

| mAb | ELISA reactivity | | | | | Neutralization | | |
|---|---|---|---|---|---|---|---|---|
| | EBOV | SUDV | BDBV | RESTV | MARV | EBOV | SUDV | BDBV |
| FVM04 | ++++ | ++++ | ++++ | ++++ | + | ++++ | ++++ | + |
| FVM09 | ++++ | ++++ | ++++ | ++++ | − | +/− | +/− | NT |
| FVM17 | ++++ | ++++ | ++++ | ++++ | − | +/− | +/− | NT |
| FVM20 | ++++ | ++ | ++++ | ++++ | − | +/− | +/− | NT |
| 4B8 | ++++ | ++++ | ++++ | ++++ | − | − | − | NT |
| m8C4 | +++ | +++ | + | − | − | ++ | ++ | NT |
| CA45 | ++++ | ++++ | ++++ | ++ | − | ++ | ++ | ++ |

TABLE 1B

| mAb | Epitope | | |
|---|---|---|---|
| | Type | Binding region | Binding residues |
| FVM04 | Conf. | Core/RBR (aa31-200) | K115, D117, G118 |
| FVM09 | Linear | Glycan Cap (aa227-313) | W288, F290, W291 |
| FVM17 | Linear | Glycan Cap (aa227-313) | E287, W288, F290, W291, K294 |
| FVM20 | Linear | Glycan Cap (aa227-313) | E287, W288, F290, W291, K294 |
| 4B8 | Conf. | Core/RBR (aa31-200) | R89, G91 |
| m8C4 | Conf. | Glycan Cap and Core | E106, R136, E258, Q251, F252 |
| CA45 | Conf. | Internal Fusion Loop | R64, Y517, G546, N550 |

TABLE 1C

| mAb | Efficacy | | | |
|---|---|---|---|---|
| | Mouse EBOV | Mouse Sudan | Guinea pig EBOV | Guinea pig SUDV |
| FVM04 | 100% | 80% | 33% | 100% |
| FVM09 | 70% | NT | NT | NT |
| FVM17 | NT | NT | NT | NT |
| FVM20 | 60% | NT | NT | NT |
| 4B8 | 100% | NT | NT | NT |
| m8C4 | 50% | 70% | NT | NT |
| CA45 | 100% | 90% | 50% | 100% |

Figure 2C:
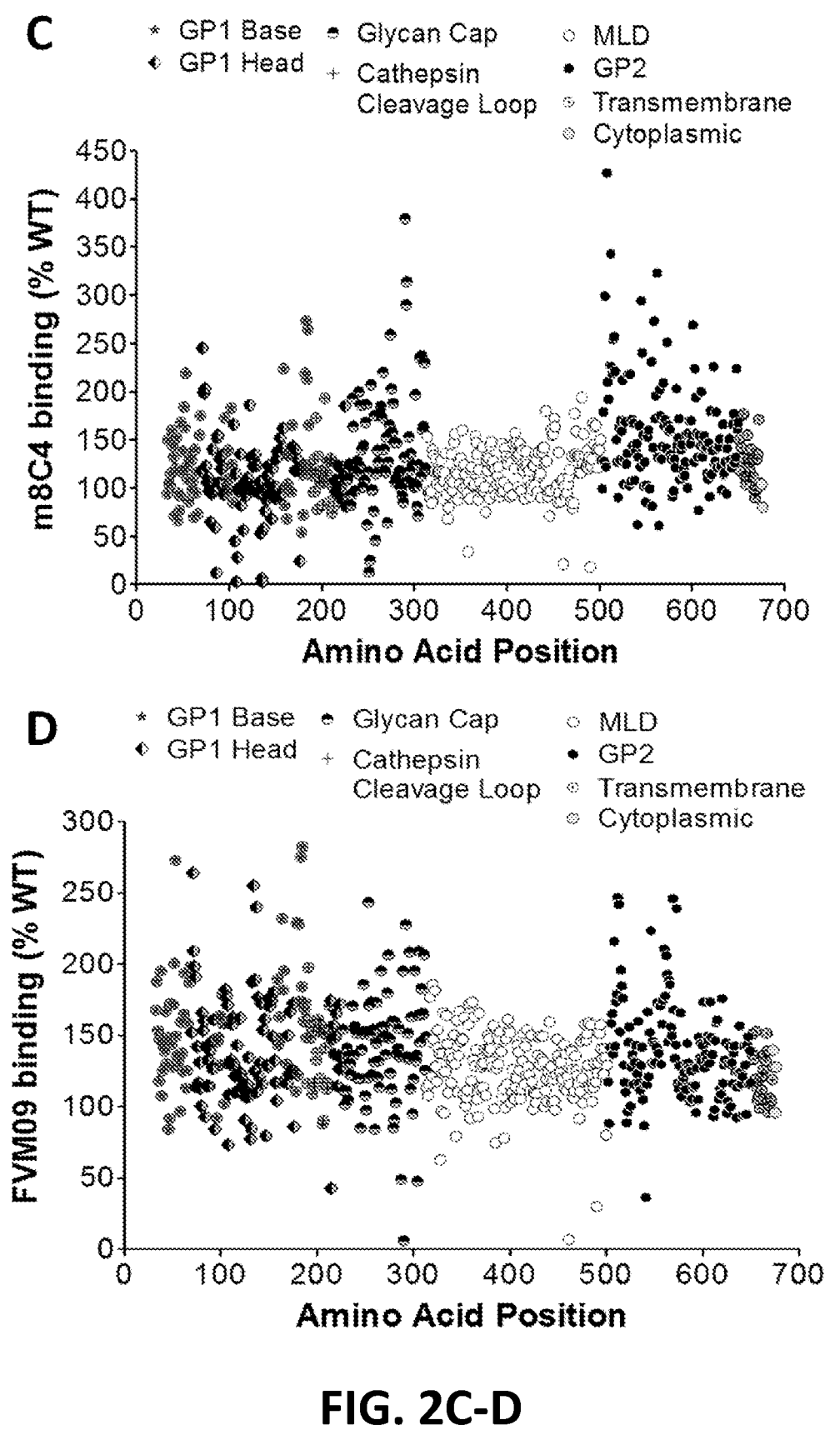

Alanine scanning experiments revealed differences between GP binding patterns. While the binding of the GP base binder KZ52 to all individual mutants remained below 150% of binding value with wild-type (wt) GP (FIG. 2A), several single alanine substitutions of GP had an enhancing effect (as high as 200-300% of the binding to wt GP) on the binding of cross-neutralizing antibody FVM04 (FIG. 2B). Out of 217 amino acids forming the base, alanine mutation of 23 residues increased FVM04 binding to GP by more than two fold (FIG. 2B and Table 2).

Table 2 shows the relative binding of individual single point alanine mutations of the residues within the base of EBOV GP to KZ52 (base binder) as compared to GP1 top binders m8C4, FVM09, FVM20, FVM17, and 4B8, as well as the fusion loop binder CA45. The binding values are shown for each mutant and each antibody, given as a percentage relative to the binding of each antibody to wild-type (wt) GP. Where the binding is elevated to 150-200% compared to wt GP the values are shown in bold font. For enhancements of more than 200% of wild-type the values are shown in bold italicized font on black background. Binding values representing mutations with reduction in binding of KZ52 to 20% or less compared to wt GP are double underlined and bold.

TABLE 2

| Mutation | KZ52 | FVM04 Binding | m8C4 Binding | FVM09 Biding | FVM17 Binding | FVM20 Binding | h4B8 Binding | CA45 Binding |
|---|---|---|---|---|---|---|---|---|
| I33A | 68 | *208* | 94 | 168 | 168 | 143 | *302* | 129 |
| P34A | 84 | *231* | 150 | 188 | 182 | 139 | *323* | 116 |
| L35A | 121 | 123 | 105 | 153 | 140 | 102 | 149 | 109 |
| G36A | 86 | 146 | 103 | 118 | 138 | 130 | 93 | 71 |
| V37A | 86 | 125 | 115 | 147 | 109 | 125 | 174 | 91 |
| I38A | 70 | *251* | 160 | 195 | 186 | 133 | *277* | 118 |
| H39A | 100 | 149 | 144 | 108 | 126 | 117 | 133 | 131 |
| N40A | 148 | 153 | 132 | 125 | 148 | 93 | 123 | 178 |
| S41A | 96 | 121 | 71 | 143 | 119 | 81 | 104 | 122 |
| T42A | 127 | 138 | 120 | 139 | 118 | 107 | 103 | 153 |
| L43A | 71 | 172 | 152 | 167 | 196 | 151 | *405* | 54 |
| Q44A | 83 | 118 | 66 | 130 | 127 | 85 | 110 | 88 |
| V45A | 88 | 102 | 95 | 149 | 117 | 100 | *253* | 147 |
| S46A | 95 | 104 | 77 | 84 | 111 | 79 | 85 | 66 |
| D47A | 98 | 106 | 92 | 92 | 76 | 83 | 99 | 64 |
| V48A | 93 | 143 | 168 | 173 | 168 | 128 | *420* | 74 |
| D49A | 115 | 114 | 117 | 144 | 114 | 98 | 49 | 69 |
| K50A | 103 | 134 | 138 | 128 | 166 | 109 | 97 | 91 |
| L51A | 98 | *201* | 184 | 172 | *218* | 161 | *480* | 88 |
| V52A | 105 | 169 | 163 | *201* | 192 | 175 | *366* | 137 |
| C53A | 50 | *256* | *219* | *273* | *251* | *224* | *578* | 122 |
| R54A | 108 | 153 | 122 | *150* | 166 | 117 | *309* | 93 |
| D55A | 97 | 118 | 109 | 136 | 124 | 123 | 78 | 83 |
| K56A | 80 | 132 | 86 | 132 | 132 | 117 | 86 | 114 |
| L57A | 95 | 163 | 129 | 135 | 134 | 159 | *254* | 59 |
| S58A | 111 | 138 | 136 | 97 | 131 | 100 | 125 | 88 |
| S59A | 116 | 105 | 129 | 159 | 81 | 94 | 97 | 99 |
| T60A | 81 | 120 | 98 | 138 | 120 | 93 | 64 | 100 |
| N61A | 118 | 130 | 107 | 125 | 118 | 123 | 127 | 103 |
| Q62A | 79 | 135 | 70 | 165 | 106 | 105 | 115 | 88 |
| L63A | 120 | 162 | 140 | 194 | 173 | 179 | *484* | 112 |
| R64A | 75 | 126 | 95 | 113 | 104 | 79 | 19 | 2 |
| S65A | 96 | 138 | 116 | 125 | 160 | 114 | 132 | 93 |
| V66A | 99 | 159 | 73 | 159 | 78 | 114 | *354* | 98 |
| L68A | 83 | *213* | 155 | 187 | 177 | 155 | *902* | 60 |
| N69A | 106 | 141 | 175 | 198 | 140 | 161 | 148 | 108 |
| K95A | 92 | 159 | 173 | 148 | 154 | 92 | 173 | 106 |
| V96A | 116 | 109 | 96 | 92 | 82 | 79 | 96 | 98 |
| V97A | 92 | 115 | 108 | 145 | 143 | 128 | 108 | 92 |
| N98A | 117 | 130 | 98 | 149 | 110 | 110 | 98 | 111 |
| Y99A | 43 | 169 | 139 | 164 | *217* | 168 | 139 | 39 |
| E100A | 116 | 135 | 98 | 129 | 129 | 105 | 98 | 123 |
| A101S | 96 | 118 | 110 | 162 | 139 | 114 | 110 | 117 |
| G102A | 52 | 148 | 183 | 178 | 189 | 166 | 183 | 76 |
| E103A | <u><u>3</u></u> | 129 | 124 | 158 | *204* | *228* | 124 | 1 |
| W104A | 84 | 124 | 85 | 102 | 122 | 94 | 85 | 72 |
| F159A | <u><u>4</u></u> | *249* | *224* | 189 | *235* | *203* | *762* | 8 |
| F160A | 61 | 108 | 82 | 143 | 141 | *150* | 111 | 65 |
| L161A | 92 | 153 | 101 | 163 | 159 | 138 | *512* | 75 |
| Y162A | 58 | 40 | 68 | 117 | 132 | 112 | 26 | 49 |
| D163A | 124 | 110 | 104 | 148 | 131 | 122 | 82 | 114 |

TABLE 2-continued

| Mutation | KZ52 | FVM04 Binding | m8C4 Binding | FVM09 Biding | FVM17 Binding | FVM20 Binding | h4B8 Binding | CA45 Binding |
|---|---|---|---|---|---|---|---|---|
| R164A | 97 | *193* | 134 | *232* | *239* | *223* | *610* | 73 |
| L165A | 103 | *158* | 136 | *182* | 146 | 126 | *247* | 128 |
| A166S | 87 | 104 | 139 | *196* | *172* | *157* | 135 | 95 |
| S167A | 92 | 127 | 96 | 118 | 108 | 92 | 45 | 85 |
| T168A | 100 | 103 | *165* | 130 | *177* | 134 | 148 | 118 |
| A177S | 96 | 110 | 122 | 125 | 135 | 104 | 26 | 90 |
| E178A | <u>8</u> | 66 | 54 | 111 | 127 | 119 | 109 | 9 |
| G179A | 65 | *193* | 114 | *229* | *203* | *179* | *822* | 56 |
| V180A | 95 | 133 | 72 | 122 | 106 | 79 | 46 | 115 |
| V181A | 86 | *230* | 124 | *228* | *314* | *271* | *916* | 64 |
| A182S | 110 | 95 | *219* | *174* | 143 | 109 | *343* | 92 |
| F183A | <u>18</u> | *306* | *273* | *275* | *282* | *264* | *1212* | 23 |
| L184A | 111 | *195* | *213* | *184* | *217* | *241* | *546* | 89 |
| I185A | 113 | *231* | *264* | *282* | *194* | 141 | *643* | 142 |
| L186A | 109 | 107 | *165* | *160* | 122 | 122 | *189* | 60 |
| P187A | 129 | *156* | 123 | *168* | 121 | 137 | *325* | 60 |
| Q188A | 99 | *156* | 119 | *173* | 118 | 88 | 93 | 121 |
| A189S | 92 | 143 | 113 | 148 | 88 | 112 | 81 | 90 |
| K190A | 108 | *151* | 119 | 116 | 115 | 132 | *187* | 33 |
| K191A | 114 | 117 | 96 | *198* | 127 | 103 | 130 | 110 |
| D192A | 122 | 134 | 130 | *161* | 85 | 90 | 95 | *170* |
| F193A | 118 | 129 | 96 | 148 | 110 | 110 | 121 | *182* |
| F194A | 96 | *167* | *173* | *156* | *163* | 85 | *178* | *224* |
| S195A | 105 | 106 | 78 | 109 | 105 | 69 | 89 | 113 |
| R498A | 65 | *213* | 121 | 141 | *193* | *177* | *295* | 56 |
| T499A | 106 | *153* | 142 | 135 | 110 | 99 | 100 | 94 |
| R500A | 77 | *178* | 140 | 80 | 116 | 111 | 114 | 65 |
| R501A | 61 | *224* | *150* | 129 | 140 | 131 | *302* | 51 |
| E502A | 99 | 145 | 129 | 117 | 83 | 92 | 68 | 92 |
| A503S | 97 | *150* | 99 | 88 | 118 | 95 | 111 | 82 |
| I504A | 73 | 99 | *179* | 142 | 113 | 138 | 94 | 95 |
| V505A | 76 | 108 | 128 | *159* | 131 | 92 | 132 | 103 |
| N506A | 93 | 142 | *299* | *165* | 149 | 136 | 89 | 105 |
| A507S | 89 | 144 | 122 | 137 | 116 | 86 | 75 | 141 |
| Q508A | 36 | 141 | *427* | *216* | *204* | 144 | *177* | 83 |
| P509A | 85 | 118 | *210* | 142 | *155* | *162* | 145 | 89 |
| K510A | 89 | *174* | *192* | *173* | *250* | *185* | 146 | 79 |
| C511A | <u>1</u> | *174* | *227* | *179* | *234* | *181* | *891* | 7 |
| N512A | 35 | *279* | *343* | *247* | *319* | *240* | *876* | 43 |
| P513A | 82 | *175* | *226* | *242* | *234* | *208* | *599* | 84 |
| N514A | 74 | 144 | *219* | *153* | *166* | *164* | *245* | 81 |
| L515A | <u>4</u> | *241* | *254* | *196* | *274* | *230* | *799* | 4 |
| H516A | 89 | *203* | *257* | *185* | *275* | *189* | *716* | 68 |
| Y517A | 70 | *188* | *221* | *176* | *226* | *163* | *659* | 4 |
| W518A | <u>3</u> | 142 | *150* | 129 | 138 | 133 | *378* | 6 |
| T519A | 104 | 100 | 127 | 117 | 107 | 120 | 73 | 140 |
| T520A | 107 | 93 | 90 | 110 | 76 | 110 | 89 | 77 |
| Q521A | 115 | 99 | *163* | 89 | 103 | 88 | 60 | 128 |
| D522A | 64 | 105 | 129 | 96 | 119 | 94 | 76 | 126 |
| E523A | 93 | 139 | *170* | 145 | 125 | 118 | 48 | 122 |
| G524A | 93 | 144 | *159* | *156* | 106 | 115 | 62 | 93 |
| A525S | 85 | 91 | *212* | 101 | 111 | 70 | 56 | 95 |
| A526S | 94 | 111 | 104 | 128 | 114 | 87 | 43 | 90 |
| I527A | 98 | 142 | 130 | 137 | 114 | 109 | 62 | 107 |
| G528A | 109 | 123 | *169* | 116 | 76 | 122 | 131 | 93 |
| L529A | 98 | 126 | 125 | 132 | 128 | 111 | 51 | 94 |
| A530S | 95 | 140 | 136 | 131 | 92 | 115 | 43 | 103 |
| W531A | 87 | *214* | *218* | 143 | 128 | 118 | 66 | 144 |
| I532A | 100 | 135 | 103 | 123 | 106 | 106 | 20 | 95 |
| P533A | 97 | *180* | *218* | *160* | 97 | 143 | 225 | 117 |
| Y534A | 72 | 120 | 107 | 117 | 94 | 95 | 23 | 140 |
| F535A | 82 | 112 | 112 | *171* | 112 | 71 | 95 | 33 | 107 |
| G536A | 112 | 119 | 144 | 129 | 141 | 99 | 43 | 82 |
| P537A | 106 | 137 | *167* | 142 | 122 | 138 | 127 | 84 |
| A538S | 114 | 122 | 108 | 105 | 87 | 94 | 52 | 107 |
| A539S | 78 | 95 | 138 | 87 | 115 | 74 | 38 | 77 |
| E540A | 91 | 111 | 146 | 116 | 95 | 76 | 83 | 99 |
| G541A | 30 | 42 | 62 | 37 | 45 | 50 | 1 | 44 |
| I542A | 72 | 114 | 132 | 116 | 95 | 89 | 24 | 98 |
| Y543A | 76 | 142 | *165* | *167* | *162* | 135 | *183* | 82 |
| I544A | 73 | 106 | 122 | 121 | 118 | 97 | 29 | 84 |
| E545A | 92 | *175* | *294* | *152* | *199* | *163* | *300* | 39 |
| G546A | 71 | *189* | *240* | *224* | *215* | *180* | *636* | 11 |

TABLE 2-continued

| Mutation | KZ52 | FVM04 Binding | m8C4 Binding | FVM09 Biding | FVM17 Binding | FVM20 Binding | h4B8 Binding | CA45 Binding |
|---|---|---|---|---|---|---|---|---|
| L547A | 80 | 106 | 155 | 131 | 134 | 126 | 53 | 88 |
| M548A | 116 | 124 | 102 | 146 | 121 | 117 | 65 | 61 |
| H549A | 78 | 130 | 127 | 130 | 80 | 118 | 105 | 73 |
| N550A | <u>3</u> | 167 | 85 | 144 | 123 | 116 | 131 | 22 |
| Q551A | 100 | 91 | 103 | 131 | 84 | 86 | 42 | 114 |
| D552A | <u>13</u> | 115 | 153 | 142 | 101 | 149 | 76 | 119 |
| G553A | <u>16</u> | 137 | 160 | 173 | 143 | 131 | 148 | 71 |
| L554A | <u>88</u> | 157 | 99 | 137 | 102 | 87 | 112 | 134 |
| C556A | <u>3</u> | 174 | *231* | 171 | 146 | 143 | *858* | 6 |
| G557A | 124 | 131 | 81 | 130 | 110 | 91 | 122 | 103 |
| L558A | 77 | 188 | 142 | 158 | 152 | 175 | *395* | 84 |
| R559A | <u>2</u> | 190 | *273* | 175 | *232* | 181 | *834* | 7 |
| Q560A | 72 | 145 | 172 | *211* | 137 | 162 | 186 | 79 |
| L561A | 40 | *278* | 196 | 178 | *224* | 140 | 139 | 113 |
| A562S | 30 | *273* | *323* | 206 | *291* | *231* | *950* | 33 |
| N563A | 96 | 139 | 132 | 193 | 138 | 130 | 186 | 72 |
| E564A | 93 | 145 | 61 | 145 | 142 | 105 | 200 | 102 |
| T565A | 26 | *214* | 202 | 189 | *258* | 200 | *720* | 79 |
| T566A | 133 | 156 | 175 | 186 | 137 | 121 | *546* | 131 |
| Q567A | 99 | 122 | 130 | 156 | 156 | 93 | 39 | 100 |
| A568S | 107 | 112 | 143 | 150 | 123 | 88 | 44 | 101 |
| L569A | 59 | *252* | 209 | 246 | *277* | 217 | *574* | 61 |
| Q570A | 101 | 173 | 165 | 168 | 110 | 161 | 269 | 109 |
| L571A | 83 | 134 | 171 | 134 | 147 | 123 | 64 | 88 |
| F572A | 102 | 121 | 141 | 144 | 120 | 117 | 54 | 90 |
| L573A | 86 | *251* | *251* | 239 | 205 | *298* | *793* | 126 |
| R574A | 87 | 131 | 165 | 117 | 117 | 96 | 58 | 86 |
| A575S | 96 | 111 | 159 | 113 | 113 | 108 | 27 | 70 |
| T576A | 121 | 159 | 161 | 129 | 133 | 115 | 137 | 90 |
| T577A | 104 | 141 | 135 | 166 | 106 | 106 | 107 | 84 |
| E578A | 110 | 119 | 130 | 107 | 104 | 115 | 116 | 80 |
| L579A | 97 | 148 | 91 | 117 | 89 | 106 | 52 | 53 |
| R580A | 101 | 167 | 97 | 120 | 123 | 101 | 34 | 86 |
| T581A | 93 | 135 | 130 | 124 | 141 | 101 | 197 | 135 |
| F582A | 98 | 121 | 121 | 112 | 115 | 137 | 56 | 105 |
| S583A | 126 | 129 | *203* | 131 | 145 | 98 | 206 | 116 |
| I584A | 107 | 153 | 144 | 144 | 148 | 129 | 102 | 121 |
| L585A | 81 | 155 | 152 | 131 | 108 | 98 | 69 | 90 |
| N586A | 108 | 134 | 172 | 127 | 109 | 109 | 93 | 100 |
| R587A | 97 | 124 | 109 | 103 | 102 | 97 | 50 | 85 |
| K588A | 105 | 167 | 140 | 125 | 106 | 122 | 74 | 75 |
| A589S | 96 | 157 | 145 | 106 | 73 | 121 | 39 | 115 |
| I590A | 88 | 122 | 113 | 115 | 118 | 98 | 30 | 90 |
| D591A | 96 | 123 | 120 | 114 | 89 | 112 | 142 | 135 |
| F592A | 108 | 126 | 113 | 115 | 120 | 62 | 66 | 77 |
| L593A | 100 | 107 | 127 | 96 | 96 | 103 | 67 | 80 |
| L594A | 88 | 187 | 156 | 127 | 115 | 107 | 68 | 72 |
| Q595A | 92 | 117 | 100 | 105 | 129 | 96 | 123 | 151 |
| R596A | 106 | 97 | 157 | 149 | 93 | 101 | 125 | 102 |
| W597A | 97 | 118 | 170 | 134 | 116 | 91 | 40 | 79 |
| G598A | 72 | 111 | 146 | 144 | 135 | 144 | 137 | 95 |
| G599A | 86 | 136 | 170 | 132 | 137 | 136 | 60 | 98 |
| T600A | 99 | 163 | 155 | 143 | 148 | 109 | 88 | 98 |
| C601A | 78 | *210* | 269 | 174 | *268* | 127 | *669* | 105 |
| H602A | 106 | 130 | 127 | 127 | 116 | 82 | 105 | 94 |
| I603A | 102 | 128 | *224* | 137 | 130 | 147 | 167 | 97 |
| L604A | 94 | 135 | 194 | 133 | 131 | 132 | 204 | 124 |
| G605A | 88 | 131 | 157 | *150* | 152 | 163 | 226 | 104 |
| P606A | 110 | 114 | 132 | 146 | 140 | 108 | 197 | 78 |
| D607A | 95 | 107 | 77 | 131 | 129 | 79 | 114 | 90 |
| C608A | 43 | 181 | 155 | 174 | 127 | 137 | *741* | 56 |
| C609A | 22 | *205* | 144 | 149 | 178 | 191 | *868* | 27 |
| I610A | 83 | 183 | 200 | 137 | 181 | 168 | *588* | 74 |
| E611A | 87 | 123 | 132 | 93 | 136 | 107 | 186 | 98 |
| P612A | 89 | 137 | 147 | 98 | 128 | 70 | 147 | 95 |
| H613A | 103 | 178 | 154 | 146 | 98 | 176 | 41 | 89 |
| D614A | 89 | 142 | 141 | 159 | 158 | 138 | *361* | 147 |
| W615A | 85 | 135 | 143 | 161 | 151 | 132 | 162 | 102 |
| T616A | 126 | 136 | 115 | 105 | 123 | 151 | 278 | 105 |
| K617A | 97 | 132 | 109 | 105 | 107 | 101 | 90 | 85 |
| N618A | 101 | 125 | 147 | 112 | 118 | 131 | 141 | 132 |
| I619A | 108 | 111 | 91 | 109 | 92 | 82 | 50 | 123 |
| T620A | 117 | 139 | 180 | 176 | 197 | 97 | 151 | 152 |
| D621A | 116 | 126 | 114 | 117 | 121 | 77 | 87 | 99 |

TABLE 2-continued

| Mutation | KZ52 | FVM04 Binding | m8C4 Binding | FVM09 Biding | FVM17 Binding | FVM20 Binding | h4B8 Binding | CA45 Binding |
|---|---|---|---|---|---|---|---|---|
| K622A | 99 | 89 | 139 | 129 | 127 | 83 | 119 | 125 |
| I623A | 93 | 99 | *343* | 133 | 124 | 112 | 21 | 106 |
| D624A | 104 | 127 | 124 | 145 | 154 | 128 | 194 | 90 |
| Q625A | 90 | 117 | 128 | 95 | 85 | 111 | 64 | 103 |
| I626A | 83 | 150 | 179 | 104 | 101 | 83 | 29 | 124 |
| I627A | 98 | 134 | 121 | 130 | 116 | 113 | 50 | 122 |
| H628A | 84 | 143 | 141 | 142 | 66 | 115 | 74 | 94 |
| D629A | 102 | 129 | 143 | 100 | 57 | 96 | 94 | 4 |
| F630A | 76 | 121 | 151 | 131 | 110 | 90 | 18 | 105 |
| V631A | 96 | 122 | 123 | 116 | 115 | 94 | 55 | 105 |
| D632A | 104 | 131 | 98 | 138 | 102 | 160 | 187 | 97 |
| K633A | 98 | 138 | 166 | 143 | 150 | 141 | 146 | 94 |
| T634A | 82 | 168 | 114 | 125 | 150 | 118 | 100 | 89 |
| L635A | 87 | 101 | 116 | 92 | 101 | 87 | 87 | 123 |
| P636A | 86 | 130 | 127 | 114 | 130 | 133 | 95 | 73 |
| D637A | 88 | 100 | 94 | 124 | 81 | 111 | 73 | 104 |
| Q638A | 113 | 132 | 141 | 157 | 125 | 145 | 65 | 84 |
| G639A | 86 | 115 | 151 | 124 | 123 | 107 | 91 | 97 |
| D640A | 105 | 113 | 151 | 116 | 148 | 102 | 101 | 82 |
| N641A | 84 | 104 | 129 | 121 | 109 | 93 | 85 | 78 |
| D642A | 101 | 106 | 121 | 94 | 99 | 113 | 86 | 99 |
| N643A | 106 | 106 | 121 | 143 | 117 | 115 | 91 | 83 |
| W644A | 107 | 105 | 166 | 129 | 86 | 88 | 77 | 114 |
| W645A | 99 | 130 | 177 | 95 | 118 | 119 | 68 | 126 |
| T646A | 102 | 151 | 126 | 143 | 130 | 122 | 86 | 107 |
| G647A | 92 | 137 | 132 | 149 | 97 | 110 | 77 | 84 |
| W648A | 66 | 107 | *224* | 116 | 98 | 73 | 61 | 95 |
| R649A | 85 | 112 | 161 | 139 | 90 | 96 | 66 | 101 |
| Q650A | 120 | 136 | 168 | 117 | 109 | 103 | 104 | 110 |

These mutants included both C53 and C609 that form a disulfide bond between GP1 and GP2. The majority of these residues are hydrophobic, highly networked, and not surface exposed (Table 3). In addition to the 23 base residues, mutation of R498 and R501, within the furin cleavage site separating GP1 and GP2, also led to an over two fold increase in FVM04 binding (FIG. 2B and Table 3).

Table 3: Single alanine substitution within the EBOV GP base that increase FVM04 binding by more than 200% as compared to wild type EBOV GP. Percent binding is also shown for the same mutants to m8C4, FVM09, FVM20, and 4B8. All values greater than 200% are double underlined. Values are average of 2 or 3 experiments±standard error defined as half the difference between maxim and minimum for each replicate.

TABLE 3

| | | % binding compared to wt GP | | | | |
|---|---|---|---|---|---|---|
| Mutant | Position in GP structure | FVM04 | m8C4 | FVM09 | FVM20 | 4B8 |
| I33A | Buried | 208 ±16 | 94 ± 30 | 168 ± 10 | 143 ± 15 | 302 ±5 |
| P34A | Buried | 231 ±40 | 150 ± 40 | 188 ± 68 | 139 ± 12 | 323 ±20 |
| I38A | Buried | 251 ±45 | 160 ± 21 | 195 ± 4 | 133 ± 1 | 277 ±18 |
| L51A | Surface exposed | 201 ±8 | 184 ± 46 | 172 ± 6 | 161 ± 22 | 480 ±46 |
| C53A | Buried; Disulfide bond with C609 | 256 ±18 | 219 ±2 | 273 ±14 | 224 ±33 | 578 ±30 |
| L68A | Buried | 213 ±28 | 155 ± 30 | 187 ± 12 | 155 ± 5 | 902 ±5 |
| E71A | Surface exposed | 238 ±2 | 245 ±18 | 264 ±5 | 269 ±2 | 780 ±73 |
| F159A | Buried | 249 ±11 | 224 ±2 | 189 ± 15 | 203 ±4 | 762 ±28 |
| V181A | Buried | 230 ±5 | 124 ± 35 | 228 ±7 | 271 ±14 | 916 ±40 |
| F183A | Buried | 306 ±45 | 273 ±3 | 275 ±18 | 264 ±20 | 1212 ±80 |
| I185A | Buried | 231 ±15 | 264 ±0 | 282 ±2 | 141 ± 5 | 643 ±237 |
| R498A | Furin cleavage site | 213 ±39 | 121 ± 0 | 141 ± 3 | 177 ± 27 | 295 ±74 |
| R501A | Furin cleavage site | 224 ±12 | 150 ± 25 | 129 ± 10 | 131 ± 35 | 302 ±53 |
| N512A | Surface exposed | 279 ±9 | 343 ±65 | 247 ±19 | 240 ±32 | 876 ±208 |
| L515A | Buried | 241 ±27 | 254 ±9 | 196 ± 15 | 230 ±3 | 799 ±39 |
| H516A | Surface exposed | 203 ±11 | 257 ±13 | 185 ± 2 | 189 ± 54 | 716 ±9 |
| W531A | Surface exposed | 214 ±0 | 218 ±28 | 143 ± 4 | 118 ± 7 | 66 ± 8 |
| L561A | Buried | 278 ±21 | 196 ± 2 | 178 ± 23 | 140 ± 43 | 139 ± 26 |
| A562S | Buried | 273 ±23 | 323 ±22 | 206 ±22 | 231 ±9 | 950 ±132 |
| T565A | Buried | 214 ±54 | 202 ±49 | 189 ± 20 | 200 ±25 | 720 ±235 |
| L569A | Buried | 252 ±19 | 209 ±34 | 246 ±20 | 217 ±37 | 574 ±10 |
| L573A | Buried | 251 ±17 | 251 ±1 | 239 ±17 | 298 ±11 | 793 ±195 |
| C601A | Not resolved in crystal structure | 210 ±13 | 269 ±6 | 174 ± 0 | 127 ± 9 | 669 ±194 |

TABLE 3-continued

| Mutant | Position in GP structure | % binding compared to wt GP | | | | |
|---|---|---|---|---|---|---|
| | | FVM04 | m8C4 | FVM09 | FVM20 | 4B8 |
| C609A | Not resolved in crystal structure; Disulfide bond with C53 | <u>205 ±27</u> | 144 ± 1 | 149 ± 2 | 191 ± 5 | <u>868 ±127</u> |

These data demonstrate that minor structural modifications within the GP base can have a significant impact on the accessibility of the FVM04 epitope and possibly other cross-reactive and neutralizing epitopes within the conserved regions of the GP1 head domain. They indicate that the exposure of cross-reactive epitopes can be modulated by mutations in the GP base and could have major implications for development of pan-ebolavirus vaccines.

In addition, many of these single residue alanine substitutions that increased binding to FVM04 also increased binding of GP to other antibodies that bind to the top of GP trimer, which have reported previously (Keck, et al., 2016, *J Virol*, 90:279-291; Holtsberg, et al., 2016, *J Virol*, 90:266-278). As shown in Table 2, a number of mutations were identified that increase the binding of most or all of these top binders. These data indicate that certain GP base mutations have a global effect on the exposure of cross-reactive epitopes.

Figure 2G:
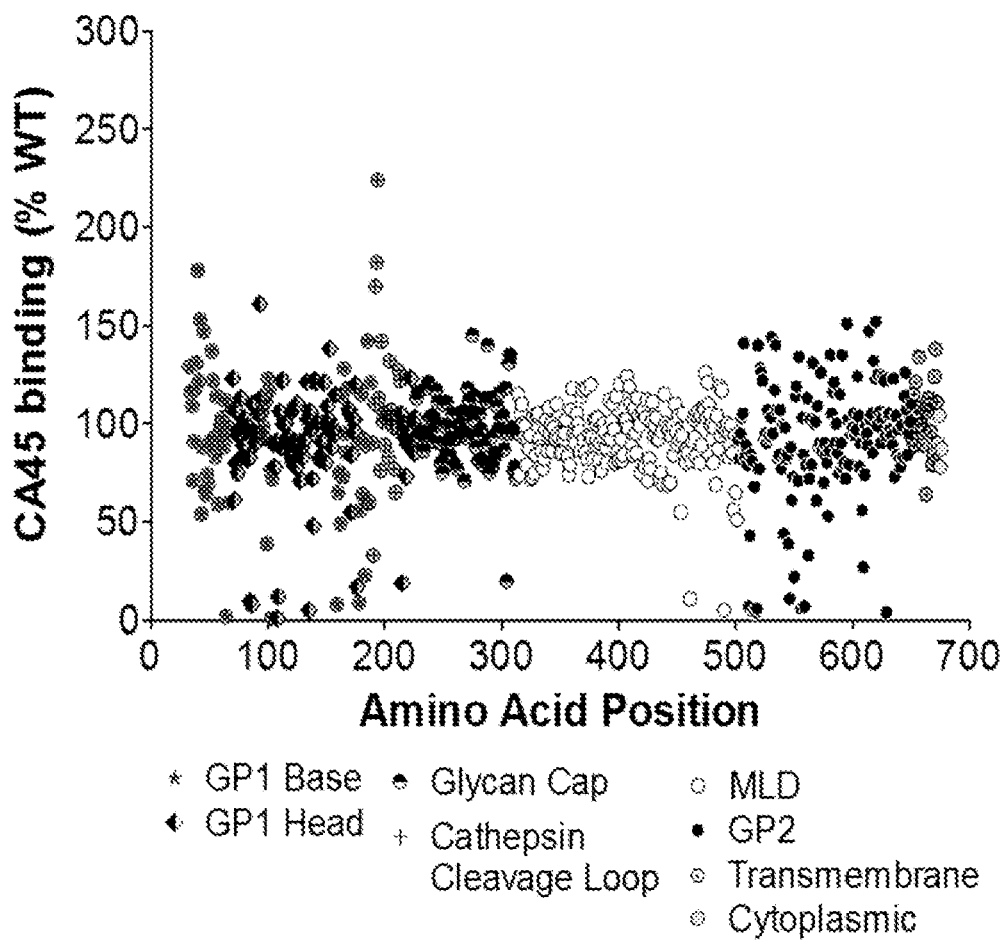
FIG. 2G shows binding of antibodies to the EBOV GP library. Shown are the binding values, relative to binding with wild-type GP, of all EBOV GP single alanine substitution library mutants with pan-ebolavirus antibody CA45 (G).

Another pan-ebolavirus antibody, CA45, was discovered to bind to a phylogenetically conserved epitope within the internal fusion loop of ebolaviruses (U.S. Provisional Patent No. 62/406,598). Using alanine scanning mutagenesis the specific contact sites for CA45 in EBOV GP were shown to be R64 in the N-terminal base domain of GP1 and Y517, G546, and N550 in GP2 (Table 1). The alanine scanning mutagenesis data for CA45 also identified several GP residues that enhance the exposure and binding of CA45 (FIG. 2G). These residues are shown in Table 2.

Example 3

It was observed that substitutions in three out four glycosylation sites within the glycan cap increased the binding of the cross-reactive antibody FVM04. Shotgun mutagenesis epitope mapping identified EBOV GP residues K115, D117, and G118 as critical for FVM04 binding (FIG. 3). Alanine substitutions at these residues reduced FVM04 binding to 29%, 1%, and 2% of wild-type respectively, suggesting that these residues constitute contact sites for FVM04, with D117 and G118 having the greatest energetic contribution to FVM04 binding (FIGS. 3A and 3B). In contrast, binding of two other pan-ebolavirus antibodies FVM02 and FVM09 (Keck, et al., 2016, *J Virol*, 90:279-291) were not affected by these mutations (FIG. 3B). The putative epitope of FVM04 is positioned in a previously described region with a crest and trough morphology (Hashiguchi, et al., 2015, *Cell*, 160, 904-912; Bornholdt et al, 2016, *MBio*, In Press; Wang et al, 2016, Cell, 164 (1-2): 258-68) within the receptor binding site and constitutes the tip of the hydrophilic crest, which interacts with a loop from the endosomal filovirus receptor NPC1 (31). The three putative FVM04 contact residues of GP are 100% conserved across all ebolaviruses (FIG. 3C).

Individual alanine mutation of 3 out of four glycosylation sites (N238, N257, N268) on EBOV glycan cap led to an increase in FVM04 binding (FIG. 4). When the threonine residues two amino acids C-terminal to these glycosylation sites were mutated, the same enhancing effect was observed. These threonines are part of the recognition site for N-glycosylation, further suggesting that the observed effect is due to loss of glycosylation rather than other conformational effects. Thus, the glycosylation sites in the glycan cap of a filovirus GP can be mutated individually or in combination to increase exposure of FVM04 site. Such mutants are expected to induce other cross-neutralizing antibodies. Target residues include: N238, T240, N257, T259, N268, and T270.

Example: 4

It was observed that several cross-neutralizing GP antibodies bind better to $GP_{CL}$ that to full length GP. In ELISA, CA45 bound to $GP_{CL}$ with an EC50 of 0.06 nM compared to an EC50 of 1.4 nM for binding to full length GP ectodomain (GPΔTM), representing a 24-fold enhanced binding to $GP_{CL}$ (Table 4). Biolayer interferometry showed that CA45, while binding to $GP_{CL}$ GPΔTM with the same rate, exhibits over 1000 fold slower dissociation rate. As a result CA45 binds $GP_{CL}$ with a dissociation constant (KD) of <6 pM while CA45 KD for GPΔTM is 10.6 nM (Table 4) representing >1700 fold increased binding affinity.

Table 4: Binding kinetics, determined by Biolayer Interferometry, and ELISA binding EC50 values for binding of CA45 to full length G ectodomain (GPΔTM) compared to binding to thermolysin-cleaved GP ($GP_{CL}$). $K_{on}$: association rate, $K_{off}$: dissociation rate, $K_D$: dissocitation constant. EC50: concentration of the antibody that leads to 50% maximal binding to GP.

TABLE 4

| | $K_{on}$ | $K_{off}$ | $K_D$ | ELISA $EC_{50}$ |
|---|---|---|---|---|
| GPΔTM | (1.3 ± 0.1) × 10$^4$/M sec | (1.4 ± 0.1) × 10$^{-4}$/sec | 10.6 nM | 1.41 nM |
| $GP_{CL}$ | (1.6 ± 0.1) × 10$^4$/M sec | <1 × 10$^{-7}$/sec | <6 pM | 0.06 nM |

Example 5

Mutations in the Base of GP that Increase Binding of Antibodies Such as CA45 to the Fusion Loop Region of GP To test if base mutations widen the breadth of antibody response, several base mutations identified in Table 2 were incorporated into a VSV virus in which the VSV G protein was replaced by EBOV GPΔmuc protein produced mutant viruses. VSV-GPΔmuc and the mutants were used to immunize mice at 100 pfu by i.p. injection. Immune sera were collected after 28 days and tested for reactivity to GP from EBOV, SUDV, BDBV, and RESTV. As shown in FIG. 8, the base mutants W531A and L561A induced significantly elevated heterologous response to SUDV, BDBV, and RESTV (as much as 30 fold higher than GPdeltamuc alone). P34A also increased the response to BDBV and RESTV but dampened the anti-SUDV titers. In contrast P573A mutation did not impact the breadth of the antibody response. A mutant in which three of the GC glycans were mutated showed a 10-fold higher heterologous response to SUDV and BDBV (FIG. 8). Taken together, these data support the hypothesis that mutating specific residues within the trimer base can enhance the magnitude of the heterologous response.

Example 6

Exemplary Anti-Filovirus Glycoprotein Antibodies

This Example lists examples of anti-Filovirus glycoprotein antibodies.
Antibodies Binding to the Receptor Binding Site (RBS) of Ebolavirus:

FVM04: FVM04 is a macaque-human chimeric monoclonal antibody that binds to an exposed epitope within the RBS of multiple ebolaviruses including the virulent strains Ebola virus (EBOV), Sudan virus (SUDV), and Bundibugyo virus (BDBV). See PCT Application No. PCT/US15/57627. In order to define the epitope recognized by FVM04 we employed a comprehensive alanine scanning approach, where FVM04 binding was evaluated against a 'shotgun mutagenesis' mutation library of EBOV GP with 641 of 644 target residues individually mutated. Human HEK-293T cells were transfected with the entire mutation library in a 384-well array format (one clone per well) and assessed for reactivity to FVM04 using high-throughput flow cytometry. The method for shotgun mutagenesis is described in patent application 61/938,894 and (Davidson, E., and Doranz, B. J., 2014, Immunology, 143, 13-20). The shotgun mutagenesis revealed that FVM04 contact sites included K115, D117, and G118. This is located within a hydrophilic region of the RBS known as the Crest ((Hashiguchi, et al., 2015, Cell, 160, 904-912; Wang et al, 2016, Cell, 164 (1-2): 258-68). This epitope is conserved across all ebolaviruses. FVM04 is also weakly reactive to marburgvirus glycoprotein (PCT/US15/57627; Keck, et al., 2015, J Virol, 90:279-291 ("Keck et al.")).

FVM04 neutralizes EBOV and SUDV (PCT/US15/57627; Keck et al.), as well as BDBV and protects mice and guinea pigs against lethal EBOV and SUDV infection (see below).
Antibodies that Bind to the Glycan Cap:

13C6FR1: Monoclonal antibody 13C6 was developed using mouse hybridoma technology and was shown to protect mice from lethal challenge with Ebola virus (Wilson et al, 2000, Science, 287(5458):1664-6). 13C6 binds on the top of EBOV GP glycan cap (Murin, et al., 2014, Proc Natl Acad Sci USA, 111(48):17182-7) with contact residues being T270 and K272 (Davidson et al., 2015, J Virol., 89(21):10982-9). 13C6FR1, a variant of 13C6 (U.S. Pat. No. 7,335,356), is a component of the ZMAPP™ therapeutic cocktail (Qiu, et al., 2014, Nature, 514(7520):47-53). Effective neutralization of EBOV by 13C6 requires the presence of complement (Wilson et al, 2000, Science, 287(5458): 1664-6).

FVM09: FVM09 binds with high affinity to a linear epitope within the disordered loop connecting the β strands 17 and 18 in the glycan cap region of EBOV GP (PCT/US15/57627; Keck et al.). Using overlapping peptide mapping we mapped the epitope for FVM09 to amino acids 286-290 (GEWAF) of EBOV GP, and this epitope is 100% conserved among all ebolaviruses (PCT/US15/57627; Keck et al.).

FVM09 alone does not neutralize or provide protection in vivo against EBOV, but in combination with several other antibodies it enhances their neutralizing and protective potency as described in (Keck et al.) and below.

ADI-15731: The ADI-15731 mAb was derived from a human survivor (subject 45) of the 2014 Ebola virus outbreak (Bornholdt, et al., 2016, Science, pii:aad5788. [Epub ahead of print] "Bornholdt et al."). Negative stain electron microscopy reconstructions of the ADI-15731 fab bound to EBOV GP showed that ADI-15731 bound directly to the GP1 glycan cap structure in a manner reflective of 13C6 (Murin, et al, 2014, Proc Natl Acad Sci USA, 111(48): 17182-7 and Bornholdt et al.). However unlike 13C6, ADI-15731 binds to EBOV GP, BDBV GP and SUDV GP. ADI-15731 only effectively neutralizes vesicular stomatitis virus (VSV) pseudovirions displaying either EBOV GP or BDBV GP (as determined by the rVSV GP-GFP assay described in Example 1).
Antibodies that Simultaneously Bind to Glycan Cap and Core of GP1 m8C4: Mouse monoclonal antibody m8C4 cross neutralizes EBOV and SUDV and provides partial protection against both viruses in mice (PCT Publication No. WO2015/200522; Holtsberg, et al., 2015, J Virol, 90:266-278). Efficacy of m8C4 was enhanced when used in combination with FVM09 (PCT Publication No. WO2015/200522; PCT/US15/57627; Keck et al.). In order to define the epitope recognized by m8C4 we employed a comprehensive alanine scanning approach, where m8C4 binding was evaluated against a 'shotgun mutagenesis' mutation library of EBOV GP with 641 of 644 target residues individually mutated. Human HEK-293T cells were transfected with the entire mutation library in a 384-well array format (one clone per well) and assessed for reactivity to m8C4 using high-throughput flow cytometry. The method for shotgun mutagenesis is described in patent application 61/938,894 and (Davidson, E., and Doranz, B. J., 2014, Immunology, 143, 13-20). Shotgun mutagenesis epitope mapping identified EBOV GP residues R136, Q251, and F252 as critical for m8C4 binding. Of these residues, Q251 and F252 are located within the glycan cap, while R136 is located within the core GP1 head domain (FIG. 2). m8C4 bridges the core GP1 region with the glycan cap, and the epitope is conserved across ebolaviruses.

ADI-15750: ADI-15750 was derived from a human survivor (subject 45) of the 2014 Ebola virus outbreak (Bornholdt et al.). ADI-15750 can compete for binding with 13C6 and binds with high affinity to a quaternary epitope in the EBOV GP1 structure also present on EBOV soluble GP (sGP). ADI-15750 demonstrated neutralization activity against VSV pseudoviruses displaying either EBOV GP or SUDV GP with IC50 values of 8.80 nM and 32.30 nM, respectively (as determined by the rVSV GP-GFP assay described in Example 1).

ADI-15968: ADI-15968 was derived from a human survivor (subject 45) of the 2014 Ebola virus outbreak (Bornholdt et al.). ADI-15968 can compete for binding with 13C6 and binds with high affinity to a quaternary epitope in the EBOV GP1 structure also present on EBOV sGP. ADI- 15968 demonstrated neutralization activity against VSV pseudoviruses displaying either EBOV GP or SUDV GP with IC50 values of 11.74 nM and 47.30 nM respectively (as determined by the rVSV GP-GFP assay described in Example 1).

Antibodies that Bind to GP1/GP2 Base Epitope (Base Binders)

2G4 and 4G7: The most studied EBOV neutralizing epitope is in a region at the base of the trimeric GP that involves contact sites within GP1 and GP2. Antibodies such as KZ52 (Maruyama, et al., J. Virol. 1999; 73:6024-6030), as well as two of ZMAPP™ components 2G4 and 4G7 bind to this region (Lee, et al., 2008, Nature, 454 (7201): 177-182; Murin, et al, 2014, Proc Natl Acad Sci USA, 111(48): 17182-7). The epitopes for 2G4 and 4G7 are largely overlapping Davidson et al., 2015, J Virol., 89(21):10982-9) but the angle of binding for these two antibodies is different.

2G4 and 4G7 were shown to provide significant protection in mice and guinea pig models of EBOV infection (Qiu, et al., 2012, PLoS Negl Trop Dis, 6: 1575). Both of these antibodies, along with 13C6FR1, are components of the ZMAPP™ antibody cocktail (Qiu, et al., 2014, Nature, 514(7520):47-53). 2G4 and 4G7 are specific to EBOV and do not cross react with other filovirus glycoproteins.

ADI-15734: ADI-15734 was derived from a human survivor (subject 45) of the 2014 Ebola virus outbreak (Bornholdt et al.). ADI-15734 binds specifically to the EBOV GP and directly competes with KZ52. ADI-15734 neutralizes EBOV (as determined by the rVSV GP-GFP assay described in Example 1) and provides significant levels of protection in the EBOV murine model.

Antibodies that Bind the Fusion Loop

FVM02 (also called FVM02p): FVM02 is a macaque-derived panfilovirus antibody that binds to the tip of the internal fusion loop (IFL) of all ebolaviruses and marburgvirus (IBT PCT/US15/57627; Keck et al.). FVM02 provides partial protection against EBOV and MARV and potentiates the efficacy of FVM09 against EBOV in mouse models (IBT PCT/US15/57627; Keck et al.).

CA45: CA45 is a macaque-derived panfilovirus antibody that binds to the ebolavirus GP IFL across four different species of ebolavirus, EBOV, SUDV, RESTV, and BDBV (U.S. Provisional Application No. 62/406,598).

Antibodies that Bind Between the Tip of the Fusion Loop and the Base GP1/GP2 Epitope:

ADI-15742: The ADI-15742 mAb was derived from a human survivor (subject 45) of the 2014 Ebola virus outbreak (Bornholdt et al.). ADI-15742 is an ultra-potent pan-ebolavirus neutralizing antibody demonstrating sub-nanomolar IC50 values against VSV pseudovirions displaying GP from the following species: EBOV, BDBV, SUDV, RESTV and TAFV (as determined by the rVSV GP-GFP assay described in Example 1). ADI-15742 also provides complete protection against either EBOV or SUDV in their respective murine models.

ADI-15878: The ADI-15878 mAb was derived from a human survivor (subject 45) of the 2014 Ebola virus outbreak and is a clonal relative of ADI-15742 (Bornholdt et al.). ADI-15878 is also an ultra-potent pan-ebolavirus neutralizing antibody demonstrating sub-nanomolar IC50 values against VSV pseudovirions displaying GP from the following species: EBOV, BDBV, SUDV, RESTV and TAFV (as determined by the rVSV GP-GFP assay described in Example 1). ADI-15878 showed significant levels of protection against EBOV and complete protection against SUDV in their respective murine models.

ADI-15946: The ADI-15946 mAb was derived from a human survivor (subject 45) of the 2014 Ebola virus outbreak (Bornholdt et al.). ADI-15946 is a potent pan-ebolavirus neutralizing antibody demonstrating sub-nanomolar IC50 values against VSV pseudovirions displaying GP from the following species: EBOV, BDBV, and SUDV (as determined by the rVSV GP-GFP assay described in Example 1).

Antibodies that Bind to the Viral Membrane Proximal (Stalk) Region of Filovirus Glycoprotein:

ADI-16061: ADI-16061 is a human mAb was derived from a human survivor (subject 45) of the 2014 Ebola virus outbreak (Bornholdt et al.). ADI-16061 binds to the heptad repeat 2 helices in the stalk region of EBOV GP, BDBV GP, and SUDV GP. However, ADI-16061 only effectively neutralizes VSV pseudovirions displaying GP from EBOV and BDBV with IC50 values 0.21 nM and 0.59 nM, respectively (as determined by the rVSV GP-GFP assay described in Example 1). Further ADI-16061 provided significant levels of protection from EBOV in the murine infection model post infection.

ADI-15974, ADI-15956, and ADI-15758: ADI-15974, ADI-15956, and ADI-15758 are clonally related human mAbs derived from a human survivor (subject 45) of the 2014 Ebola virus outbreak (Bornholdt et al.). These mAbs bind to the heptad repeat 2 helices in the stalk region of EBOV GP and BDBV GP. All three mAb effectively neutralize VSV pseudovirions displaying GP from EBOV and BDBV with sub-nanomolar IC50 values. In PRNT assays ADI-15974 ADI-15956, and ADI-15758 potently neutralize EBOV (as determined by the rVSV GP-GFP assay described in Example 1) and provided significant levels of protection from EBOV in the murine infection model post infection.

ADI-15848: ADI-15848 is a human mAb derived from a human survivor (subject 45) of the 2014 Ebola virus outbreak (Bornholdt et al.). ADI-15848 binds to the heptad repeat 2 helices in the stalk region of EBOV GP and BDBV GP. ADI-15848 effectively neutralizes VSV pseudovirions displaying GP from EBOV and BDBV with IC50 values 0.50 nM and 0.77 nM, respectively (as determined by the rVSV GP-GFP assay described in Example 1). In plaque reduction neutralization (PRNT) assays ADI-15848 potently neutralized EBOV and provided significant levels of protection from EBOV in the murine infection model post infection.

ADI-16021: ADI-16021 is a human mAb derived from a human survivor (subject 45) of the 2014 Ebola virus outbreak (Bornholdt et al.). ADI-16021 binds to the heptad repeat 2 helices in the stalk region of EBOV GP, BDBV GP and SUDV GP.

The breadth and scope of the present disclosure should not be limited by any of the above-described exemplary embodiments, but should be defined only in accordance with the following claims and their equivalents.

Ebolavirus GP Sequences:

SEQ ID NO: 1: Ebola virus (Mayinga strain) glycoprotein (Genbank Acc# AF086833):
MGVTGILQLPRDRFKRTSFFLWVIILFQRTFSIPLGVIHNSTLQVSDVDKLVCRDKLS

STNQLRSVGLNLEGNGVATDVPSATKRWGFRSGVPPKVVNYEAGEWAENCYNLEI

KKPDGSECLPAAPDGIRGFPRCRYVHKVSGTGPCAGDFAFHKEGAFFLYDRLASTV

IYRGTTFAEGVVAFLILPQAKKDFFSSHPLREPVNATEDPSSGYYSTTIRYQATGFGT

NETEYLFEVDNLTYVQLESRFTPQFLLQLNETIYTSGKRSNTTGKLIWKVNPEIDTTI

GEWAFWETKKNLTRKIRSEELSFTVVSNGAKNISGQSPARTSSDPGTNTTTEDHKIM

ASENSSAMVQVHSQGREAAVSHLTTLATISTSPQSLTTKPGPDNSTHNTPVYKLDIS

EATQVEQHHRRTDNDSTASDTPSATTAAGPPKAENTNTSKSTDFLDPATTTSPQNH

SETAGNNNTHHQDTGEESASSGKLGLITNTIAGVAGLITGGRRTRREAIVNAQPKCN

PNLHYWTTQDEGAAIGLAWIPYFGPAAEGIYIEGLMHNQDGLICGLRQLANETTQA

LQLFLRATTELRTFSILNRKAIDFLLQRWGGTCHILGPDCCIEPHDWTKNITDKIDQII

HDFVDKTLPDQGDNDNWWTGWRQWIPAGIGVTGVIIAVIALFCICKFVF

SEQ ID NO: 2: Delta mucin Ebola virus (Mayinga strain) glycoprotein:
MGVTGILQLPRDRFKRTSFFLWVIILFQRTFSIPLGVIHNSTLQVSDVDKLVCRDKLS

STNQLRSVGLNLEGNGVATDVPSATKRWGFRSGVPPKVVNYEAGEWAENCYNLEI

KKPDGSECLPAAPDGIRGFPRCRYVHKVSGTGPCAGDFAFHKEGAFFLYDRLASTV

IYRGTTFAEGVVAFLILPQAKKDFFSSHPLREPVNATEDPSSGYYSTTIRYQATGFGT

NETEYLFEVDNLTYVQLESRFTPQFLLQLNETIYTSGKRSNTTGKLIWKVNPEIDTTI

GEWAFWETKKNLTRKIRSEELSFTVVSHHQDTGEESASSGKLGLITNTIAGVAGLIT

GGRRTRREAIVNAQPKCNPNLHYWTTQDEGAAIGLAWIPYFGPAAEGIYIEGLMHN

QDGLICGLRQLANETTQALQLFLRATTELRTFSILNRKAIDFLLQRWGGTCHILGPD

CCIEPHDWTKNITDKIDQIIHDFVDKTLPDQGDNDNWWTGWRQWIPAGIGVTGVII

AVIALFCICKFVF

SEQ ID NO: 3: Ebola virus (Kikwit strain) glycoprotein (Genbank Acc# KU182909):
MGVTGILQLPRDRFKRTSFFLWVIILFQRTFSIPLGVIHNSTLQVSDVDKLVCRDKLS

STNQLRSVGLNLEGNGVATDVPSATKRWGFRSGVPPKVVNYEAGEWAENCYNLEI

KKPDGSECLPAAPDGIRGFPRCRYVHKVSGTGPCAGDFAFHKEGAFFLYDRLASTV

IYRGTTFAEGVVAFLILPQAKKDFFSSHPLREPVNATEDPSSGYYSTTIRYQATGFGT

NETEYLFEVDNLTYVQLESRFTPQFLLQLNETIYTSGKRSNTTGKLIWKVNPEIDTTI

GEWAFWETKKNLTRKIRSEELSFTAVSNRAKNISGQSPARTSSDPGTNTTTEDHKIM

ASENSSAMVQVHSQGREAAVSHLTTLATISTSPQPPTTKPGPDNSTHNTPVYKLDIS

EATQVEQHHRRTDNDSTASDTPPATTAAGPLKAENTNTSKGTDLLDPATTTSPQNH

SETAGNNNTHHQDTGEESASSGKLGLITNTIAGVAGLITGGRRARREAIVNAQPKC

NPNLHYWTTQDEGAAIGLAWIPYFGPAAEGIYIEGLMHNQDGLICGLRQLANETTQ

ALQLFLRATTELRTFSILNRKAIDFLLQRWGGTCHILGPDCCIEPHDWTKNITDKIDQ

IIHDFVDKTLPDQGDNDNWWTGWRQWIPAGIGVTGVIIAVIALFCICKFVF

SEQ ID NO: 4: Delta mucin Ebola virus (Kikwit strain) glycoprotein:
MGVTGILQLPRDRFKRTSFFLWVIILFQRTFSIPLGVIHNSTLQVSDVDKLVCRDKLS

STNQLRSVGLNLEGNGVATDVPSATKRWGFRSGVPPKVVNYEAGEWAENCYNLEI

KKPDGSECLPAAPDGIRGFPRCRYVHKVSGTGPCAGDFAFHKEGAFFLYDRLASTV

IYRGTTFAEGVVAFLILPQAKKDFFSSHPLREPVNATEDPSSGYYSTTIRYQATGFGT

NETEYLFEVDNLTYVQLESRFTPQFLLQLNETIYTSGKRSNTTGKLIWKVNPEIDTTI

GEWAFWETKKNLTRKIRSEELSFTAVSHHQDTGEESASSGKLGLITNTIAGVAGLIT

GGRRARREAIVNAQPKCNPNLHYWTTQDEGAAIGLAWIPYFGPAAEGIYIEGLMHN

-continued

QDGLICGLRQLANETTQALQLFLRATTELRTFSILNRKAIDFLLQRWGGTCHILGPD

CCIEPHDWTKNITDKIDQIIHDFVDKTLPDQGDNDNWWTGWRQWIPAGIGVTGVII

AVIALFCICKFVF

SEQ ID NO: 5: Ebola virus (Makona strain) glycoprotein (Genbank Acc# KT013256):
MGVTGILQLPRDRFKRTSFFLWVIILFQRTFSIPLGVIHNSTLQVSDVDKLVCRDKLS

STNQLRSVGLNLEGNGVATDVPSATKRWGFRSGVPPKVVNYEAGEWAENCYNLEI

KKPDGSECLPAAPDGIRGFPRCRYVHKVSGTGPCAGDFAFHKEGAFFLYDRLASTV

IYRGTTFAEGVVAFLILPQAKKDFFSSHPLREPVNATEDPSSGYYSTTIRYQATGFGT

NETEYLFEVDNLTYVQLESRFTPQFLLQLNETIYASGKRSNTTGKLIWKVNPEIDTTI

GEWAFWETKKNLTRKIRSEELSFTAVSNGPKNISGQSPARTSSDPETNTTNEDHKIM

ASENSSAMVQVHSQGRKAAVSHLTTLATISTSPQPPTTKTGPDNSTHNTPVYKLDIS

EATQVGQHHRRADNDSTASDTPPATTAAGPLKAENTNTSKSADSLDLATTTSPQNY

SETAGNNNTHHQDTGEESASSGKLGLITNTIAGVAGLITGGRRTRREVIVNAQPKCN

PNLHYWTTQDEGAAIGLAWIPYFGPAAEGIYTEGLMHNQNGLICGLRQLANETTQ

ALQLFLRATTELRTFSILNRKAIDFLLQRWGGTCHILGPDCCIEPHDWTKNITDKIDQ

IIHDFVDKTLPDQGDNDNWWTGWRQWIPAGIGVTGVIIAVIALFCICKFVF

SEQ ID NO: 6: Delta mucin Ebola virus (Makona strain) glycoprotein:
MGVTGILQLPRDRFKRTSFFLWVIILFQRTFSIPLGVIHNSTLQVSDVDKLVCRDKLS

STNQLRSVGLNLEGNGVATDVPSATKRWGFRSGVPPKVVNYEAGEWAENCYNLEI

KKPDGSECLPAAPDGIRGFPRCRYVHKVSGTGPCAGDFAFHKEGAFFLYDRLASTV

IYRGTTFAEGVVAFLILPQAKKDFFSSHPLREPVNATEDPSSGYYSTTIRYQATGFGT

NETEYLFEVDNLTYVQLESRFTPQFLLQLNETIYASGKRSNTTGKLIWKVNPEIDTTI

GEWAFWETKKNLTRKIRSEELSFTAVSHHQDTGEESASSGKLGLITNTIAGVAGLIT

GGRRTRREVIVNAQPKCNPNLHYWTTQDEGAAIGLAWIPYFGPAAEGIYTEGLMH

NQNGLICGLRQLANETTQALQLFLRATTELRTFSILNRKAIDFLLQRWGGTCHILGP

DCCIEPHDWTKNITDKIDQIIHDFVDKTLPDQGDNDNWWTGWRQWIPAGIGVTGVI

IAVIALFCICKFVF

SEQ ID NO: 7: Sudan virus (Boniface strain) glycoprotein (Genkbank# FJ968794):
MEGLSLLQLPRDKFRKSSFFVWVIILFQKAFSMPLGVVTNSTLEVTEIDQLVCKDHL

ASTDQLKSVGLNLEGSGVSTDIPSATKRWGFRSGVPPKVFSYEAGEWAENCYNLEI

KKPDGSECLPPPPDGVRGFPRCRYVHKAQGTGPCPGDYAFHKDGAFFLYDRLAST

VIYRGVNFAEGVIAFLILAKPKETFLQSPPIREAVNYTENTSSYYATSYLEYEIENFG

AQHSTTLFKINNNTFVLLDRPHTPQFLFQLNDTIHLHQQLSNTTGKLIWTLDANINA

DIGEWAFWENKKNLSEQLRGEELSFETLSLNETEDDDATSSRTTKGRISDRATRKYS

DLVPKDSPGMVSLHVPEGETTLPSQNSTEGRRVDVNTQETITETTATIIGTNGNNMQ

ISTIGTGLSSSQILSSSPTMAPSPETQTSTTYTPKLPVMTTEESTTPPRNSPGSTTEAPT

LTTPENITTAVKTVLPQESTSNGLITSTVTGILGSLGLRKRSRRQVNTRATGKCNPNL

HYWTAQEQHNAAGIAWIPYFGPGAEGIYTEGLMHNQNALVCGLRQLANETTQAL

QLFLRATTELRTYTILNRKAIDFLLRRWGGTCRILGPDCCIEPHDWTKNITDKINQIIH

DFIDNPLPNQDNDDNWWTGWRQWIPAGIGITGIIIAIIALLCVCKLLC

SEQ ID NO: 8: Delta mucin Sudan virus (Boniface strain) glycoprotein:
MEGLSLLQLPRDKFRKSSFFVWVIILFQKAFSMPLGVVTNSTLEVTEIDQLVCKDHL

ASTDQLKSVGLNLEGSGVSTDIPSATKRWGFRSGVPPKVFSYEAGEWAENCYNLEI

KKPDGSECLPPPPDGVRGFPRCRYVHKAQGTGPCPGDYAFHKDGAFFLYDRLAST

VIYRGVNFAEGVIAFLILAKPKETFLQSPPIREAVNYTENTSSYYATSYLEYEIENFG

AQHSTTLFKINNNTFVLLDRPHTPQFLFQLNDTIHLHQQLSNTTGKLIWTLDANINA

DIGEWAFWENKKNLSEQLRGEELSFETLSTTAVKTVLPQESTSNGLITSTVTGILGSL

GLRKRSRRQVNTRATGKCNPNLHYWTAQEQHNAAGIAWIPYFGPGAEGIYTEGLM

HNQNALVCGLRQLANETTQALQLFLRATTELRTYTILNRKAIDFLLRRWGGTCRIL

GPDCCIEPHDWTKNITDKINQIIHDFIDNPLPNQDNDDNWWTGWRQWIPAGIGITGII

IAIIALLCVCKLLC

SEQ ID NO: 9: Sudan virus (Gulu strain) glycoprotein (Genbank# AY729654):
MGGLSLLQLPRDKFRKSSFFVWVIILFQKAFSMPLGVVTNSTLEVTEIDQLVCKDHL

ASTDQLKSVGLNLEGSGVSTDIPSATKRWGFRSGVPPKVVSYEAGEWAENCYNLEI

KKPDGSECLPPPPDGVRGFPRCRYVHKAQGTGPCPGDYAFHKDGAFFLYDRLAST

VIYRGVNFAEGVIAFLILAKPKETFLQSPPIREAVNYTENTSSYYATSYLEYEIENFG

AQHSTTLFKIDNNTFVRLDRPHTPQFLFQLNDTIHLHQQLSNTTGRLIWTLDANINA

DIGEWAFWENKKNLSEQLRGEELSFEALSLNETEDDDAASSRITKGRISDRATRKYS

DLVPKNSPGMVPLHIPEGETTLPSQNSTEGRRVGVNTQETITETAATIIGTNGNHMQI

STIGIRPSSSQIPSSSPTTAPSPEAQTPTTHTSGPSVMATEEPTTPPGSSPGPTTEAPTLT

TPENITTAVKTVLPQESTSNGLITSTVTGILGSLGLRKRSRRQTNTKATGKCNPNLHY

WTAQEQHNAAGIAWIPYFGPGAEGIYTEGLMHNQNALVCGLRQLANETTQALQLF

LRATTELRTYTILNRKAIDFLLRRWGGTCRILGPDCCIEPHDWTKNITDKINQIIHDFI

DNPLPNQDNDDNWWTGWRQWIPAGIGITGIIIAIIALLCVCKLLC

SEQ ID NO: 10: Delta mucin Sudan virus (Gulu strain) glycoprotein:
MGGLSLLQLPRDKFRKSSFFVWVIILFQKAFSMPLGVVTNSTLEVTEIDQLVCKDHL

ASTDQLKSVGLNLEGSGVSTDIPSATKRWGFRSGVPPKVVSYEAGEWAENCYNLEI

KKPDGSECLPPPPDGVRGFPRCRYVHKAQGTGPCPGDYAFHKDGAFFLYDRLAST

VIYRGVNFAEGVIAFLILAKPKETFLQSPPIREAVNYTENTSSYYATSYLEYEIENFG

AQHSTTLFKIDNNTFVRLDRPHTPQFLFQLNDTIHLHQQLSNTTGRLIWTLDANINA

DIGEWAFWENKKNLSEQLRGEELSFEALSTTAVKTVLPQESTSNGLITSTVTGILGSL

GLRKRSRRQTNTKATGKCNPNLHYWTAQEQHNAAGIAWIPYFGPGAEGIYTEGLM

HNQNALVCGLRQLANETTQALQLFLRATTELRTYTILNRKAIDFLLRRWGGTCRIL

GPDCCIEPHDWTKNITDKINQIIHDFIDNPLPNQDNDDNWWTGWRQWIPAGIGITGII

IAIIALLCVCKLLC

SEQ ID NO: 11: Bundibugyo virus (tc/UGA/2007/Bundibugyo-200706291) glycoprotein
(Genbank# KU182911):
MVTSGILQLPRERFRKTSFFVWVIILFHKVFPIPLGVVHNNTLQVSDIDKLVCRDKLS

STSQLKSVGLNLEGNGVATDVPTATKRWGFRAGVPPKVVNYEAGEWAENCYNLD

IKKADGSECLPEAPEGVRGFPRCRYVHKVSGTGPCPEGYAFHKEGAFFLYDRLASTI

IYRSTTFSEGVVAFLILPETKKDFFQSPPLHEPANMTTDPSSYYHTVTLNYVADNFG

TNMTNLFQVDHLTYVQLEPRFTPQFLVQLNETIYTNGRRSNTTGTLIWKVNPTVD

TGVGEWAFWENKKNFTKTLSSEELSVIFVPRAQDPGSNQKTKVTPTSFANNQTSKN

HEDLVPEDPASVVQVRDLQRENTVPTPPPDTVPTTLIPDTMEEQTTSHYEPPNISRN

HQERNNTAHPETLANNPPDNTTPSTPPQDGERTSSHTTPSPRPVPTSTIHPTTRETHIP

TTMTTSHDTDSNRPNPIDISESTEPGPLTNTTRGAANLLTGSRRTRREITLRTQAKCN

PNLHYWTTQDEGAAIGLAWIPYFGPAAEGIYTEGIMHNQNGLICGLRQLANETTQA

LQLFLRATTELRTFSILNRKAIDFLLQRWGGTCHILGPDCCIEPHDWTKNITDKIDQII

HDFIDKPLPDQTDNDNWWTGWRQWVPAGIGITGVIIAVIALLCICKFLL

SEQ ID NO: 12: Delta mucin Bundibugyo virus (tc/UGA/2007/Bundibugyo-200706291) glycoprotein:
MVTSGILQLPRERFRKTSFFVWVIILFHKVFPIPLGVVHNNTLQVSDIDKLVCRDKLS

STSQLKSVGLNLEGNGVATDVPTATKRWGFRAGVPPKVVNYEAGEWAENCYNLD

IKKADGSECLPEAPEGVRGFPRCRYVHKVSGTGPCPEGYAFHKEGAFFLYDRLASTI

IYRSTTFSEGVVAFLILPETKKDFFQSPPLHEPANMTTDPSSYYHTVTLNYVADNFG

TNMTNFLFQVDHLTYVQLEPRFTPQFLVQLNETIYTNGRRSNTTGTLIWKVNPTVD

TGVGEAFWENKKNFTKTLSSEELSVIFVPSNRPNPIDISESTEPGPLTNTTRGAANL

LTGSRRTRREITLRTQAKCNPNLHYWTTQDEGAAIGLAWIPYFGPAAEGIYTEGIMH

NQNGLICGLRQLANETTQALQLFLRATTELRTFSILNRKAIDFLLQRWGGTCHILGP

DCCIEPHDWTKNITDKIDQIIHDFIDKPLPDQTDNDNWWTGWRQWVPAGIGITGVII

AVIALLCICKFLL

SEQ ID NO: 13: Reston virus (Pennsylvania strain) glycoprotein (Genbank# AF522874):
MGSGYQLLQLPRERFRKTSFLVWVIILFQRAISMPLGIVTNSTLKATEIDQLVCRDKL

SSTSQLKSVGLNLEGNGIATDVPSATKRWGFRSGVPPKVVSYEAGEWAENCYNLEI

KKSDGSECLPLPPDGVRGFPRCRYVHKVQGTGPCPGDLAFHKNGAFFLYDRLASTV

IYRGTTFAEGVVAFLILSEPKKHFWKATPAHEPVNTTDDSTSYYMTLTLSYEMSNF

GGNESNTLFKVDNHTYVQLDRPHTPQFLVQLNETLRRNNRLSNTGRLTWTLDPKI

EPDVGEWAFWETKKNFSQQLHGENLHFQIPSTHTNNSSDQSPAGTVQGKISYHPPA

NNSELVPTDSPPVVSVLTAGRTEEMSTQGLTNGETITGFTANPMTTTIAPSPTMTSE

VDNNVPSEQPNNTASIEDSPPSASNETIYHSEMDPIQGSNNSAQSPQTKTTPAPTTSP

MTQDPQETANSSKPGTSPGSAAGPSQPGLTINTVSKVADSLSPTRKQKRSVRQNTA

NKCNPDLYYWTAVDEGAAVGLAWIPYFGPAAEGIYIEGVMHNQNGLICGLRQLAN

ETTQALQLFLRATTELRTYSLLNRKAIDFLLQRWGGTCRILGPSCCIEPHDWTKNIT

DEINQIKHDFIDNPLPDHGDDLNLWTGWRQWIPAGIGIIGVIIAIIALLCICKILC

SEQ ID NO: 14: Delta mucin Reston virus (Pennsylvania strain) glycoprotein:
MGSGYQLLQLPRERFRKTSFLVWVIILFQRAISMPLGIVTNSTLKATEIDQLVCRDKL

SSTSQLKSVGLNLEGNGIATDVPSATKRWGFRSGVPPKVVSYEAGEWAENCYNLEI

KKSDGSECLPLPPDGVRGFPRCRYVHKVQGTGPCPGDLAFHKNGAFFLYDRLASTV

IYRGTTFAEGVVAFLILSEPKKHFWKATPAHEPVNTTDDSTSYYMTLTLSYEMSNF

GGNESNTLFKVDNHTYVQLDRPHTPQFLVQLNETLRRNNRLSNTGRLTWTLDPKI

EPDVGEWAFWETKKNFSQQLHGENLHFQIPSKPGTSPGSAAGPSQPGLTINTVSKV

ADSLSPTRKQKRSVRQNTANKCNPDLYYWTAVDEGAAVGLAWIPYFGPAAEGIYI

EGVMHNQNGLICGLRQLANETTQALQLFLRATTELRTYSLLNRKAIDFLLQRWGGT

CRILGPSCCIEPHDWTKNITDEINQIKHDFIDNPLPDHGDDLNLWTGWRQWIPAGIGI

IGVIIAIIALLCICKILC

SEQ ID NO: 15: Tai Forrest virus (tc/CIV/1994/Pauleoula-CI strain) glyocprotein
(Genbank# NC_014372):
MGASGILQLPRERFRKTSFFVWVIILFHKVFSIPLGVVHNNTLQVSDIDKFVCRDKLS

STSQLKSVGLNLEGNGVATDVPTATKRWGFRAGVPPKVVNCEAGEWAENCYNLA

-continued

IKKVDGSECLPEAPEGVRDFPRCRYVHKVSGTGPCPGGLAFHKEGAFFLYDRLASTI

IYRGTTFAEGVIAFLILPKARKDFFQSPPLHEPANMTTDPSSYYHTTTINYVVDNFGT

NTTEFLFQVDHLTYVQLEARFTPQFLVLLNETIYSDNRRSNTTGKLIWKINPTVDTS

MGEWAFWENKKNFTKTLSSEELSFVPVPETQNQVLDTTATVSPPISAHNHAAEDHK

ELVSEDSTPVVQMQNIKGKDTMPTTVTGVPTTTPSPFPINARNTDHTKSFIGLEGPQ

EDHSTTQPAKTTSQPTNSTESTTLNPTSEPSSRGTGPSSPTVPNTTESHAELGKTTPTT

LPEQHTAASAIPRAVHPDELSGPGFLTNTIRGVTNLLTGSRRKRRDVTPNTQPKCNP

NLHYWTALDEGAAIGLAWIPYFGPAAEGIYTEGIMENQNGLICGLRQLANETTQAL

QLFLRATTELRTFSILNRKAIDFLLQRWGGTCHILGPDCCIEPQDWTKNITDKIDQIIH

DFVDNNLPNQNDGSNWWTGWKQWVPAGIGITGVIIAIIALLCICKFML

SEQ ID NO: 16: Delta mucin Tai Forrest virus (tc/CIV/1994/Pauleoula-CI strain) glycoprotein:
MGASGILQLPRERFRKTSFFVWVIILFHKVFSIPLGVVHNNTLQVSDIDKFVCRDKLS

STSQLKSVGLNLEGNGVATDVPTATKRWGFRAGVPPKVVNCEAGEWAENCYNLA

IKKVDGSECLPEAPEGVRDFPRCRYVHKVSGTGPCPGGLAFHKEGAFFLYDRLASTI

IYRGTTFAEGVIAFLILPKARKDFFQSPPLHEPANMTTDPSSYYHTTTINYVVDNFGT

NTTEFLFQVDHLTYVQLEARFTPQFLVLLNETIYSDNRRSNTTGKLIWKINPTVDTS

MGEWAFWENKKNFTKTLSSEELSFVPVPSAIPRAVHPDELSGPGFLTNTIRGVTNLL

TGSRRKRRDVTPNTQPKCNPNLHYWTALDEGAAIGLAWIPYFGPAAEGIYTEGIME

NQNGLICGLRQLANETTQALQLFLRATTELRTFSILNRKAIDFLLQRWGGTCHILGP

DCCIEPQDWTKNITDKIDQIIHDFVDNNLPNQNDGSNWWTGWKQWVPAGIGITGVI

IAIIALLCICKFML

---

What is claimed is:

1. An immunogen comprising a modified filovirus spike glycoprotein (GP) or immunogenic fragment thereof, wherein the filovirus is Ebola virus (EBOV), wherein the filovirus GP comprises the GP head domain and the GP base domain, wherein the base domain comprises one or more single amino acid substitutions relative to the corresponding wild-type EBOV GP amino acid sequence, and wherein the one or more amino acid substitutions can affect the conformation of a cross-reactive epitope in the head domain, thereby increasing immunogenicity of the immunogen against the corresponding wild-type filovirus GP, and/or broadening the cross-reactive immunogenicity of the immunogen against other filovirus species or strains; and wherein the amino acid substitution in the GP base domain comprises a C53A, F183A, N512A, A562S, L569A, L573A, F159A, P513A, L515A, T565A, R164A, L184A, I185A, H516A, G546A, L51A, G179A, Q508A, C511A, Y517A, R559A, C601A, I33A, P34A, I38A, V48A, V52A, L68A, E103A, A182S, R498A, R501A, N514A, W531A, P533A, E545A, C556A, L561A, S583A, I610A, L43A, V45A, R54A, L57A, L63A, V66A, E71A, Y99A, L161A, L165A, P187A, N506A, P509A, K510A, W518A, A525S, L558A, Q560A, E564A, T566A, Q570A, I603A, L604A, G605A, C608A, C609A, D614A, T616A, I623A, or W648A substitution corresponding to the wild-type EBOV strain Mayinga-76 GP.

2. An immunogen comprising a modified filovirus spike glycoprotein (GP) or immunogenic fragment thereof, wherein the filovirus is Ebola virus (EBOV), wherein the filovirus GP comprises the GP head domain and the GP base domain, wherein the base domain comprises one or more single amino acid substitutions relative to the corresponding wild-type EBOV GP amino acid sequence, and wherein the one or more amino acid substitutions can affect the conformation of a cross-reactive epitope in the head domain, thereby increasing immunogenicity of the immunogen against the corresponding wild-type filovirus GP, and/or broadening the cross-reactive immunogenicity of the immunogen against other filovirus species or strains;

wherein the amino acid substitution in the GP base domain comprises an amino acid substitution at a position corresponding to I185 of the wild-type EBOV strain Mayinga-76 GP and wherein the amino acid substitution in the GP base domain is from the wild-type residue to a glycine (G), alanine (A), valine (V), leucine (L), isoleucine (I), proline (P), phenylalanine (F), methionine (M), or tryptophan (W) residue.

3. The immunogen of claim 2, wherein the amino acid substitution in the GP base domain comprises an amino acid substitution at a position corresponding to I185 of the wild-type EBOV strain Mayinga-76 GP and wherein the amino acid substitution in the GP base domain is from the wild-type residue to a glycine (G), alanine (A), or serine (S) residue.

4. The immunogen of claim 2, wherein the amino acid substitution in the GP base domain comprises an amino acid substitution at a position corresponding to I185 of the wild-type EBOV strain Mayinga-76 GP and wherein the amino acid substitution in the GP base domain is from the wild-type residue to a glycine (G) or alanine (A) residue.

5. The immunogen of claim 2, wherein the amino acid substitution in the GP base domain comprises an I185A substitution corresponding to the wild-type EBOV strain Mayinga-76 GP.

6. An immunogen comprising a modified filovirus spike glycoprotein (GP) or immunogenic fragment thereof, wherein the filovirus is Ebola virus (EBOV), wherein the filovirus GP comprises the GP head domain and the GP base domain, wherein the base domain comprises one or more single amino acid substitutions relative to the corresponding wild-type EBOV GP amino acid sequence, and wherein the one or more amino acid substitutions can affect the conformation of a cross-reactive epitope in the head domain, thereby increasing immunogenicity of the immunogen against the corresponding wild-type filovirus GP, and/or broadening the cross-reactive immunogenicity of the immunogen against other filovirus species or strains;

wherein the amino acid substitution in the GP base domain comprises an amino acid substitution at a position corresponding to W531 of the wild-type EBOV strain Mayinga-76 GP and wherein the amino acid substitution in the GP base domain is from the wild-type residue to a glycine (G), alanine (A), valine (V), leucine (L), isoleucine (I), proline (P), phenylalanine (F), methionine (M), or tryptophan (W) residue.

7. The immunogen of claim 6, wherein the amino acid substitution in the GP base domain comprises an amino acid substitution at a position corresponding to W531 of the wild-type EBOV strain Mayinga-76 GP and wherein the amino acid substitution in the GP base domain is from the wild-type residue to a glycine (G), alanine (A), or serine (S) residue.

8. The immunogen of claim 6, wherein the amino acid substitution in the GP base domain comprises an amino acid substitution at a position corresponding to W531 of the wild-type EBOV strain Mayinga-76 GP and wherein the amino acid substitution in the GP base domain is from the wild-type residue to a glycine (G) or alanine (A) residue.

9. The immunogen of claim 6, wherein the amino acid substitution in the GP base domain comprises an W531A substitution corresponding to the wild-type EBOV strain Mayinga-76 GP.

10. An immunogen comprising a modified filovirus spike glycoprotein (GP) or immunogenic fragment thereof, wherein the filovirus is Ebola virus (EBOV), wherein the filovirus GP comprises the GP head domain and the GP base domain, wherein the base domain comprises one or more single amino acid substitutions relative to the corresponding wild-type EBOV GP amino acid sequence, and wherein the one or more amino acid substitutions can affect the conformation of a cross-reactive epitope in the head domain, thereby increasing immunogenicity of the immunogen against the corresponding wild-type filovirus GP, and/or broadening the cross-reactive immunogenicity of the immunogen against other filovirus species or strains;
wherein the amino acid substitution in the GP base domain comprises an amino acid substitution at a position corresponding to L573 of the wild-type EBOV strain Mayinga-76 GP and wherein said amino acid substitution in the GP base domain is from the wild-type residue to a glycine (G), alanine (A), valine (V), leucine (L), isoleucine (I), proline (P), phenylalanine (F), methionine (M), or tryptophan (W) residue.

11. The immunogen of claim 10, wherein the amino acid substitution in the GP base domain comprises an amino acid substitution at a position corresponding to L573 of the wild-type EBOV strain Mayinga-76 GP and wherein the amino acid substitution in the GP base domain is from the wild-type residue to a glycine (G), alanine (A), or serine (S) residue.

12. The immunogen of claim 10, wherein the amino acid substitution in the GP base domain comprises an amino acid substitution at a position corresponding to L573 of the wild-type EBOV strain Mayinga-76 GP and wherein the amino acid substitution in the GP base domain is from the wild-type residue to a glycine (G) or alanine (A) residue.

13. The immunogen of claim 10, wherein the amino acid substitution in the GP base domain comprises a L573A substitution corresponding to the wild-type EBOV strain Mayinga-76 GP.

* * * * *

SEQUENCE LISTING

<160> NUMBER OF SEQ ID NOS: 22

<210> SEQ ID NO 1
<211> LENGTH: 676
<212> TYPE: PRT
<213> ORGANISM: Ebola virus (Mayinga strain)

<400> SEQUENCE: 1

Met Gly Val Thr Gly Ile Leu Gln Leu Pro Arg Asp Arg Phe Lys Arg
1               5                   10                  15

Thr Ser Phe Phe Leu Trp Val Ile Ile Leu Phe Gln Arg Thr Phe Ser
            20                  25                  30

Ile Pro Leu Gly Val Ile His Asn Ser Thr Leu Gln Val Ser Asp Val
        35                  40                  45

Asp Lys Leu Val Cys Arg Asp Lys Leu Ser Ser Thr Asn Gln Leu Arg
    50                  55                  60

Ser Val Gly Leu Asn Leu Glu Gly Asn Gly Val Ala Thr Asp Val Pro
65                  70                  75                  80

Ser Ala Thr Lys Arg Trp Gly Phe Arg Ser Gly Val Pro Pro Lys Val
                85                  90                  95

Val Asn Tyr Glu Ala Gly Glu Trp Ala Glu Asn Cys Tyr Asn Leu Glu
            100                 105                 110

Ile Lys Lys Pro Asp Gly Ser Glu Cys Leu Pro Ala Ala Pro Asp Gly
        115                 120                 125

```
Ile Arg Gly Phe Pro Arg Cys Arg Tyr Val His Lys Val Ser Gly Thr
130                 135                 140
Gly Pro Cys Ala Gly Asp Phe Ala Phe His Lys Glu Gly Ala Phe Phe
145                 150                 155                 160
Leu Tyr Asp Arg Leu Ala Ser Thr Val Ile Tyr Arg Gly Thr Thr Phe
                165                 170                 175
Ala Glu Gly Val Val Ala Phe Leu Ile Leu Pro Gln Ala Lys Lys Asp
            180                 185                 190
Phe Phe Ser Ser His Pro Leu Arg Glu Pro Val Asn Ala Thr Glu Asp
        195                 200                 205
Pro Ser Ser Gly Tyr Tyr Ser Thr Thr Ile Arg Tyr Gln Ala Thr Gly
210                 215                 220
Phe Gly Thr Asn Glu Thr Glu Tyr Leu Phe Glu Val Asp Asn Leu Thr
225                 230                 235                 240
Tyr Val Gln Leu Glu Ser Arg Phe Thr Pro Gln Phe Leu Leu Gln Leu
                245                 250                 255
Asn Glu Thr Ile Tyr Thr Ser Gly Lys Arg Ser Asn Thr Thr Gly Lys
            260                 265                 270
Leu Ile Trp Lys Val Asn Pro Glu Ile Asp Thr Thr Ile Gly Glu Trp
        275                 280                 285
Ala Phe Trp Glu Thr Lys Lys Asn Leu Thr Arg Lys Ile Arg Ser Glu
290                 295                 300
Glu Leu Ser Phe Thr Val Val Ser Asn Gly Ala Lys Asn Ile Ser Gly
305                 310                 315                 320
Gln Ser Pro Ala Arg Thr Ser Ser Asp Pro Gly Thr Asn Thr Thr Thr
                325                 330                 335
Glu Asp His Lys Ile Met Ala Ser Glu Asn Ser Ser Ala Met Val Gln
            340                 345                 350
Val His Ser Gln Gly Arg Glu Ala Ala Val Ser His Leu Thr Thr Leu
        355                 360                 365
Ala Thr Ile Ser Thr Ser Pro Gln Ser Leu Thr Thr Lys Pro Gly Pro
370                 375                 380
Asp Asn Ser Thr His Asn Thr Pro Val Tyr Lys Leu Asp Ile Ser Glu
385                 390                 395                 400
Ala Thr Gln Val Glu Gln His His Arg Arg Thr Asp Asn Asp Ser Thr
                405                 410                 415
Ala Ser Asp Thr Pro Ser Ala Thr Thr Ala Ala Gly Pro Pro Lys Ala
            420                 425                 430
Glu Asn Thr Asn Thr Ser Lys Ser Thr Asp Phe Leu Asp Pro Ala Thr
        435                 440                 445
Thr Thr Ser Pro Gln Asn His Ser Glu Thr Ala Gly Asn Asn Asn Thr
450                 455                 460
His His Gln Asp Thr Gly Glu Glu Ser Ala Ser Ser Gly Lys Leu Gly
465                 470                 475                 480
Leu Ile Thr Asn Thr Ile Ala Gly Val Ala Gly Leu Ile Thr Gly Gly
                485                 490                 495
Arg Arg Thr Arg Arg Glu Ala Ile Val Asn Ala Gln Pro Lys Cys Asn
            500                 505                 510
Pro Asn Leu His Tyr Trp Thr Thr Gln Asp Glu Gly Ala Ala Ile Gly
        515                 520                 525
Leu Ala Trp Ile Pro Tyr Phe Gly Pro Ala Ala Glu Gly Ile Tyr Ile
530                 535                 540
```

Glu Gly Leu Met His Asn Gln Asp Gly Leu Ile Cys Gly Leu Arg Gln
545                 550                 555                 560

Leu Ala Asn Glu Thr Thr Gln Ala Leu Gln Leu Phe Leu Arg Ala Thr
                565                 570                 575

Thr Glu Leu Arg Thr Phe Ser Ile Leu Asn Arg Lys Ala Ile Asp Phe
            580                 585                 590

Leu Leu Gln Arg Trp Gly Gly Thr Cys His Ile Leu Gly Pro Asp Cys
        595                 600                 605

Cys Ile Glu Pro His Asp Trp Thr Lys Asn Ile Thr Asp Lys Ile Asp
    610                 615                 620

Gln Ile Ile His Asp Phe Val Asp Lys Thr Leu Pro Asp Gln Gly Asp
625                 630                 635                 640

Asn Asp Asn Trp Trp Thr Gly Trp Arg Gln Trp Ile Pro Ala Gly Ile
                645                 650                 655

Gly Val Thr Gly Val Ile Ile Ala Val Ile Ala Leu Phe Cys Ile Cys
            660                 665                 670

Lys Phe Val Phe
        675

<210> SEQ ID NO 2
<211> LENGTH: 524
<212> TYPE: PRT
<213> ORGANISM: Ebola virus (Mayinga strain)

<400> SEQUENCE: 2

Met Gly Val Thr Gly Ile Leu Gln Leu Pro Arg Asp Arg Phe Lys Arg
1               5                   10                  15

Thr Ser Phe Phe Leu Trp Val Ile Ile Leu Phe Gln Arg Thr Phe Ser
                20                  25                  30

Ile Pro Leu Gly Val Ile His Asn Ser Thr Leu Gln Val Ser Asp Val
            35                  40                  45

Asp Lys Leu Val Cys Arg Asp Lys Leu Ser Ser Thr Asn Gln Leu Arg
        50                  55                  60

Ser Val Gly Leu Asn Leu Glu Gly Asn Gly Val Ala Thr Asp Val Pro
65                  70                  75                  80

Ser Ala Thr Lys Arg Trp Gly Phe Arg Ser Gly Val Pro Pro Lys Val
                85                  90                  95

Val Asn Tyr Glu Ala Gly Glu Trp Ala Glu Asn Cys Tyr Asn Leu Glu
            100                 105                 110

Ile Lys Lys Pro Asp Gly Ser Glu Cys Leu Pro Ala Ala Pro Asp Gly
        115                 120                 125

Ile Arg Gly Phe Pro Arg Cys Arg Tyr Val His Lys Val Ser Gly Thr
    130                 135                 140

Gly Pro Cys Ala Gly Asp Phe Ala Phe His Lys Glu Gly Ala Phe Phe
145                 150                 155                 160

Leu Tyr Asp Arg Leu Ala Ser Thr Val Ile Tyr Arg Gly Thr Thr Phe
                165                 170                 175

Ala Glu Gly Val Val Ala Phe Leu Ile Leu Pro Gln Ala Lys Lys Asp
            180                 185                 190

Phe Phe Ser Ser His Pro Leu Arg Glu Pro Val Asn Ala Thr Glu Asp
        195                 200                 205

Pro Ser Ser Gly Tyr Tyr Ser Thr Thr Ile Arg Tyr Gln Ala Thr Gly
    210                 215                 220

Phe Gly Thr Asn Glu Thr Glu Tyr Leu Phe Glu Val Asp Asn Leu Thr
225                 230                 235                 240

```
Tyr Val Gln Leu Glu Ser Arg Phe Thr Pro Gln Phe Leu Gln Leu
                245                 250                 255

Asn Glu Thr Ile Tyr Thr Ser Gly Lys Arg Ser Asn Thr Thr Gly Lys
            260                 265                 270

Leu Ile Trp Lys Val Asn Pro Glu Ile Asp Thr Thr Ile Gly Glu Trp
        275                 280                 285

Ala Phe Trp Glu Thr Lys Lys Asn Leu Thr Arg Lys Ile Arg Ser Glu
    290                 295                 300

Glu Leu Ser Phe Thr Val Val Ser His His Gln Asp Thr Gly Glu Glu
305                 310                 315                 320

Ser Ala Ser Ser Gly Lys Leu Gly Leu Ile Thr Asn Thr Ile Ala Gly
                325                 330                 335

Val Ala Gly Leu Ile Thr Gly Gly Arg Arg Thr Arg Arg Glu Ala Ile
            340                 345                 350

Val Asn Ala Gln Pro Lys Cys Asn Pro Asn Leu His Tyr Trp Thr Thr
        355                 360                 365

Gln Asp Glu Gly Ala Ala Ile Gly Leu Ala Trp Ile Pro Tyr Phe Gly
    370                 375                 380

Pro Ala Ala Glu Gly Ile Tyr Ile Glu Gly Leu Met His Asn Gln Asp
385                 390                 395                 400

Gly Leu Ile Cys Gly Leu Arg Gln Leu Ala Asn Glu Thr Thr Gln Ala
                405                 410                 415

Leu Gln Leu Phe Leu Arg Ala Thr Thr Glu Leu Arg Thr Phe Ser Ile
            420                 425                 430

Leu Asn Arg Lys Ala Ile Asp Phe Leu Leu Gln Arg Trp Gly Gly Thr
        435                 440                 445

Cys His Ile Leu Gly Pro Asp Cys Cys Ile Glu Pro His Asp Trp Thr
    450                 455                 460

Lys Asn Ile Thr Asp Lys Ile Asp Gln Ile Ile His Asp Phe Val Asp
465                 470                 475                 480

Lys Thr Leu Pro Asp Gln Gly Asp Asn Asp Asn Trp Trp Thr Gly Trp
                485                 490                 495

Arg Gln Trp Ile Pro Ala Gly Ile Gly Val Thr Gly Val Ile Ile Ala
            500                 505                 510

Val Ile Ala Leu Phe Cys Ile Cys Lys Phe Val Phe
        515                 520

<210> SEQ ID NO 3
<211> LENGTH: 676
<212> TYPE: PRT
<213> ORGANISM: Ebola virus (Kikwit strain)

<400> SEQUENCE: 3

Met Gly Val Thr Gly Ile Leu Gln Leu Pro Arg Asp Arg Phe Lys Arg
1               5                   10                  15

Thr Ser Phe Phe Leu Trp Val Ile Ile Leu Phe Gln Arg Thr Phe Ser
            20                  25                  30

Ile Pro Leu Gly Val Ile His Asn Ser Thr Leu Gln Val Ser Asp Val
        35                  40                  45

Asp Lys Leu Val Cys Arg Asp Lys Leu Ser Ser Thr Asn Gln Leu Arg
    50                  55                  60

Ser Val Gly Leu Asn Leu Glu Gly Asn Gly Val Ala Thr Asp Val Pro
65                  70                  75                  80

Ser Ala Thr Lys Arg Trp Gly Phe Arg Ser Gly Val Pro Pro Lys Val
```

```
                    85                  90                  95
Val Asn Tyr Glu Ala Gly Glu Trp Ala Glu Asn Cys Tyr Asn Leu Glu
                100                 105                 110
Ile Lys Lys Pro Asp Gly Ser Glu Cys Leu Pro Ala Ala Pro Asp Gly
                115                 120                 125
Ile Arg Gly Phe Pro Arg Cys Arg Tyr Val His Lys Val Ser Gly Thr
                130                 135                 140
Gly Pro Cys Ala Gly Asp Phe Ala Phe His Lys Glu Gly Ala Phe Phe
145                 150                 155                 160
Leu Tyr Asp Arg Leu Ala Ser Thr Val Ile Tyr Arg Gly Thr Thr Phe
                165                 170                 175
Ala Glu Gly Val Val Ala Phe Leu Ile Leu Pro Gln Ala Lys Lys Asp
                180                 185                 190
Phe Phe Ser Ser His Pro Leu Arg Glu Pro Val Asn Ala Thr Glu Asp
                195                 200                 205
Pro Ser Ser Gly Tyr Tyr Ser Thr Thr Ile Arg Tyr Gln Ala Thr Gly
                210                 215                 220
Phe Gly Thr Asn Glu Thr Glu Tyr Leu Phe Glu Val Asp Asn Leu Thr
225                 230                 235                 240
Tyr Val Gln Leu Glu Ser Arg Phe Thr Pro Gln Phe Leu Leu Gln Leu
                245                 250                 255
Asn Glu Thr Ile Tyr Thr Ser Gly Lys Arg Ser Asn Thr Thr Gly Lys
                260                 265                 270
Leu Ile Trp Lys Val Asn Pro Glu Ile Asp Thr Thr Ile Gly Glu Trp
                275                 280                 285
Ala Phe Trp Glu Thr Lys Lys Asn Leu Thr Arg Lys Ile Arg Ser Glu
                290                 295                 300
Glu Leu Ser Phe Thr Ala Val Ser Asn Arg Ala Lys Asn Ile Ser Gly
305                 310                 315                 320
Gln Ser Pro Ala Arg Thr Ser Ser Asp Pro Gly Thr Asn Thr Thr Thr
                325                 330                 335
Glu Asp His Lys Ile Met Ala Ser Glu Asn Ser Ser Ala Met Val Gln
                340                 345                 350
Val His Ser Gln Gly Arg Glu Ala Ala Val Ser His Leu Thr Thr Leu
                355                 360                 365
Ala Thr Ile Ser Thr Ser Pro Gln Pro Pro Thr Thr Lys Pro Gly Pro
                370                 375                 380
Asp Asn Ser Thr His Asn Thr Pro Val Tyr Lys Leu Asp Ile Ser Glu
385                 390                 395                 400
Ala Thr Gln Val Glu Gln His His Arg Arg Thr Asp Asn Asp Ser Thr
                405                 410                 415
Ala Ser Asp Thr Pro Pro Ala Thr Thr Ala Ala Gly Pro Leu Lys Ala
                420                 425                 430
Glu Asn Thr Asn Thr Ser Lys Gly Thr Asp Leu Leu Asp Pro Ala Thr
                435                 440                 445
Thr Thr Ser Pro Gln Asn His Ser Glu Thr Ala Gly Asn Asn Asn Thr
                450                 455                 460
His His Gln Asp Thr Gly Glu Glu Ser Ala Ser Ser Gly Lys Leu Gly
465                 470                 475                 480
Leu Ile Thr Asn Thr Ile Ala Gly Val Ala Gly Leu Ile Thr Gly Gly
                485                 490                 495
Arg Arg Ala Arg Arg Glu Ala Ile Val Asn Ala Gln Pro Lys Cys Asn
                500                 505                 510
```

-continued

```
Pro Asn Leu His Tyr Trp Thr Thr Gln Asp Glu Gly Ala Ala Ile Gly
        515                 520                 525

Leu Ala Trp Ile Pro Tyr Phe Gly Pro Ala Ala Glu Gly Ile Tyr Ile
    530                 535                 540

Glu Gly Leu Met His Asn Gln Asp Gly Leu Ile Cys Gly Leu Arg Gln
545                 550                 555                 560

Leu Ala Asn Glu Thr Thr Gln Ala Leu Gln Leu Phe Leu Arg Ala Thr
                565                 570                 575

Thr Glu Leu Arg Thr Phe Ser Ile Leu Asn Arg Lys Ala Ile Asp Phe
            580                 585                 590

Leu Leu Gln Arg Trp Gly Gly Thr Cys His Ile Leu Gly Pro Asp Cys
        595                 600                 605

Cys Ile Glu Pro His Asp Trp Thr Lys Asn Ile Thr Asp Lys Ile Asp
    610                 615                 620

Gln Ile Ile His Asp Phe Val Asp Lys Thr Leu Pro Asp Gln Gly Asp
625                 630                 635                 640

Asn Asp Asn Trp Trp Thr Gly Trp Arg Gln Trp Ile Pro Ala Gly Ile
                645                 650                 655

Gly Val Thr Gly Val Ile Ile Ala Val Ile Ala Leu Phe Cys Ile Cys
            660                 665                 670

Lys Phe Val Phe
        675

<210> SEQ ID NO 4
<211> LENGTH: 524
<212> TYPE: PRT
<213> ORGANISM: Ebola virus (Kikwit strain)

<400> SEQUENCE: 4

Met Gly Val Thr Gly Ile Leu Gln Leu Pro Arg Asp Arg Phe Lys Arg
1               5                   10                  15

Thr Ser Phe Phe Leu Trp Val Ile Ile Leu Phe Gln Arg Thr Phe Ser
            20                  25                  30

Ile Pro Leu Gly Val Ile His Asn Ser Thr Leu Gln Val Ser Asp Val
        35                  40                  45

Asp Lys Leu Val Cys Arg Asp Lys Leu Ser Ser Thr Asn Gln Leu Arg
    50                  55                  60

Ser Val Gly Leu Asn Leu Glu Gly Asn Gly Val Ala Thr Asp Val Pro
65                  70                  75                  80

Ser Ala Thr Lys Arg Trp Gly Phe Arg Ser Gly Val Pro Pro Lys Val
                85                  90                  95

Val Asn Tyr Glu Ala Gly Glu Trp Ala Glu Asn Cys Tyr Asn Leu Glu
            100                 105                 110

Ile Lys Lys Pro Asp Gly Ser Glu Cys Leu Pro Ala Ala Pro Asp Gly
        115                 120                 125

Ile Arg Gly Phe Pro Arg Cys Arg Tyr Val His Lys Val Ser Gly Thr
    130                 135                 140

Gly Pro Cys Ala Gly Asp Phe Ala Phe His Lys Glu Gly Ala Phe Phe
145                 150                 155                 160

Leu Tyr Asp Arg Leu Ala Ser Thr Val Ile Tyr Arg Gly Thr Thr Phe
                165                 170                 175

Ala Glu Gly Val Val Ala Phe Leu Ile Leu Pro Gln Ala Lys Lys Asp
            180                 185                 190

Phe Phe Ser Ser His Pro Leu Arg Glu Pro Val Asn Ala Thr Glu Asp
```

```
            195                 200                 205
Pro Ser Ser Gly Tyr Tyr Ser Thr Thr Ile Arg Tyr Gln Ala Thr Gly
210                 215                 220

Phe Gly Thr Asn Glu Thr Glu Tyr Leu Phe Glu Val Asp Asn Leu Thr
225                 230                 235                 240

Tyr Val Gln Leu Glu Ser Arg Phe Thr Pro Gln Phe Leu Leu Gln Leu
                    245                 250                 255

Asn Glu Thr Ile Tyr Thr Ser Gly Lys Arg Ser Asn Thr Thr Gly Lys
                260                 265                 270

Leu Ile Trp Lys Val Asn Pro Glu Ile Asp Thr Thr Ile Gly Glu Trp
                    275                 280                 285

Ala Phe Trp Glu Thr Lys Lys Asn Leu Thr Arg Lys Ile Arg Ser Glu
                290                 295                 300

Glu Leu Ser Phe Thr Ala Val Ser His His Gln Asp Thr Gly Glu Glu
305                 310                 315                 320

Ser Ala Ser Ser Gly Lys Leu Gly Leu Ile Thr Asn Thr Ile Ala Gly
                    325                 330                 335

Val Ala Gly Leu Ile Thr Gly Gly Arg Arg Ala Arg Arg Glu Ala Ile
                340                 345                 350

Val Asn Ala Gln Pro Lys Cys Asn Pro Asn Leu His Tyr Trp Thr Thr
                355                 360                 365

Gln Asp Glu Gly Ala Ala Ile Gly Leu Ala Trp Ile Pro Tyr Phe Gly
370                 375                 380

Pro Ala Ala Glu Gly Ile Tyr Ile Glu Gly Leu Met His Asn Gln Asp
385                 390                 395                 400

Gly Leu Ile Cys Gly Leu Arg Gln Leu Ala Asn Glu Thr Thr Gln Ala
                    405                 410                 415

Leu Gln Leu Phe Leu Arg Ala Thr Thr Glu Leu Arg Thr Phe Ser Ile
                420                 425                 430

Leu Asn Arg Lys Ala Ile Asp Phe Leu Leu Gln Arg Trp Gly Gly Thr
                435                 440                 445

Cys His Ile Leu Gly Pro Asp Cys Cys Ile Glu Pro His Asp Trp Thr
                450                 455                 460

Lys Asn Ile Thr Asp Lys Ile Asp Gln Ile Ile His Asp Phe Val Asp
465                 470                 475                 480

Lys Thr Leu Pro Asp Gln Gly Asp Asn Asp Asn Trp Trp Thr Gly Trp
                    485                 490                 495

Arg Gln Trp Ile Pro Ala Gly Ile Gly Val Thr Gly Val Ile Ile Ala
                    500                 505                 510

Val Ile Ala Leu Phe Cys Ile Cys Lys Phe Val Phe
                515                 520

<210> SEQ ID NO 5
<211> LENGTH: 676
<212> TYPE: PRT
<213> ORGANISM: Ebola virus (Makona strain)

<400> SEQUENCE: 5

Met Gly Val Thr Gly Ile Leu Gln Leu Pro Arg Asp Arg Phe Lys Arg
1                   5                   10                  15

Thr Ser Phe Phe Leu Trp Val Ile Ile Leu Phe Gln Arg Thr Phe Ser
                20                  25                  30

Ile Pro Leu Gly Val Ile His Asn Ser Thr Leu Gln Val Ser Asp Val
                35                  40                  45
```

-continued

```
Asp Lys Leu Val Cys Arg Asp Lys Leu Ser Ser Thr Asn Gln Leu Arg
    50                  55                  60

Ser Val Gly Leu Asn Leu Glu Gly Asn Gly Val Ala Thr Asp Val Pro
65                  70                  75                  80

Ser Ala Thr Lys Arg Trp Gly Phe Arg Ser Gly Val Pro Pro Lys Val
                85                  90                  95

Val Asn Tyr Glu Ala Gly Glu Trp Ala Glu Asn Cys Tyr Asn Leu Glu
            100                 105                 110

Ile Lys Lys Pro Asp Gly Ser Glu Cys Leu Pro Ala Ala Pro Asp Gly
        115                 120                 125

Ile Arg Gly Phe Pro Arg Cys Arg Tyr Val His Lys Val Ser Gly Thr
    130                 135                 140

Gly Pro Cys Ala Gly Asp Phe Ala Phe His Lys Glu Gly Ala Phe Phe
145                 150                 155                 160

Leu Tyr Asp Arg Leu Ala Ser Thr Val Ile Tyr Arg Gly Thr Thr Phe
                165                 170                 175

Ala Glu Gly Val Val Ala Phe Leu Ile Leu Pro Gln Ala Lys Lys Asp
            180                 185                 190

Phe Phe Ser Ser His Pro Leu Arg Glu Pro Val Asn Ala Thr Glu Asp
        195                 200                 205

Pro Ser Ser Gly Tyr Tyr Ser Thr Thr Ile Arg Tyr Gln Ala Thr Gly
    210                 215                 220

Phe Gly Thr Asn Glu Thr Glu Tyr Leu Phe Glu Val Asp Asn Leu Thr
225                 230                 235                 240

Tyr Val Gln Leu Glu Ser Arg Phe Thr Pro Gln Phe Leu Leu Gln Leu
                245                 250                 255

Asn Glu Thr Ile Tyr Ala Ser Gly Lys Arg Ser Asn Thr Thr Gly Lys
            260                 265                 270

Leu Ile Trp Lys Val Asn Pro Glu Ile Asp Thr Thr Ile Gly Glu Trp
        275                 280                 285

Ala Phe Trp Glu Thr Lys Lys Asn Leu Thr Arg Lys Ile Arg Ser Glu
    290                 295                 300

Glu Leu Ser Phe Thr Ala Val Ser Asn Gly Pro Lys Asn Ile Ser Gly
305                 310                 315                 320

Gln Ser Pro Ala Arg Thr Ser Ser Asp Pro Glu Thr Asn Thr Thr Asn
                325                 330                 335

Glu Asp His Lys Ile Met Ala Ser Glu Asn Ser Ser Ala Met Val Gln
            340                 345                 350

Val His Ser Gln Gly Arg Lys Ala Ala Val Ser His Leu Thr Thr Leu
        355                 360                 365

Ala Thr Ile Ser Thr Ser Pro Gln Pro Pro Thr Thr Lys Thr Gly Pro
    370                 375                 380

Asp Asn Ser Thr His Asn Thr Pro Val Tyr Lys Leu Asp Ile Ser Glu
385                 390                 395                 400

Ala Thr Gln Val Gly Gln His Arg Arg Ala Asp Asn Asp Ser Thr
                405                 410                 415

Ala Ser Asp Thr Pro Ala Thr Thr Ala Ala Gly Pro Leu Lys Ala
            420                 425                 430

Glu Asn Thr Asn Thr Ser Lys Ser Ala Asp Ser Leu Asp Leu Ala Thr
        435                 440                 445

Thr Thr Ser Pro Gln Asn Tyr Ser Glu Thr Ala Gly Asn Asn Asn Thr
    450                 455                 460

His His Gln Asp Thr Gly Glu Glu Ser Ala Ser Ser Gly Lys Leu Gly
```

```
              465                 470                 475                 480
Leu Ile Thr Asn Thr Ile Ala Gly Val Ala Gly Leu Ile Thr Gly Gly
                485                 490                 495

Arg Arg Thr Arg Arg Glu Val Ile Val Asn Ala Gln Pro Lys Cys Asn
            500                 505                 510

Pro Asn Leu His Tyr Trp Thr Thr Gln Asp Glu Gly Ala Ala Ile Gly
            515                 520                 525

Leu Ala Trp Ile Pro Tyr Phe Gly Pro Ala Ala Glu Gly Ile Tyr Thr
            530                 535                 540

Glu Gly Leu Met His Asn Gln Asn Gly Leu Ile Cys Gly Leu Arg Gln
545                 550                 555                 560

Leu Ala Asn Glu Thr Thr Gln Ala Leu Gln Leu Phe Leu Arg Ala Thr
                565                 570                 575

Thr Glu Leu Arg Thr Phe Ser Ile Leu Asn Arg Lys Ala Ile Asp Phe
                580                 585                 590

Leu Leu Gln Arg Trp Gly Gly Thr Cys His Ile Leu Gly Pro Asp Cys
                595                 600                 605

Cys Ile Glu Pro His Asp Trp Thr Lys Asn Ile Thr Asp Lys Ile Asp
            610                 615                 620

Gln Ile Ile His Asp Phe Val Asp Lys Thr Leu Pro Asp Gln Gly Asp
625                 630                 635                 640

Asn Asp Asn Trp Trp Thr Gly Trp Arg Gln Trp Ile Pro Ala Gly Ile
                645                 650                 655

Gly Val Thr Gly Val Ile Ile Ala Val Ile Ala Leu Phe Cys Ile Cys
            660                 665                 670

Lys Phe Val Phe
            675

<210> SEQ ID NO 6
<211> LENGTH: 524
<212> TYPE: PRT
<213> ORGANISM: Ebola virus (Makona strain)

<400> SEQUENCE: 6

Met Gly Val Thr Gly Ile Leu Gln Leu Pro Arg Asp Arg Phe Lys Arg
1               5                   10                  15

Thr Ser Phe Phe Leu Trp Val Ile Ile Leu Phe Gln Arg Thr Phe Ser
                20                  25                  30

Ile Pro Leu Gly Val Ile His Asn Ser Thr Leu Gln Val Ser Asp Val
            35                  40                  45

Asp Lys Leu Val Cys Arg Asp Lys Leu Ser Ser Thr Asn Gln Leu Arg
        50                  55                  60

Ser Val Gly Leu Asn Leu Glu Gly Asn Gly Val Ala Thr Asp Val Pro
65                  70                  75                  80

Ser Ala Thr Lys Arg Trp Gly Phe Arg Ser Gly Val Pro Pro Lys Val
                85                  90                  95

Val Asn Tyr Glu Ala Gly Glu Trp Ala Glu Asn Cys Tyr Asn Leu Glu
            100                 105                 110

Ile Lys Lys Pro Asp Gly Ser Glu Cys Leu Pro Ala Ala Pro Asp Gly
        115                 120                 125

Ile Arg Gly Phe Pro Arg Cys Arg Tyr Val His Lys Val Ser Gly Thr
    130                 135                 140

Gly Pro Cys Ala Gly Asp Phe Ala Phe His Lys Glu Gly Ala Phe Phe
145                 150                 155                 160
```

-continued

```
Leu Tyr Asp Arg Leu Ala Ser Thr Val Ile Tyr Arg Gly Thr Thr Phe
            165                 170                 175
Ala Glu Gly Val Val Ala Phe Leu Ile Leu Pro Gln Ala Lys Lys Asp
        180                 185                 190
Phe Phe Ser Ser His Pro Leu Arg Glu Pro Val Asn Ala Thr Glu Asp
    195                 200                 205
Pro Ser Ser Gly Tyr Tyr Ser Thr Thr Ile Arg Tyr Gln Ala Thr Gly
210                 215                 220
Phe Gly Thr Asn Glu Thr Glu Tyr Leu Phe Glu Val Asp Asn Leu Thr
225                 230                 235                 240
Tyr Val Gln Leu Glu Ser Arg Phe Thr Pro Gln Phe Leu Leu Gln Leu
                245                 250                 255
Asn Glu Thr Ile Tyr Ala Ser Gly Lys Arg Ser Asn Thr Thr Gly Lys
            260                 265                 270
Leu Ile Trp Lys Val Asn Pro Glu Ile Asp Thr Thr Ile Gly Glu Trp
        275                 280                 285
Ala Phe Trp Glu Thr Lys Lys Asn Leu Thr Arg Lys Ile Arg Ser Glu
    290                 295                 300
Glu Leu Ser Phe Thr Ala Val Ser His His Gln Asp Thr Gly Glu Glu
305                 310                 315                 320
Ser Ala Ser Ser Gly Lys Leu Gly Leu Ile Thr Asn Thr Ile Ala Gly
                325                 330                 335
Val Ala Gly Leu Ile Thr Gly Gly Arg Arg Thr Arg Arg Glu Val Ile
            340                 345                 350
Val Asn Ala Gln Pro Lys Cys Asn Pro Asn Leu His Tyr Trp Thr Thr
        355                 360                 365
Gln Asp Glu Gly Ala Ala Ile Gly Leu Ala Trp Ile Pro Tyr Phe Gly
    370                 375                 380
Pro Ala Ala Glu Gly Ile Tyr Thr Glu Gly Leu Met His Asn Gln Asn
385                 390                 395                 400
Gly Leu Ile Cys Gly Leu Arg Gln Leu Ala Asn Glu Thr Thr Gln Ala
                405                 410                 415
Leu Gln Leu Phe Leu Arg Ala Thr Thr Glu Leu Arg Thr Phe Ser Ile
            420                 425                 430
Leu Asn Arg Lys Ala Ile Asp Phe Leu Leu Gln Arg Trp Gly Gly Thr
        435                 440                 445
Cys His Ile Leu Gly Pro Asp Cys Cys Ile Glu Pro His Asp Trp Thr
    450                 455                 460
Lys Asn Ile Thr Asp Lys Ile Asp Gln Ile Ile His Asp Phe Val Asp
465                 470                 475                 480
Lys Thr Leu Pro Asp Gln Gly Asp Asn Asp Asn Trp Trp Thr Gly Trp
                485                 490                 495
Arg Gln Trp Ile Pro Ala Gly Ile Gly Val Thr Gly Val Ile Ile Ala
            500                 505                 510
Val Ile Ala Leu Phe Cys Ile Cys Lys Phe Val Phe
        515                 520

<210> SEQ ID NO 7
<211> LENGTH: 676
<212> TYPE: PRT
<213> ORGANISM: Ebola virus (Boniface strain)

<400> SEQUENCE: 7

Met Glu Gly Leu Ser Leu Leu Gln Leu Pro Arg Asp Lys Phe Arg Lys
1               5                   10                  15
```

Ser Ser Phe Phe Val Trp Val Ile Ile Leu Phe Gln Lys Ala Phe Ser
            20                  25                  30

Met Pro Leu Gly Val Val Thr Asn Ser Thr Leu Glu Val Thr Glu Ile
        35                  40                  45

Asp Gln Leu Val Cys Lys Asp His Leu Ala Ser Thr Asp Gln Leu Lys
 50                  55                  60

Ser Val Gly Leu Asn Leu Glu Gly Ser Gly Val Ser Thr Asp Ile Pro
 65                  70                  75                  80

Ser Ala Thr Lys Arg Trp Gly Phe Arg Ser Gly Val Pro Pro Lys Val
                85                  90                  95

Phe Ser Tyr Glu Ala Gly Glu Trp Ala Glu Asn Cys Tyr Asn Leu Glu
            100                 105                 110

Ile Lys Lys Pro Asp Gly Ser Glu Cys Leu Pro Pro Pro Asp Gly
            115                 120                 125

Val Arg Gly Phe Pro Arg Cys Arg Tyr Val His Lys Ala Gln Gly Thr
 130                 135                 140

Gly Pro Cys Pro Gly Asp Tyr Ala Phe His Lys Asp Gly Ala Phe Phe
145                 150                 155                 160

Leu Tyr Asp Arg Leu Ala Ser Thr Val Ile Tyr Arg Gly Val Asn Phe
                165                 170                 175

Ala Glu Gly Val Ile Ala Phe Leu Ile Leu Ala Lys Pro Lys Glu Thr
            180                 185                 190

Phe Leu Gln Ser Pro Pro Ile Arg Glu Ala Val Asn Tyr Thr Glu Asn
            195                 200                 205

Thr Ser Ser Tyr Tyr Ala Thr Ser Tyr Leu Glu Tyr Glu Ile Glu Asn
 210                 215                 220

Phe Gly Ala Gln His Ser Thr Thr Leu Phe Lys Ile Asn Asn Thr
225                 230                 235                 240

Phe Val Leu Leu Asp Arg Pro His Thr Pro Gln Phe Leu Phe Gln Leu
                245                 250                 255

Asn Asp Thr Ile His Leu His Gln Gln Leu Ser Asn Thr Thr Gly Lys
            260                 265                 270

Leu Ile Trp Thr Leu Asp Ala Asn Ile Asn Ala Asp Ile Gly Glu Trp
            275                 280                 285

Ala Phe Trp Glu Asn Lys Lys Asn Leu Ser Glu Gln Leu Arg Gly Glu
            290                 295                 300

Glu Leu Ser Phe Glu Thr Leu Ser Leu Asn Glu Thr Glu Asp Asp Asp
305                 310                 315                 320

Ala Thr Ser Ser Arg Thr Thr Lys Gly Arg Ile Ser Asp Arg Ala Thr
                325                 330                 335

Arg Lys Tyr Ser Asp Leu Val Pro Lys Asp Ser Pro Gly Met Val Ser
            340                 345                 350

Leu His Val Pro Glu Gly Glu Thr Thr Leu Pro Ser Gln Asn Ser Thr
            355                 360                 365

Glu Gly Arg Arg Val Asp Val Asn Thr Gln Glu Thr Ile Thr Glu Thr
            370                 375                 380

Thr Ala Thr Ile Ile Gly Thr Asn Gly Asn Asn Met Gln Ile Ser Thr
385                 390                 395                 400

Ile Gly Thr Gly Leu Ser Ser Ser Gln Ile Leu Ser Ser Ser Pro Thr
                405                 410                 415

Met Ala Pro Ser Pro Glu Thr Gln Thr Ser Thr Thr Tyr Thr Pro Lys
            420                 425                 430

Leu Pro Val Met Thr Thr Glu Glu Ser Thr Thr Pro Arg Asn Ser
            435                 440                 445

Pro Gly Ser Thr Thr Glu Ala Pro Thr Leu Thr Thr Pro Glu Asn Ile
        450                 455                 460

Thr Thr Ala Val Lys Thr Val Leu Pro Gln Glu Ser Thr Ser Asn Gly
465                 470                 475                 480

Leu Ile Thr Ser Thr Val Thr Gly Ile Leu Gly Ser Leu Gly Leu Arg
                485                 490                 495

Lys Arg Ser Arg Arg Gln Val Asn Thr Arg Ala Thr Gly Lys Cys Asn
            500                 505                 510

Pro Asn Leu His Tyr Trp Thr Ala Gln Glu Gln His Asn Ala Ala Gly
        515                 520                 525

Ile Ala Trp Ile Pro Tyr Phe Gly Pro Gly Ala Glu Gly Ile Tyr Thr
    530                 535                 540

Glu Gly Leu Met His Asn Gln Asn Ala Leu Val Cys Gly Leu Arg Gln
545                 550                 555                 560

Leu Ala Asn Glu Thr Thr Gln Ala Leu Gln Leu Phe Leu Arg Ala Thr
                565                 570                 575

Thr Glu Leu Arg Thr Tyr Thr Ile Leu Asn Arg Lys Ala Ile Asp Phe
            580                 585                 590

Leu Leu Arg Arg Trp Gly Gly Thr Cys Arg Ile Leu Gly Pro Asp Cys
        595                 600                 605

Cys Ile Glu Pro His Asp Trp Thr Lys Asn Ile Thr Asp Lys Ile Asn
    610                 615                 620

Gln Ile Ile His Asp Phe Ile Asp Asn Pro Leu Pro Asn Gln Asp Asn
625                 630                 635                 640

Asp Asp Asn Trp Trp Thr Gly Trp Arg Gln Trp Ile Pro Ala Gly Ile
                645                 650                 655

Gly Ile Thr Gly Ile Ile Ile Ala Ile Ile Ala Leu Leu Cys Val Cys
            660                 665                 670

Lys Leu Leu Cys
        675

<210> SEQ ID NO 8
<211> LENGTH: 524
<212> TYPE: PRT
<213> ORGANISM: Ebola virus (Boniface strain)

<400> SEQUENCE: 8

Met Glu Gly Leu Ser Leu Leu Gln Leu Pro Arg Asp Lys Phe Arg Lys
1               5                   10                  15

Ser Ser Phe Phe Val Trp Val Ile Ile Leu Phe Gln Lys Ala Phe Ser
            20                  25                  30

Met Pro Leu Gly Val Val Thr Asn Ser Thr Leu Glu Val Thr Glu Ile
        35                  40                  45

Asp Gln Leu Val Cys Lys Asp His Leu Ala Ser Thr Asp Gln Leu Lys
    50                  55                  60

Ser Val Gly Leu Asn Leu Glu Gly Ser Gly Val Ser Thr Asp Ile Pro
65                  70                  75                  80

Ser Ala Thr Lys Arg Trp Gly Phe Arg Ser Gly Val Pro Pro Lys Val
                85                  90                  95

Phe Ser Tyr Glu Ala Gly Glu Trp Ala Glu Asn Cys Tyr Asn Leu Glu
            100                 105                 110

Ile Lys Lys Pro Asp Gly Ser Glu Cys Leu Pro Pro Pro Asp Gly
        115                 120                 125

Val Arg Gly Phe Pro Arg Cys Arg Tyr Val His Lys Ala Gln Gly Thr
130                 135                 140

Gly Pro Cys Pro Gly Asp Tyr Ala Phe His Lys Asp Gly Ala Phe Phe
145                 150                 155                 160

Leu Tyr Asp Arg Leu Ala Ser Thr Val Ile Tyr Arg Gly Val Asn Phe
                165                 170                 175

Ala Glu Gly Val Ile Ala Phe Leu Ile Leu Ala Lys Pro Lys Glu Thr
            180                 185                 190

Phe Leu Gln Ser Pro Pro Ile Arg Glu Ala Val Asn Tyr Thr Glu Asn
        195                 200                 205

Thr Ser Ser Tyr Tyr Ala Thr Ser Tyr Leu Glu Tyr Glu Ile Glu Asn
    210                 215                 220

Phe Gly Ala Gln His Ser Thr Thr Leu Phe Lys Ile Asn Asn Asn Thr
225                 230                 235                 240

Phe Val Leu Leu Asp Arg Pro His Thr Pro Gln Phe Leu Phe Gln Leu
                245                 250                 255

Asn Asp Thr Ile His Leu His Gln Gln Leu Ser Asn Thr Thr Gly Lys
            260                 265                 270

Leu Ile Trp Thr Leu Asp Ala Asn Ile Asn Ala Asp Ile Gly Glu Trp
        275                 280                 285

Ala Phe Trp Glu Asn Lys Lys Asn Leu Ser Glu Gln Leu Arg Gly Glu
    290                 295                 300

Glu Leu Ser Phe Glu Thr Leu Ser Thr Thr Ala Val Lys Thr Val Leu
305                 310                 315                 320

Pro Gln Glu Ser Thr Ser Asn Gly Leu Ile Thr Ser Thr Val Thr Gly
                325                 330                 335

Ile Leu Gly Ser Leu Gly Leu Arg Lys Arg Ser Arg Arg Gln Val Asn
            340                 345                 350

Thr Arg Ala Thr Gly Lys Cys Asn Pro Asn Leu His Tyr Trp Thr Ala
        355                 360                 365

Gln Glu Gln His Asn Ala Ala Gly Ile Ala Trp Ile Pro Tyr Phe Gly
    370                 375                 380

Pro Gly Ala Glu Gly Ile Tyr Thr Glu Gly Leu Met His Asn Gln Asn
385                 390                 395                 400

Ala Leu Val Cys Gly Leu Arg Gln Leu Ala Asn Glu Thr Thr Gln Ala
                405                 410                 415

Leu Gln Leu Phe Leu Arg Ala Thr Thr Glu Leu Arg Thr Tyr Thr Ile
            420                 425                 430

Leu Asn Arg Lys Ala Ile Asp Phe Leu Leu Arg Arg Trp Gly Gly Thr
        435                 440                 445

Cys Arg Ile Leu Gly Pro Asp Cys Cys Ile Glu Pro His Asp Trp Thr
    450                 455                 460

Lys Asn Ile Thr Asp Lys Ile Asn Gln Ile Ile His Asp Phe Ile Asp
465                 470                 475                 480

Asn Pro Leu Pro Asn Gln Asp Asn Asp Asp Asn Trp Trp Thr Gly Trp
                485                 490                 495

Arg Gln Trp Ile Pro Ala Gly Ile Gly Ile Thr Gly Ile Ile Ile Ala
            500                 505                 510

Ile Ile Ala Leu Leu Cys Val Cys Lys Leu Leu Cys
        515                 520

<210> SEQ ID NO 9
<211> LENGTH: 676

<212> TYPE: PRT
<213> ORGANISM: Ebola virus (Gulu strain)

<400> SEQUENCE: 9

Met Gly Gly Leu Ser Leu Leu Gln Leu Pro Arg Asp Lys Phe Arg Lys
1               5                   10                  15

Ser Ser Phe Phe Val Trp Val Ile Ile Leu Phe Gln Lys Ala Phe Ser
            20                  25                  30

Met Pro Leu Gly Val Val Thr Asn Ser Thr Leu Glu Val Thr Glu Ile
        35                  40                  45

Asp Gln Leu Val Cys Lys Asp His Leu Ala Ser Thr Asp Gln Leu Lys
    50                  55                  60

Ser Val Gly Leu Asn Leu Glu Gly Ser Gly Val Ser Thr Asp Ile Pro
65                  70                  75                  80

Ser Ala Thr Lys Arg Trp Gly Phe Arg Ser Gly Val Pro Pro Lys Val
                85                  90                  95

Val Ser Tyr Glu Ala Gly Glu Trp Ala Glu Asn Cys Tyr Asn Leu Glu
            100                 105                 110

Ile Lys Lys Pro Asp Gly Ser Glu Cys Leu Pro Pro Pro Pro Asp Gly
        115                 120                 125

Val Arg Gly Phe Pro Arg Cys Arg Tyr Val His Lys Ala Gln Gly Thr
    130                 135                 140

Gly Pro Cys Pro Gly Asp Tyr Ala Phe His Lys Asp Gly Ala Phe Phe
145                 150                 155                 160

Leu Tyr Asp Arg Leu Ala Ser Thr Val Ile Tyr Arg Gly Val Asn Phe
                165                 170                 175

Ala Glu Gly Val Ile Ala Phe Leu Ile Leu Ala Lys Pro Lys Glu Thr
            180                 185                 190

Phe Leu Gln Ser Pro Pro Ile Arg Glu Ala Val Asn Tyr Thr Glu Asn
        195                 200                 205

Thr Ser Ser Tyr Tyr Ala Thr Ser Tyr Leu Glu Tyr Glu Ile Glu Asn
210                 215                 220

Phe Gly Ala Gln His Ser Thr Thr Leu Phe Lys Ile Asp Asn Asn Thr
225                 230                 235                 240

Phe Val Arg Leu Asp Arg Pro His Thr Pro Gln Phe Leu Phe Gln Leu
                245                 250                 255

Asn Asp Thr Ile His Leu His Gln Gln Leu Ser Asn Thr Thr Gly Arg
            260                 265                 270

Leu Ile Trp Thr Leu Asp Ala Asn Ile Asn Ala Asp Ile Gly Glu Trp
        275                 280                 285

Ala Phe Trp Glu Asn Lys Lys Asn Leu Ser Glu Gln Leu Arg Gly Glu
    290                 295                 300

Glu Leu Ser Phe Glu Ala Leu Ser Leu Asn Glu Thr Glu Asp Asp Asp
305                 310                 315                 320

Ala Ala Ser Ser Arg Ile Thr Lys Gly Arg Ile Ser Asp Arg Ala Thr
                325                 330                 335

Arg Lys Tyr Ser Asp Leu Val Pro Lys Asn Ser Pro Gly Met Val Pro
            340                 345                 350

Leu His Ile Pro Glu Gly Glu Thr Thr Leu Pro Ser Gln Asn Ser Thr
        355                 360                 365

Glu Gly Arg Arg Val Gly Val Asn Thr Gln Gly Thr Ile Thr Glu Thr
370                 375                 380

Ala Ala Thr Ile Ile Gly Thr Asn Gly Asn His Met Gln Ile Ser Thr
385                 390                 395                 400

Ile Gly Ile Arg Pro Ser Ser Gln Ile Pro Ser Ser Pro Thr
            405                 410                 415

Thr Ala Pro Ser Pro Glu Ala Gln Thr Pro Thr Thr His Thr Ser Gly
        420                 425                 430

Pro Ser Val Met Ala Thr Glu Glu Pro Thr Thr Pro Gly Ser Ser
            435                 440                 445

Pro Gly Pro Thr Thr Glu Ala Pro Thr Leu Thr Thr Pro Glu Asn Ile
    450                 455                 460

Thr Thr Ala Val Lys Thr Val Leu Pro Gln Glu Ser Thr Ser Asn Gly
465                 470                 475                 480

Leu Ile Thr Ser Thr Val Thr Gly Ile Leu Gly Ser Leu Gly Leu Arg
                485                 490                 495

Lys Arg Ser Arg Arg Gln Thr Asn Thr Lys Ala Thr Gly Lys Cys Asn
            500                 505                 510

Pro Asn Leu His Tyr Trp Thr Ala Gln Glu Gln His Asn Ala Ala Gly
        515                 520                 525

Ile Ala Trp Ile Pro Tyr Phe Gly Pro Gly Ala Glu Gly Ile Tyr Thr
    530                 535                 540

Glu Gly Leu Met His Asn Gln Asn Ala Leu Val Cys Gly Leu Arg Gln
545                 550                 555                 560

Leu Ala Asn Glu Thr Thr Gln Ala Leu Gln Leu Phe Leu Arg Ala Thr
                565                 570                 575

Thr Glu Leu Arg Thr Tyr Thr Ile Leu Asn Arg Lys Ala Ile Asp Phe
            580                 585                 590

Leu Leu Arg Arg Trp Gly Gly Thr Cys Arg Ile Leu Gly Pro Asp Cys
        595                 600                 605

Cys Ile Glu Pro His Asp Trp Thr Lys Asn Ile Thr Asp Lys Ile Asn
    610                 615                 620

Gln Ile Ile His Asp Phe Ile Asp Asn Pro Leu Pro Asn Gln Asp Asn
625                 630                 635                 640

Asp Asp Asn Trp Trp Thr Gly Trp Arg Gln Trp Ile Pro Ala Gly Ile
                645                 650                 655

Gly Ile Thr Gly Ile Ile Ile Ala Ile Ile Ala Leu Leu Cys Val Cys
            660                 665                 670

Lys Leu Leu Cys
        675

<210> SEQ ID NO 10
<211> LENGTH: 524
<212> TYPE: PRT
<213> ORGANISM: Ebola virus (Gulu strain)

<400> SEQUENCE: 10

Met Gly Gly Leu Ser Leu Leu Gln Leu Pro Arg Asp Lys Phe Arg Lys
1               5                   10                  15

Ser Ser Phe Phe Val Trp Val Ile Ile Leu Phe Gln Lys Ala Phe Ser
            20                  25                  30

Met Pro Leu Gly Val Val Thr Asn Ser Thr Leu Glu Val Thr Glu Ile
        35                  40                  45

Asp Gln Leu Val Cys Lys Asp His Leu Ala Ser Thr Asp Gln Leu Lys
    50                  55                  60

Ser Val Gly Leu Asn Leu Glu Gly Ser Gly Val Ser Thr Asp Ile Pro
65                  70                  75                  80

Ser Ala Thr Lys Arg Trp Gly Phe Arg Ser Gly Val Pro Pro Lys Val

```
                85                  90                  95
Val Ser Tyr Glu Ala Gly Glu Trp Ala Glu Asn Cys Tyr Asn Leu Glu
            100                 105                 110
Ile Lys Lys Pro Asp Gly Ser Glu Cys Leu Pro Pro Pro Asp Gly
            115                 120                 125
Val Arg Gly Phe Pro Arg Cys Arg Tyr Val His Lys Ala Gln Gly Thr
            130                 135                 140
Gly Pro Cys Pro Gly Asp Tyr Ala Phe His Lys Asp Gly Ala Phe Phe
145                 150                 155                 160
Leu Tyr Asp Arg Leu Ala Ser Thr Val Ile Tyr Arg Gly Val Asn Phe
                165                 170                 175
Ala Glu Gly Val Ile Ala Phe Leu Ile Leu Ala Lys Pro Lys Glu Thr
                180                 185                 190
Phe Leu Gln Ser Pro Pro Ile Arg Glu Ala Val Asn Tyr Thr Glu Asn
                195                 200                 205
Thr Ser Ser Tyr Tyr Ala Thr Ser Tyr Leu Glu Tyr Glu Ile Glu Asn
            210                 215                 220
Phe Gly Ala Gln His Ser Thr Thr Leu Phe Lys Ile Asp Asn Asn Thr
225                 230                 235                 240
Phe Val Arg Leu Asp Arg Pro His Thr Pro Gln Phe Leu Phe Gln Leu
                245                 250                 255
Asn Asp Thr Ile His Leu His Gln Gln Leu Ser Asn Thr Thr Gly Arg
                260                 265                 270
Leu Ile Trp Thr Leu Asp Ala Asn Ile Asn Ala Asp Ile Gly Glu Trp
                275                 280                 285
Ala Phe Trp Glu Asn Lys Lys Asn Leu Ser Glu Gln Leu Arg Gly Glu
            290                 295                 300
Glu Leu Ser Phe Glu Ala Leu Ser Thr Thr Ala Val Lys Thr Val Leu
305                 310                 315                 320
Pro Gln Glu Ser Thr Ser Asn Gly Leu Ile Thr Ser Thr Val Thr Gly
                325                 330                 335
Ile Leu Gly Ser Leu Gly Leu Arg Lys Arg Ser Arg Arg Gln Thr Asn
                340                 345                 350
Thr Lys Ala Thr Gly Lys Cys Asn Pro Asn Leu His Tyr Trp Thr Ala
                355                 360                 365
Gln Glu Gln His Asn Ala Ala Gly Ile Ala Trp Ile Pro Tyr Phe Gly
            370                 375                 380
Pro Gly Ala Glu Gly Ile Tyr Thr Glu Gly Leu Met His Asn Gln Asn
385                 390                 395                 400
Ala Leu Val Cys Gly Leu Arg Gln Leu Ala Asn Glu Thr Thr Gln Ala
                405                 410                 415
Leu Gln Leu Phe Leu Arg Ala Thr Thr Glu Leu Arg Thr Tyr Thr Ile
                420                 425                 430
Leu Asn Arg Lys Ala Ile Asp Phe Leu Leu Arg Arg Trp Gly Gly Thr
                435                 440                 445
Cys Arg Ile Leu Gly Pro Asp Cys Cys Ile Glu Pro His Asp Trp Thr
                450                 455                 460
Lys Asn Ile Thr Asp Lys Ile Asn Gln Ile Ile His Asp Phe Ile Asp
465                 470                 475                 480
Asn Pro Leu Pro Asn Gln Asp Asn Asp Asp Asn Trp Trp Thr Gly Trp
                485                 490                 495
Arg Gln Trp Ile Pro Ala Gly Ile Gly Ile Thr Gly Ile Ile Ile Ala
                500                 505                 510
```

```
Ile Ile Ala Leu Leu Cys Val Cys Lys Leu Leu Cys
        515                 520
```

<210> SEQ ID NO 11
<211> LENGTH: 676
<212> TYPE: PRT
<213> ORGANISM: Bundibugyo virus (tc

```
                355                 360                 365
Thr Val Pro Thr Thr Leu Ile Pro Asp Thr Met Glu Glu Gln Thr Thr
        370                 375                 380

Ser His Tyr Glu Pro Pro Asn Ile Ser Arg Asn His Gln Glu Arg Asn
385                 390                 395                 400

Asn Thr Ala His Pro Glu Thr Leu Ala Asn Asn Pro Pro Asp Asn Thr
                405                 410                 415

Thr Pro Ser Thr Pro Pro Gln Asp Gly Glu Arg Thr Ser Ser His Thr
            420                 425                 430

Thr Pro Ser Pro Arg Pro Val Pro Thr Ser Thr Ile His Pro Thr Thr
        435                 440                 445

Arg Glu Thr His Ile Pro Thr Thr Met Thr Thr Ser His Asp Thr Asp
    450                 455                 460

Ser Asn Arg Pro Asn Pro Ile Asp Ile Ser Glu Ser Thr Glu Pro Gly
465                 470                 475                 480

Pro Leu Thr Asn Thr Thr Arg Gly Ala Ala Asn Leu Leu Thr Gly Ser
                485                 490                 495

Arg Arg Thr Arg Arg Glu Ile Thr Leu Arg Thr Gln Ala Lys Cys Asn
            500                 505                 510

Pro Asn Leu His Tyr Trp Thr Thr Gln Asp Glu Gly Ala Ala Ile Gly
        515                 520                 525

Leu Ala Trp Ile Pro Tyr Phe Gly Pro Ala Ala Glu Gly Ile Tyr Thr
    530                 535                 540

Glu Gly Ile Met His Asn Gln Asn Gly Leu Ile Cys Gly Leu Arg Gln
545                 550                 555                 560

Leu Ala Asn Glu Thr Thr Gln Ala Leu Gln Leu Phe Leu Arg Ala Thr
                565                 570                 575

Thr Glu Leu Arg Thr Phe Ser Ile Leu Asn Arg Lys Ala Ile Asp Phe
            580                 585                 590

Leu Leu Gln Arg Trp Gly Gly Thr Cys His Ile Leu Gly Pro Asp Cys
        595                 600                 605

Cys Ile Glu Pro His Asp Trp Thr Lys Asn Ile Thr Asp Lys Ile Asp
    610                 615                 620

Gln Ile Ile His Asp Phe Ile Asp Lys Pro Leu Pro Asp Gln Thr Asp
625                 630                 635                 640

Asn Asp Asn Trp Trp Thr Gly Trp Arg Gln Trp Val Pro Ala Gly Ile
                645                 650                 655

Gly Ile Thr Gly Val Ile Ile Ala Val Ile Ala Leu Leu Cys Ile Cys
            660                 665                 670

Lys Phe Leu Leu
        675

<210> SEQ ID NO 12
<211> LENGTH: 524
<212> TYPE: PRT
<213> ORGANISM: Bundibugyo virus (tc/UGA/2007/Bundibugyo-200706291)

<400> SEQUENCE: 12

Met Val Thr Ser Gly Ile Leu Gln Leu Pro Arg Glu Arg Phe Arg Lys
1               5                   10                  15

Thr Ser Phe Phe Val Trp Val Ile Ile Leu Phe His Lys Val Phe Pro
                20                  25                  30

Ile Pro Leu Gly Val Val His Asn Asn Thr Leu Gln Val Ser Asp Ile
            35                  40                  45
```

```
Asp Lys Leu Val Cys Arg Asp Lys Leu Ser Ser Thr Ser Gln Leu Lys
    50              55                  60

Ser Val Gly Leu Asn Leu Glu Gly Asn Gly Val Ala Thr Asp Val Pro
65              70              75                      80

Thr Ala Thr Lys Arg Trp Gly Phe Arg Ala Gly Val Pro Pro Lys Val
                85              90                  95

Val Asn Tyr Glu Ala Gly Glu Trp Ala Glu Asn Cys Tyr Asn Leu Asp
            100             105             110

Ile Lys Lys Ala Asp Gly Ser Glu Cys Leu Pro Glu Ala Pro Glu Gly
        115             120             125

Val Arg Gly Phe Pro Arg Cys Arg Tyr Val His Lys Val Ser Gly Thr
    130             135             140

Gly Pro Cys Pro Glu Gly Tyr Ala Phe His Lys Glu Gly Ala Phe Phe
145             150             155                     160

Leu Tyr Asp Arg Leu Ala Ser Thr Ile Ile Tyr Arg Ser Thr Thr Phe
                165             170             175

Ser Glu Gly Val Val Ala Phe Leu Ile Leu Pro Glu Thr Lys Lys Asp
            180             185             190

Phe Phe Gln Ser Pro Pro Leu His Glu Pro Ala Asn Met Thr Thr Asp
        195             200             205

Pro Ser Ser Tyr Tyr His Thr Val Thr Leu Asn Tyr Val Ala Asp Asn
    210             215             220

Phe Gly Thr Asn Met Thr Asn Phe Leu Phe Gln Val Asp His Leu Thr
225             230             235                     240

Tyr Val Gln Leu Glu Pro Arg Phe Thr Pro Gln Phe Leu Val Gln Leu
                245             250             255

Asn Glu Thr Ile Tyr Thr Asn Gly Arg Arg Ser Asn Thr Thr Gly Thr
            260             265             270

Leu Ile Trp Lys Val Asn Pro Thr Val Asp Thr Gly Val Gly Glu Trp
        275             280             285

Ala Phe Trp Glu Asn Lys Lys Asn Phe Thr Lys Thr Leu Ser Ser Glu
    290             295             300

Glu Leu Ser Val Ile Phe Val Pro Ser Asn Arg Pro Asn Pro Ile Asp
305             310             315                     320

Ile Ser Glu Ser Thr Glu Pro Gly Pro Leu Thr Asn Thr Thr Arg Gly
                325             330             335

Ala Ala Asn Leu Leu Thr Gly Ser Arg Arg Thr Arg Arg Glu Ile Thr
            340             345             350

Leu Arg Thr Gln Ala Lys Cys Asn Pro Asn Leu His Tyr Trp Thr Thr
        355             360             365

Gln Asp Glu Gly Ala Ala Ile Gly Leu Ala Trp Ile Pro Tyr Phe Gly
    370             375             380

Pro Ala Ala Glu Gly Ile Tyr Thr Glu Gly Ile Met His Asn Gln Asn
385             390             395                     400

Gly Leu Ile Cys Gly Leu Arg Gln Leu Ala Asn Glu Thr Thr Gln Ala
                405             410             415

Leu Gln Leu Phe Leu Arg Ala Thr Thr Glu Leu Arg Thr Phe Ser Ile
            420             425             430

Leu Asn Arg Lys Ala Ile Asp Phe Leu Leu Gln Arg Trp Gly Gly Thr
        435             440             445

Cys His Ile Leu Gly Pro Asp Cys Cys Ile Glu Pro His Asp Trp Thr
    450             455             460

Lys Asn Ile Thr Asp Lys Ile Asp Gln Ile Ile His Asp Phe Ile Asp
```

```
                465                 470                 475                 480

Lys Pro Leu Pro Asp Gln Thr Asp Asn Asp Asn Trp Trp Thr Gly Trp
                            485                 490                 495

Arg Gln Trp Val Pro Ala Gly Ile Gly Ile Thr Gly Val Ile Ile Ala
                        500                 505                 510

Val Ile Ala Leu Leu Cys Ile Cys Lys Phe Leu Leu
                        515                 520

<210> SEQ ID NO 13
<211> LENGTH: 677
<212> TYPE: PRT
<213> ORGANISM: Reston virus (Pennsylvania strain)

<400> SEQUENCE: 13

Met Gly Ser Gly Tyr Gln Leu Leu Gln Leu Pro Arg Glu Arg Phe Arg
            1               5                   10                  15

Lys Thr Ser Phe Leu Val Trp Val Ile Leu Phe Gln Arg Ala Ile
                            20                  25                  30

Ser Met Pro Leu Gly Ile Val Thr Asn Ser Thr Leu Lys Ala Thr Glu
                        35                  40                  45

Ile Asp Gln Leu Val Cys Arg Asp Lys Leu Ser Ser Thr Ser Gln Leu
                50                  55                  60

Lys Ser Val Gly Leu Asn Leu Glu Gly Asn Gly Ile Ala Thr Asp Val
            65                  70                  75                  80

Pro Ser Ala Thr Lys Arg Trp Gly Phe Arg Ser Gly Val Pro Pro Lys
                            85                  90                  95

Val Val Ser Tyr Glu Ala Gly Glu Trp Ala Glu Asn Cys Tyr Asn Leu
                        100                 105                 110

Glu Ile Lys Lys Ser Asp Gly Ser Glu Cys Leu Pro Leu Pro Pro Asp
                    115                 120                 125

Gly Val Arg Gly Phe Pro Arg Cys Arg Tyr Val His Lys Val Gln Gly
                130                 135                 140

Thr Gly Pro Cys Pro Gly Asp Leu Ala Phe His Lys Asn Gly Ala Phe
            145                 150                 155                 160

Phe Leu Tyr Asp Arg Leu Ala Ser Thr Val Ile Tyr Arg Gly Thr Thr
                            165                 170                 175

Phe Ala Glu Gly Val Val Ala Phe Leu Ile Leu Ser Glu Pro Lys Lys
                        180                 185                 190

His Phe Trp Lys Ala Thr Pro Ala His Glu Pro Val Asn Thr Thr Asp
                    195                 200                 205

Asp Ser Thr Ser Tyr Tyr Met Thr Leu Thr Leu Ser Tyr Glu Met Ser
                210                 215                 220

Asn Phe Gly Gly Asn Glu Ser Asn Thr Leu Phe Lys Val Asp Asn His
            225                 230                 235                 240

Thr Tyr Val Gln Leu Asp Arg Pro His Thr Pro Gln Phe Leu Val Gln
                            245                 250                 255

Leu Asn Glu Thr Leu Arg Arg Asn Asn Arg Leu Ser Asn Ser Thr Gly
                        260                 265                 270

Arg Leu Thr Trp Thr Leu Asp Pro Lys Ile Glu Pro Asp Val Gly Glu
                    275                 280                 285

Trp Ala Phe Trp Glu Thr Lys Lys Asn Phe Ser Gln Gln Leu His Gly
                290                 295                 300

Glu Asn Leu His Phe Gln Ile Pro Ser Thr His Thr Asn Asn Ser Ser
            305                 310                 315                 320
```

```
Asp Gln Ser Pro Ala Gly Thr Val Gln Gly Lys Ile Ser Tyr His Pro
                325                 330                 335
Pro Ala Asn Asn Ser Glu Leu Val Pro Thr Asp Ser Pro Val Val
            340                 345                 350
Ser Val Leu Thr Ala Gly Arg Thr Glu Glu Met Ser Thr Gln Gly Leu
        355                 360                 365
Thr Asn Gly Glu Thr Ile Thr Gly Phe Thr Ala Asn Pro Met Thr Thr
    370                 375                 380
Thr Ile Ala Pro Ser Pro Thr Met Thr Ser Glu Val Asp Asn Asn Val
385                 390                 395                 400
Pro Ser Glu Gln Pro Asn Asn Thr Ala Ser Ile Glu Asp Ser Pro Pro
                405                 410                 415
Ser Ala Ser Asn Glu Thr Ile Tyr His Ser Glu Met Asp Pro Ile Gln
            420                 425                 430
Gly Ser Asn Asn Ser Ala Gln Ser Pro Gln Thr Lys Thr Thr Pro Ala
        435                 440                 445
Pro Thr Thr Ser Pro Met Thr Gln Asp Pro Gln Glu Thr Ala Asn Ser
    450                 455                 460
Ser Lys Pro Gly Thr Ser Pro Gly Ser Ala Ala Gly Pro Ser Gln Pro
465                 470                 475                 480
Gly Leu Thr Ile Asn Thr Val Ser Lys Val Ala Asp Ser Leu Ser Pro
                485                 490                 495
Thr Arg Lys Gln Lys Arg Ser Val Arg Gln Asn Thr Ala Asn Lys Cys
            500                 505                 510
Asn Pro Asp Leu Tyr Tyr Trp Thr Ala Val Asp Glu Gly Ala Ala Val
        515                 520                 525
Gly Leu Ala Trp Ile Pro Tyr Phe Gly Pro Ala Ala Glu Gly Ile Tyr
    530                 535                 540
Ile Glu Gly Val Met His Asn Gln Asn Gly Leu Ile Cys Gly Leu Arg
545                 550                 555                 560
Gln Leu Ala Asn Glu Thr Thr Gln Ala Leu Gln Leu Phe Leu Arg Ala
                565                 570                 575
Thr Thr Glu Leu Arg Thr Tyr Ser Leu Leu Asn Arg Lys Ala Ile Asp
            580                 585                 590
Phe Leu Leu Gln Arg Trp Gly Gly Thr Cys Arg Ile Leu Gly Pro Ser
        595                 600                 605
Cys Cys Ile Glu Pro His Asp Trp Thr Lys Asn Ile Thr Asp Glu Ile
    610                 615                 620
Asn Gln Ile Lys His Asp Phe Ile Asp Asn Pro Leu Pro Asp His Gly
625                 630                 635                 640
Asp Asp Leu Asn Leu Trp Thr Gly Trp Arg Gln Trp Ile Pro Ala Gly
                645                 650                 655
Ile Gly Ile Ile Gly Val Ile Ile Ala Ile Ile Ala Leu Leu Cys Ile
            660                 665                 670
Cys Lys Ile Leu Cys
        675

<210> SEQ ID NO 14
<211> LENGTH: 525
<212> TYPE: PRT
<213> ORGANISM: Reston virus (Pennsylvania strain)

<400> SEQUENCE: 14

Met Gly Ser Gly Tyr Gln Leu Leu Gln Leu Pro Arg Glu Arg Phe Arg
1               5                   10                  15
```

-continued

```
Lys Thr Ser Phe Leu Val Trp Val Ile Ile Leu Phe Gln Arg Ala Ile
             20                  25                  30

Ser Met Pro Leu Gly Ile Val Thr Asn Ser Thr Leu Lys Ala Thr Glu
             35                  40                  45

Ile Asp Gln Leu Val Cys Arg Asp Lys Leu Ser Ser Thr Ser Gln Leu
 50                  55                  60

Lys Ser Val Gly Leu Asn Leu Glu Gly Asn Gly Ile Ala Thr Asp Val
 65                  70                  75                  80

Pro Ser Ala Thr Lys Arg Trp Gly Phe Arg Ser Gly Val Pro Pro Lys
             85                  90                  95

Val Val Ser Tyr Glu Ala Gly Glu Trp Ala Glu Asn Cys Tyr Asn Leu
            100                 105                 110

Glu Ile Lys Lys Ser Asp Gly Ser Glu Cys Leu Pro Leu Pro Pro Asp
            115                 120                 125

Gly Val Arg Gly Phe Pro Arg Cys Arg Tyr Val His Lys Val Gln Gly
            130                 135                 140

Thr Gly Pro Cys Pro Gly Asp Leu Ala Phe His Lys Asn Gly Ala Phe
145                 150                 155                 160

Phe Leu Tyr Asp Arg Leu Ala Ser Thr Val Ile Tyr Arg Gly Thr Thr
            165                 170                 175

Phe Ala Glu Gly Val Val Ala Phe Leu Ile Leu Ser Glu Pro Lys Lys
            180                 185                 190

His Phe Trp Lys Ala Thr Pro Ala His Glu Pro Val Asn Thr Thr Asp
            195                 200                 205

Asp Ser Thr Ser Tyr Tyr Met Thr Leu Thr Leu Ser Tyr Glu Met Ser
210                 215                 220

Asn Phe Gly Gly Asn Glu Ser Asn Thr Leu Phe Lys Val Asp Asn His
225                 230                 235                 240

Thr Tyr Val Gln Leu Asp Arg Pro His Thr Pro Gln Phe Leu Val Gln
            245                 250                 255

Leu Asn Glu Thr Leu Arg Arg Asn Asn Arg Leu Ser Asn Ser Thr Gly
            260                 265                 270

Arg Leu Thr Trp Thr Leu Asp Pro Lys Ile Glu Pro Asp Val Gly Glu
            275                 280                 285

Trp Ala Phe Trp Glu Thr Lys Lys Asn Phe Ser Gln Gln Leu His Gly
            290                 295                 300

Glu Asn Leu His Phe Gln Ile Pro Ser Lys Pro Gly Thr Ser Pro Gly
305                 310                 315                 320

Ser Ala Ala Gly Pro Ser Gln Pro Gly Leu Thr Ile Asn Thr Val Ser
            325                 330                 335

Lys Val Ala Asp Ser Leu Ser Pro Thr Arg Lys Gln Lys Arg Ser Val
            340                 345                 350

Arg Gln Asn Thr Ala Asn Lys Cys Asn Pro Asp Leu Tyr Tyr Trp Thr
            355                 360                 365

Ala Val Asp Glu Gly Ala Ala Val Gly Leu Ala Trp Ile Pro Tyr Phe
            370                 375                 380

Gly Pro Ala Ala Glu Gly Ile Tyr Ile Glu Gly Val Met His Asn Gln
385                 390                 395                 400

Asn Gly Leu Ile Cys Gly Leu Arg Gln Leu Ala Asn Glu Thr Thr Gln
            405                 410                 415

Ala Leu Gln Leu Phe Leu Arg Ala Thr Thr Glu Leu Arg Thr Tyr Ser
            420                 425                 430
```

```
Leu Leu Asn Arg Lys Ala Ile Asp Phe Leu Leu Gln Arg Trp Gly Gly
        435                 440                 445

Thr Cys Arg Ile Leu Gly Pro Ser Cys Cys Ile Glu Pro His Asp Trp
    450                 455                 460

Thr Lys Asn Ile Thr Asp Glu Ile Asn Gln Ile Lys His Asp Phe Ile
465                 470                 475                 480

Asp Asn Pro Leu Pro Asp His Gly Asp Leu Asn Leu Trp Thr Gly
                485                 490                 495

Trp Arg Gln Trp Ile Pro Ala Gly Ile Gly Ile Ile Gly Val Ile Ile
                500                 505                 510

Ala Ile Ile Ala Leu Leu Cys Ile Cys Lys Ile Leu Cys
        515                 520                 525

<210> SEQ ID NO 15
<211> LENGTH: 676
<212> TYPE: PRT
<213> ORGANISM: Tai Forrest virus (tc/CIV/1994/Pauleoula-CI strain)

<400> SEQUENCE: 15

Met Gly Ala Ser Gly Ile Leu Gln Leu Pro Arg Glu Arg Phe Arg Lys
1               5                   10                  15

Thr Ser Phe Phe Val Trp Val Ile Ile Leu Phe His Lys Val Phe Ser
            20                  25                  30

Ile Pro Leu Gly Val Val His Asn Asn Thr Leu Gln Val Ser Asp Ile
        35                  40                  45

Asp Lys Phe Val Cys Arg Asp Lys Leu Ser Ser Thr Ser Gln Leu Lys
    50                  55                  60

Ser Val Gly Leu Asn Leu Glu Gly Asn Gly Val Ala Thr Asp Val Pro
65                  70                  75                  80

Thr Ala Thr Lys Arg Trp Gly Phe Arg Ala Gly Val Pro Pro Lys Val
                85                  90                  95

Val Asn Cys Glu Ala Gly Glu Trp Ala Glu Asn Cys Tyr Asn Leu Ala
            100                 105                 110

Ile Lys Lys Val Asp Gly Ser Glu Cys Leu Pro Glu Ala Pro Glu Gly
        115                 120                 125

Val Arg Asp Phe Pro Arg Cys Arg Tyr Val His Lys Val Ser Gly Thr
    130                 135                 140

Gly Pro Cys Pro Gly Gly Leu Ala Phe His Lys Glu Gly Ala Phe Phe
145                 150                 155                 160

Leu Tyr Asp Arg Leu Ala Ser Thr Ile Ile Tyr Arg Gly Thr Thr Phe
                165                 170                 175

Ala Glu Gly Val Ile Ala Phe Leu Ile Leu Pro Lys Ala Arg Lys Asp
            180                 185                 190

Phe Phe Gln Ser Pro Pro Leu His Glu Pro Ala Asn Met Thr Thr Asp
        195                 200                 205

Pro Ser Ser Tyr His Thr Thr Thr Ile Asn Tyr Val Val Asp Asn
    210                 215                 220

Phe Gly Thr Asn Thr Thr Glu Phe Leu Phe Gln Val Asp His Leu Thr
225                 230                 235                 240

Tyr Val Gln Leu Glu Ala Arg Phe Thr Pro Gln Phe Leu Val Leu Leu
                245                 250                 255

Asn Glu Thr Ile Tyr Ser Asp Asn Arg Arg Ser Asn Thr Thr Gly Lys
            260                 265                 270

Leu Ile Trp Lys Ile Asn Pro Thr Val Asp Thr Ser Met Gly Glu Trp
        275                 280                 285
```

-continued

```
Ala Phe Trp Glu Asn Lys Lys Asn Phe Thr Lys Thr Leu Ser Ser Glu
        290             295             300

Glu Leu Ser Phe Val Pro Val Pro Glu Thr Gln Asn Gln Val Leu Asp
305             310             315             320

Thr Thr Ala Thr Val Ser Pro Pro Ile Ser Ala His Asn His Ala Ala
                325             330             335

Glu Asp His Lys Glu Leu Val Ser Glu Asp Ser Thr Pro Val Val Gln
            340             345             350

Met Gln Asn Ile Lys Gly Lys Asp Thr Met Pro Thr Thr Val Thr Gly
        355             360             365

Val Pro Thr Thr Thr Pro Ser Pro Phe Pro Ile Asn Ala Arg Asn Thr
370             375             380

Asp His Thr Lys Ser Phe Ile Gly Leu Glu Gly Pro Gln Glu Asp His
385             390             395             400

Ser Thr Thr Gln Pro Ala Lys Thr Thr Ser Gln Pro Thr Asn Ser Thr
                405             410             415

Glu Ser Thr Thr Leu Asn Pro Thr Ser Glu Pro Ser Ser Arg Gly Thr
            420             425             430

Gly Pro Ser Ser Pro Thr Val Pro Asn Thr Thr Glu Ser His Ala Glu
        435             440             445

Leu Gly Lys Thr Thr Pro Thr Thr Leu Pro Glu Gln His Thr Ala Ala
450             455             460

Ser Ala Ile Pro Arg Ala Val His Pro Asp Glu Leu Ser Gly Pro Gly
465             470             475             480

Phe Leu Thr Asn Thr Ile Arg Gly Val Thr Asn Leu Leu Thr Gly Ser
                485             490             495

Arg Arg Lys Arg Arg Asp Val Thr Pro Asn Thr Gln Pro Lys Cys Asn
            500             505             510

Pro Asn Leu His Tyr Trp Thr Ala Leu Asp Glu Gly Ala Ala Ile Gly
        515             520             525

Leu Ala Trp Ile Pro Tyr Phe Gly Pro Ala Ala Glu Gly Ile Tyr Thr
530             535             540

Glu Gly Ile Met Glu Asn Gln Asn Gly Leu Ile Cys Gly Leu Arg Gln
545             550             555             560

Leu Ala Asn Glu Thr Thr Gln Ala Leu Gln Leu Phe Leu Arg Ala Thr
                565             570             575

Thr Glu Leu Arg Thr Phe Ser Ile Leu Asn Arg Lys Ala Ile Asp Phe
            580             585             590

Leu Leu Gln Arg Trp Gly Gly Thr Cys His Ile Leu Gly Pro Asp Cys
        595             600             605

Cys Ile Glu Pro Gln Asp Trp Thr Lys Asn Ile Thr Asp Lys Ile Asp
610             615             620

Gln Ile Ile His Asp Phe Val Asp Asn Asn Leu Pro Asn Gln Asn Asp
625             630             635             640

Gly Ser Asn Trp Trp Thr Gly Trp Lys Gln Trp Val Pro Ala Gly Ile
                645             650             655

Gly Ile Thr Gly Val Ile Ile Ala Ile Ile Ala Leu Leu Cys Ile Cys
            660             665             670

Lys Phe Met Leu
        675

<210> SEQ ID NO 16
<211> LENGTH: 524
```

<212> TYPE: PRT
<213> ORGANISM: Tai Forrest virus (tc/CIV/1994/Pauleoula-CI strain)

<400> SEQUENCE: 16

```
Met Gly Ala Ser Gly Ile Leu Gln Leu Pro Arg Glu Arg Phe Arg Lys
1               5                   10                  15

Thr Ser Phe Phe Val Trp Val Ile Ile Leu Phe His Lys Val Phe Ser
            20                  25                  30

Ile Pro Leu Gly Val Val His Asn Asn Thr Leu Gln Val Ser Asp Ile
                35                  40                  45

Asp Lys Phe Val Cys Arg Asp Lys Leu Ser Ser Thr Ser Gln Leu Lys
    50                  55                  60

Ser Val Gly Leu Asn Leu Glu Gly Asn Gly Val Ala Thr Asp Val Pro
65                  70                  75                  80

Thr Ala Thr Lys Arg Trp Gly Phe Arg Ala Gly Val Pro Pro Lys Val
                85                  90                  95

Val Asn Cys Glu Ala Gly Glu Trp Ala Glu Asn Cys Tyr Asn Leu Ala
            100                 105                 110

Ile Lys Lys Val Asp Gly Ser Glu Cys Leu Pro Glu Ala Pro Glu Gly
        115                 120                 125

Val Arg Asp Phe Pro Arg Cys Arg Tyr Val His Lys Val Ser Gly Thr
130                 135                 140

Gly Pro Cys Pro Gly Leu Ala Phe His Lys Glu Gly Ala Phe Phe
145                 150                 155                 160

Leu Tyr Asp Arg Leu Ala Ser Thr Ile Ile Tyr Arg Gly Thr Thr Phe
                165                 170                 175

Ala Glu Gly Val Ile Ala Phe Leu Ile Leu Pro Lys Ala Arg Lys Asp
            180                 185                 190

Phe Phe Gln Ser Pro Pro Leu His Glu Pro Ala Asn Met Thr Thr Asp
        195                 200                 205

Pro Ser Ser Tyr Tyr His Thr Thr Thr Ile Asn Tyr Val Val Asp Asn
210                 215                 220

Phe Gly Thr Asn Thr Thr Glu Phe Leu Phe Gln Val Asp His Leu Thr
225                 230                 235                 240

Tyr Val Gln Leu Glu Ala Arg Phe Thr Pro Gln Phe Leu Val Leu Leu
                245                 250                 255

Asn Glu Thr Ile Tyr Ser Asp Asn Arg Arg Ser Asn Thr Thr Gly Lys
            260                 265                 270

Leu Ile Trp Lys Ile Asn Pro Thr Val Asp Thr Ser Met Gly Glu Trp
        275                 280                 285

Ala Phe Trp Glu Asn Lys Lys Asn Phe Thr Lys Thr Leu Ser Ser Glu
290                 295                 300

Glu Leu Ser Phe Val Pro Val Pro Ser Ala Ile Pro Arg Ala Val His
305                 310                 315                 320

Pro Asp Glu Leu Ser Gly Pro Gly Phe Leu Thr Asn Thr Ile Arg Gly
                325                 330                 335

Val Thr Asn Leu Leu Thr Gly Ser Arg Arg Lys Arg Arg Asp Val Thr
            340                 345                 350

Pro Asn Thr Gln Pro Lys Cys Asn Pro Asn Leu His Tyr Trp Thr Ala
        355                 360                 365

Leu Asp Glu Gly Ala Ala Ile Gly Leu Ala Trp Ile Pro Tyr Phe Gly
370                 375                 380

Pro Ala Ala Glu Gly Ile Tyr Thr Glu Gly Ile Met Glu Asn Gln Asn
385                 390                 395                 400
```

```
Gly Leu Ile Cys Gly Leu Arg Gln Leu Ala Asn Glu Thr Thr Gln Ala
                405                 410                 415

Leu Gln Leu Phe Leu Arg Ala Thr Thr Glu Leu Arg Thr Phe Ser Ile
            420                 425                 430

Leu Asn Arg Lys Ala Ile Asp Phe Leu Leu Gln Arg Trp Gly Gly Thr
        435                 440                 445

Cys His Ile Leu Gly Pro Asp Cys Cys Ile Glu Pro Gln Asp Trp Thr
    450                 455                 460

Lys Asn Ile Thr Asp Lys Ile Asp Gln Ile Ile His Asp Phe Val Asp
465                 470                 475                 480

Asn Asn Leu Pro Asn Gln Asn Asp Gly Ser Asn Trp Trp Thr Gly Trp
                485                 490                 495

Lys Gln Trp Val Pro Ala Gly Ile Gly Ile Thr Gly Val Ile Ile Ala
            500                 505                 510

Ile Ile Ala Leu Leu Cys Ile Cys Lys Phe Met Leu
        515                 520
```

```
<210> SEQ ID NO 17
<211> LENGTH: 18
<212> TYPE: PRT
<213> ORGANISM: Ebola virus

<400> SEQUENCE: 17

Trp Ala Glu Asn Cys Tyr Asn Leu Glu Ile Lys Lys Pro Asp Gly Ser
1               5                   10                  15

Glu Cys
```

```
<210> SEQ ID NO 18
<211> LENGTH: 18
<212> TYPE: PRT
<213> ORGANISM: Sudan virus

<400> SEQUENCE: 18

Trp Ala Glu Asn Cys Tyr Asn Leu Glu Ile Lys Lys Pro Asp Gly Ser
1               5                   10                  15

Glu Cys
```

```
<210> SEQ ID NO 19
<211> LENGTH: 18
<212> TYPE: PRT
<213> ORGANISM: Bundibugyo virus

<400> SEQUENCE: 19

Trp Ala Glu Asn Cys Tyr Asn Leu Asp Ile Lys Lys Ala Asp Gly Ser
1               5                   10                  15

Glu Cys
```

```
<210> SEQ ID NO 20
<211> LENGTH: 18
<212> TYPE: PRT
<213> ORGANISM: Reston virus

<400> SEQUENCE: 20

Trp Ala Glu Asn Cys Tyr Asn Leu Glu Ile Lys Lys Ser Asp Gly Ser
1               5                   10                  15

Glu Cys
```

```
<210> SEQ ID NO 21
```

```
<211> LENGTH: 18
<212> TYPE: PRT
<213> ORGANISM: Tai Forest virus

<400> SEQUENCE: 21

Trp Ala Glu Asn Cys Tyr Asn Leu Ala Ile Lys Lys Val Asp Gly Ser
1               5                   10                  15

Glu Cys

<210> SEQ ID NO 22
<211> LENGTH: 18
<212> TYPE: PRT
<213> ORGANISM: Marburg virus

<400> SEQUENCE: 22

Glu Ala Lys Thr Cys Tyr Asn Ile Ser Val Thr Asp Pro Ser Gly Lys
1               5                   10                  15

Ser Leu
```